(12) United States Patent
Andreiko et al.

(10) Patent No.: US 10,368,719 B2
(45) Date of Patent: Aug. 6, 2019

(54) REGISTERING SHAPE DATA EXTRACTED FROM INTRA-ORAL IMAGERY TO DIGITAL RECONSTRUCTION OF TEETH FOR DETERMINING POSITION AND ORIENTATION OF ROOTS

(71) Applicant: Ormco Corporation, Orange, CA (US)

(72) Inventors: Craig A. Andreiko; Robert F. Dillon, Bedford, NH (US); Bradley S. Carlson, Doylestown, PA (US); Vicente A. Reynal, Irvine, CA (US)

(73) Assignee: Ormco Corporation, Orange, CA (US)

( * ) Notice: Subject to any disclaimer, the term of this patent is extended or adjusted under 35 U.S.C. 154(b) by 842 days.

(21) Appl. No.: 14/209,441

(22) Filed: Mar. 13, 2014

(65) Prior Publication Data

US 2014/0272772 A1    Sep. 18, 2014

Related U.S. Application Data

(60) Provisional application No. 61/784,377, filed on Mar. 14, 2013.

(51) Int. Cl.
| | | |
|---|---|---|
| A61C 7/00 | (2006.01) |
| A61B 1/00 | (2006.01) |
| A61B 1/24 | (2006.01) |
| A61B 5/055 | (2006.01) |
| A61B 6/03 | (2006.01) |
| A61B 6/00 | (2006.01) |
| A61B 5/11 | (2006.01) |
| G06T 7/00 | (2017.01) |
| A61B 6/14 | (2006.01) |

(52) U.S. Cl.
CPC ........ *A61B 1/00009* (2013.01); *A61B 1/0002* (2013.01); *A61B 1/24* (2013.01); *A61B 5/055* (2013.01); *A61B 5/1111* (2013.01); *A61B 6/032* (2013.01); *A61B 6/4085* (2013.01); *A61C 7/002* (2013.01); *G06T 7/0016* (2013.01); *A61B 6/14* (2013.01); *G06T 2200/04* (2013.01); *G06T 2207/10072* (2013.01); *G06T 2207/30036* (2013.01)

(58) Field of Classification Search
CPC ....... A61C 7/00; A61C 7/002; A61C 13/0004; A61C 9/004; A61C 9/0053; A61C 9/0046; G06T 19/00–19/20; A61B 5/1111; A61B 6/032
USPC ......... 433/24, 215; 700/95, 97, 98; 382/128, 382/154, 291
See application file for complete search history.

(56) References Cited

U.S. PATENT DOCUMENTS

| | | | | |
|---|---|---|---|---|
| 2002/0082492 A1* | 6/2002 | Grzeszczuk | ........... | A61B 90/36 600/407 |
| 2004/0197727 A1* | 10/2004 | Sachdeva | ................. | A61C 7/00 433/24 |
| 2011/0311946 A1* | 12/2011 | Sailer | ................... | A61C 8/0012 433/173 |

(Continued)

*Primary Examiner* — Yogesh P Patel
(74) *Attorney, Agent, or Firm* — Wood Herron & Evans LLP

(57) ABSTRACT

Provided are a system, method, and computer readable storage medium for using a digital reconstruction of a tooth, wherein the digital reconstruction includes a crown and a root. An image of the crown of the tooth is acquired, subsequent to a movement of the tooth. The shape data of the crown is extracted from the image and registered to the digital reconstruction of the tooth.

7 Claims, 47 Drawing Sheets

(56) References Cited

U.S. PATENT DOCUMENTS

| | | | |
|---|---|---|---|
| 2012/0015316 A1* | 1/2012 | Sachdeva | G06T 17/00 433/24 |
| 2013/0172731 A1* | 7/2013 | Gole | A61B 5/0035 600/424 |
| 2014/0294273 A1* | 10/2014 | Jaisson | A61B 5/7425 382/131 |
| 2014/0329194 A1* | 11/2014 | Sachdeva | A61C 7/002 433/24 |

* cited by examiner

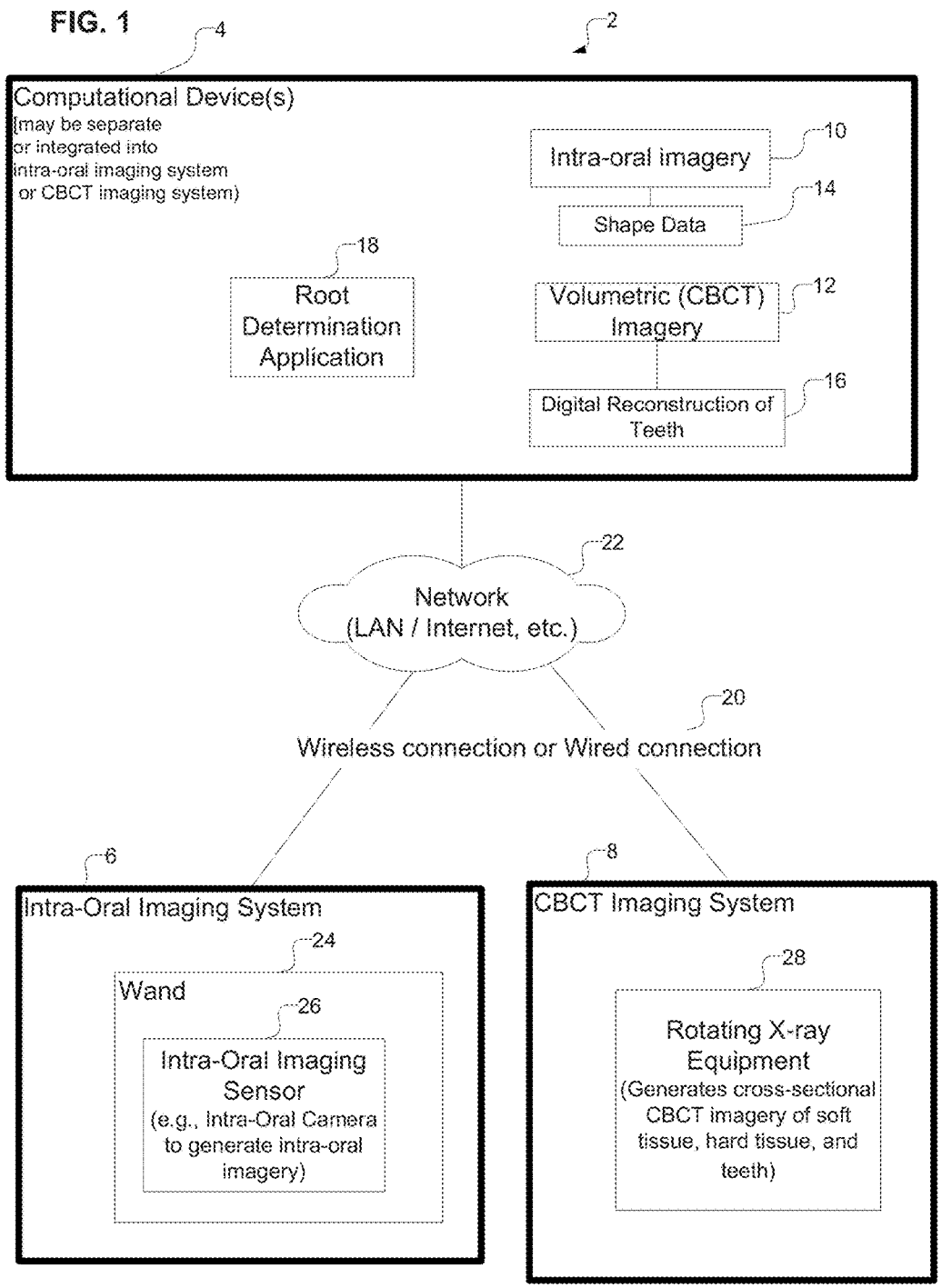

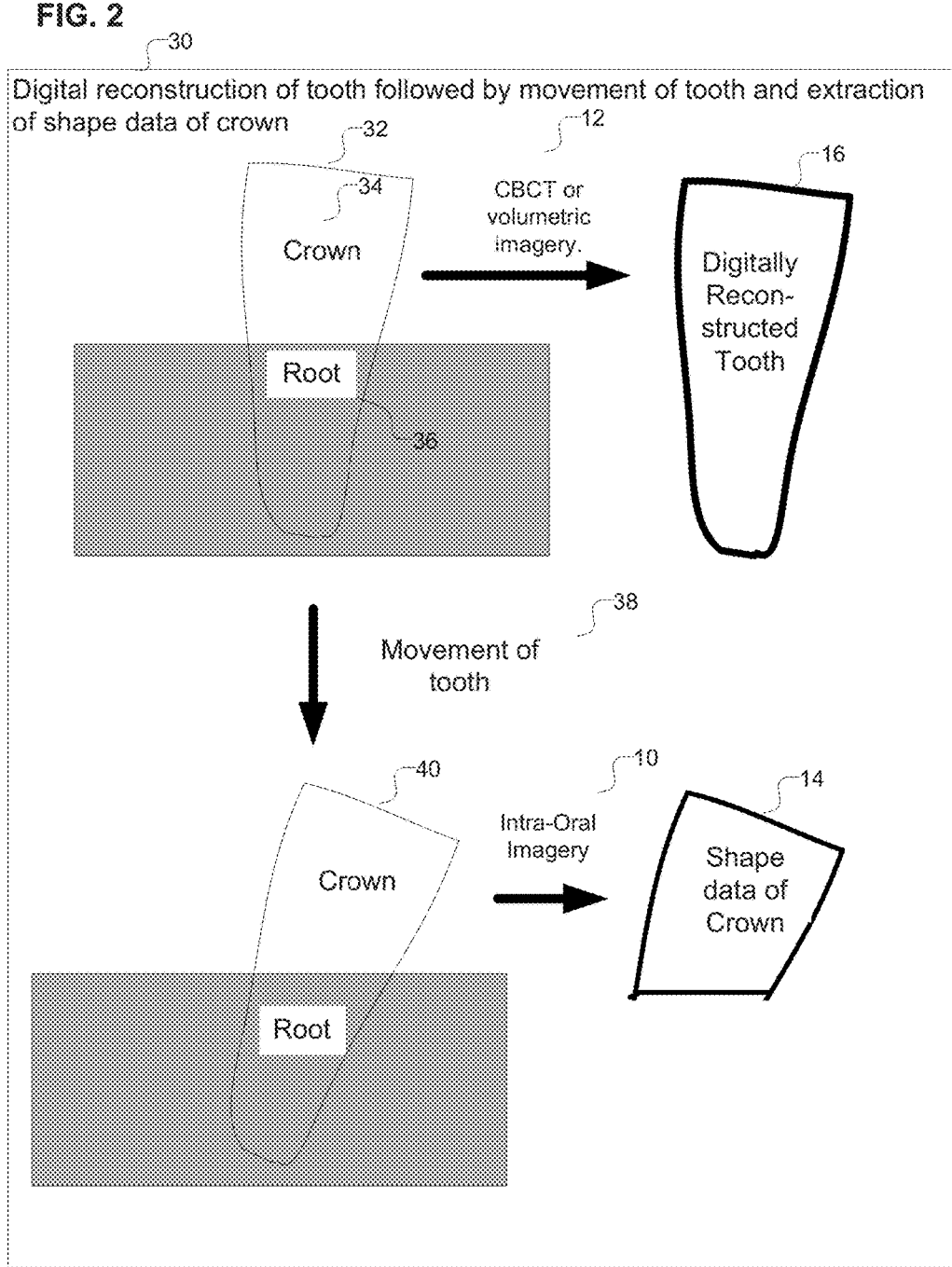

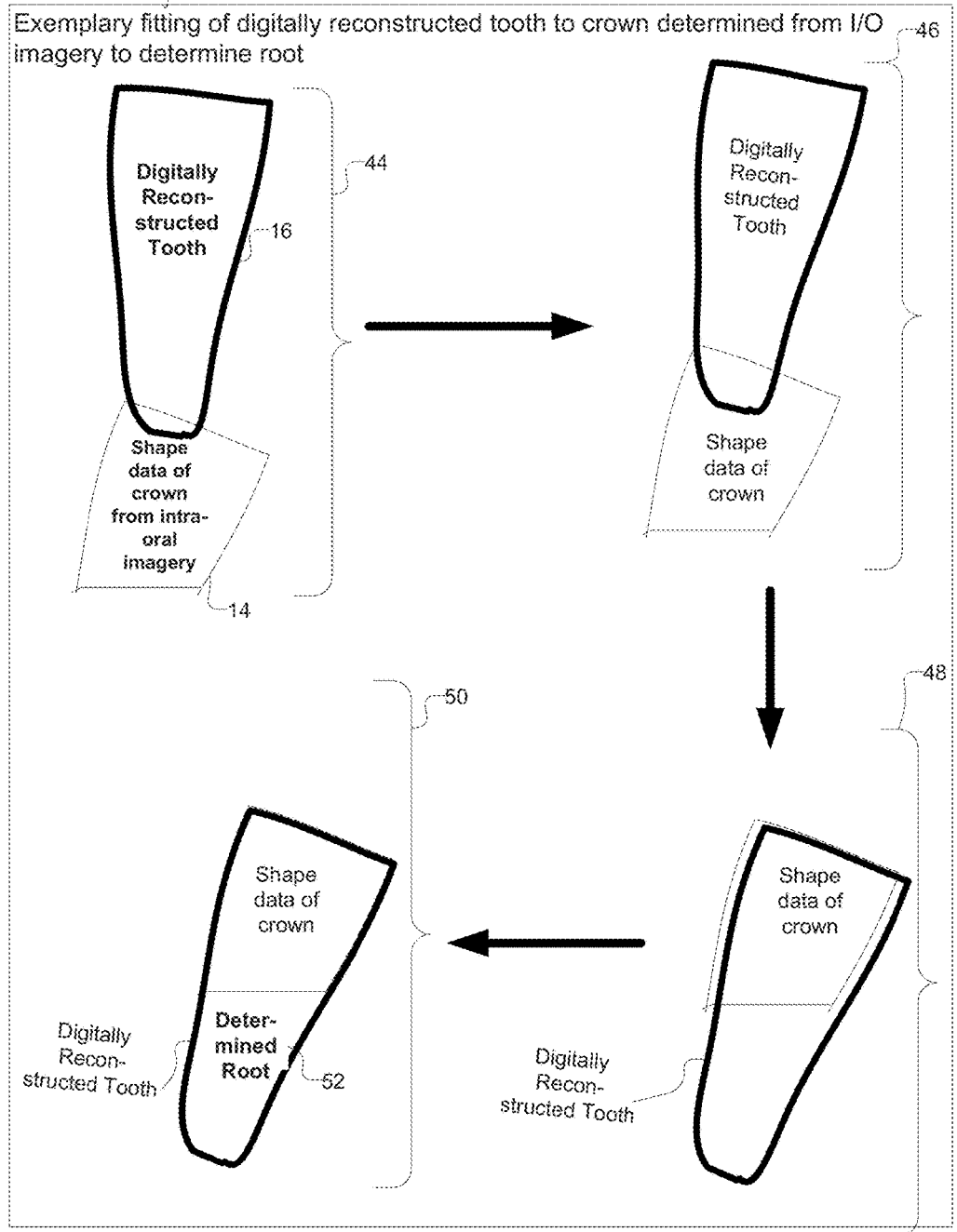

FIG. 4

Determination of roots for a plurality of teeth (when CBCT imagery and intra-oral imagery acquired at the first patient visit)

Digital Reconstruction of a plurality of teeth (from CBCT imagery)

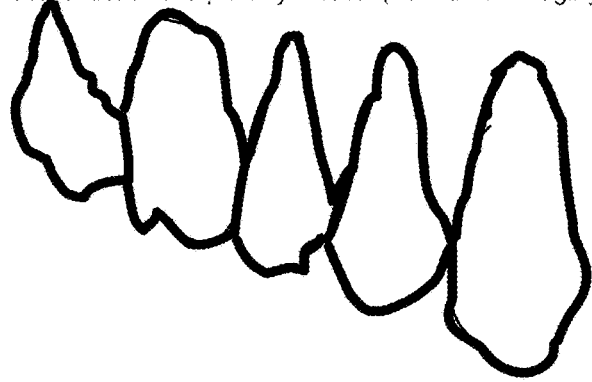

Shape Data for a plurality of crowns (from Intra-Oral imagery)

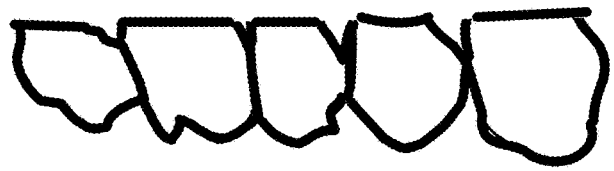

Best Fit of shape data of a plurality of crowns to the digital reconstruction

Determined roots (hatched line) in the digital reconstruction of teeth

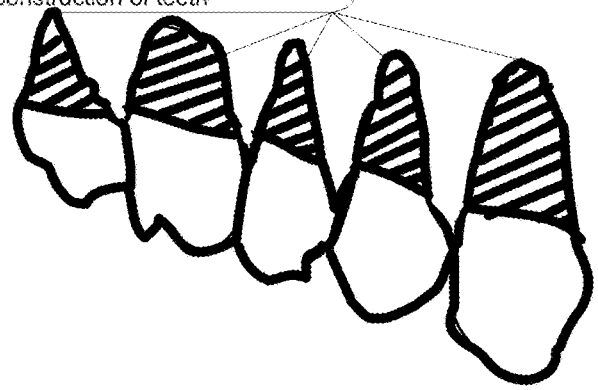

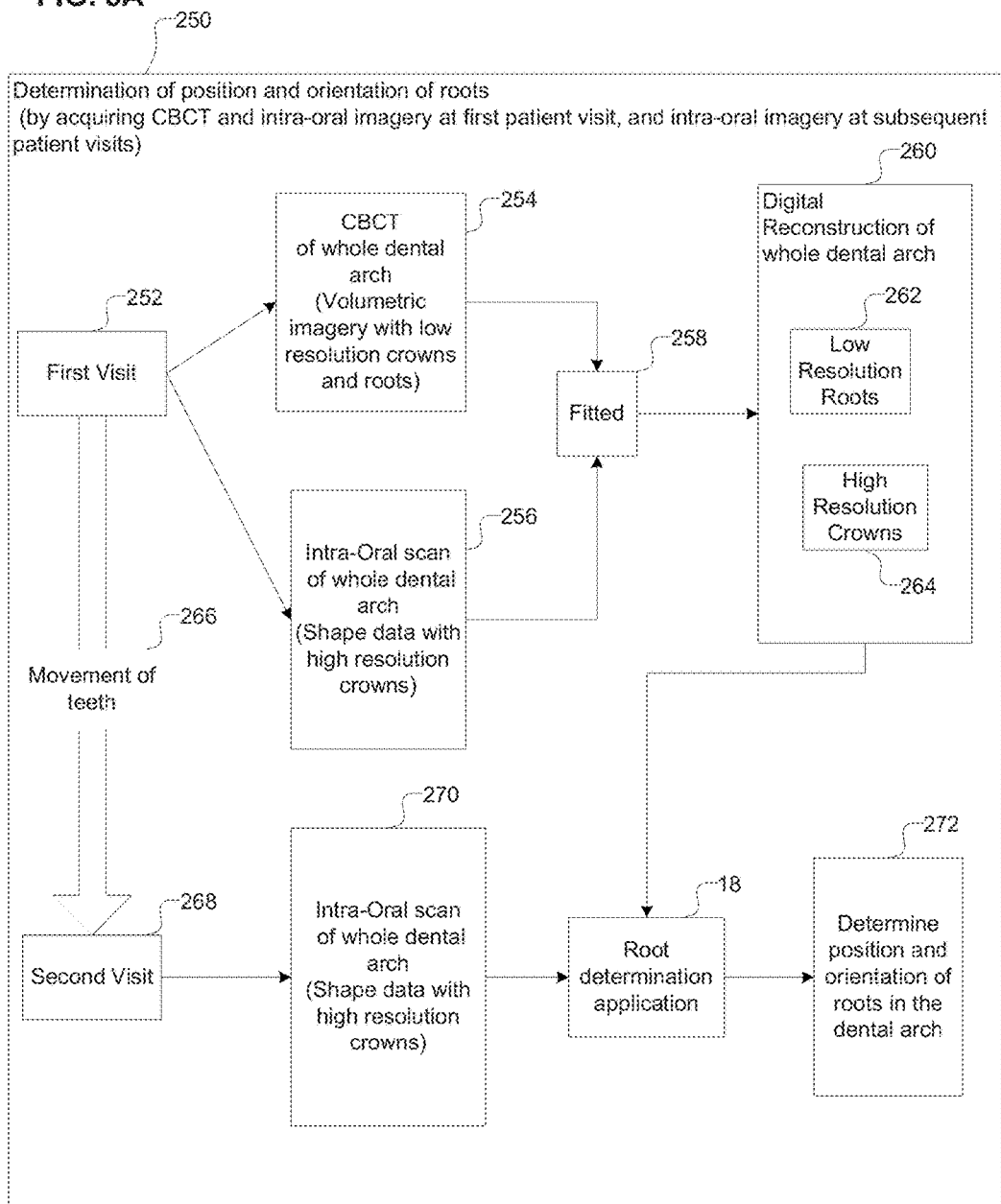

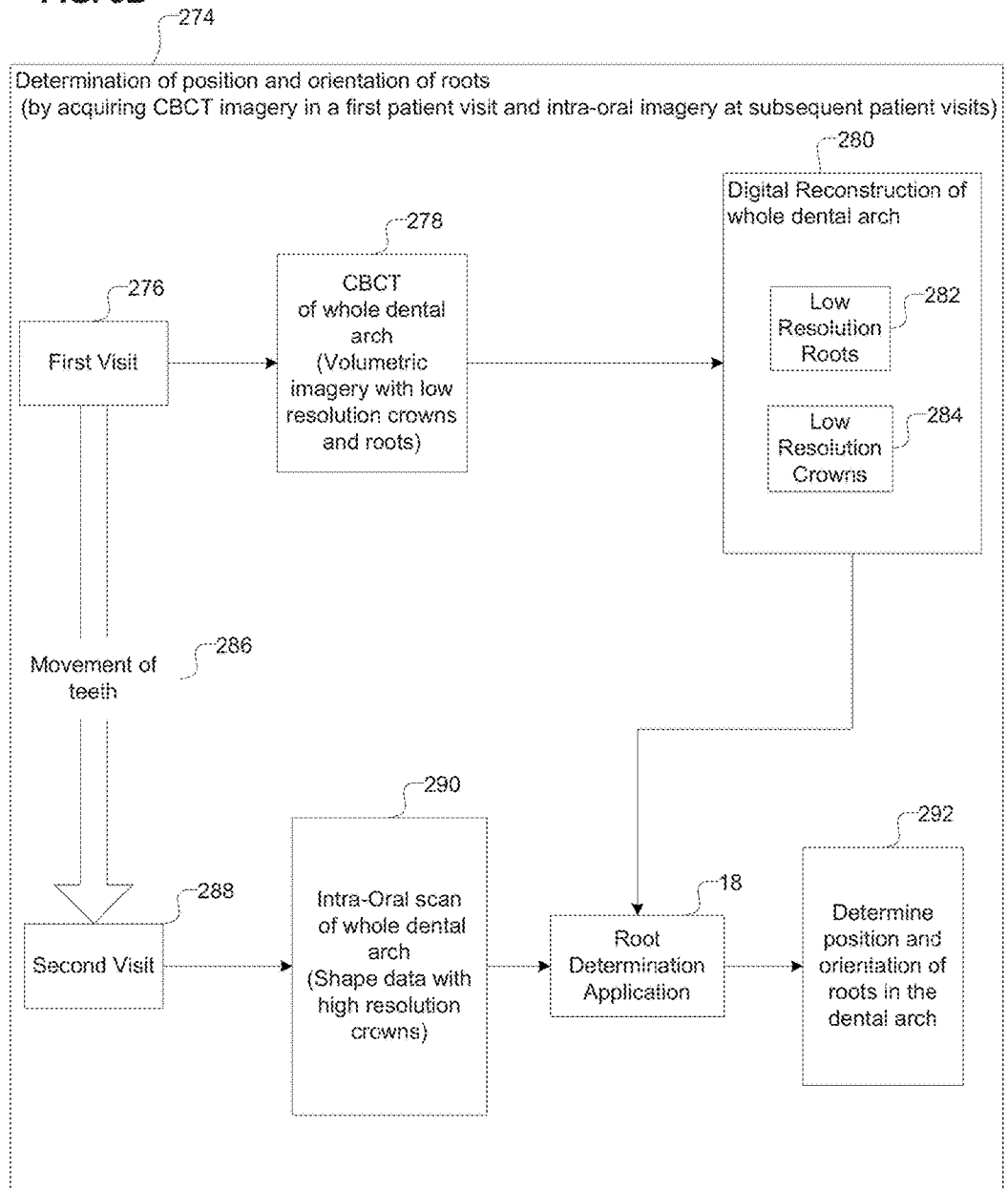

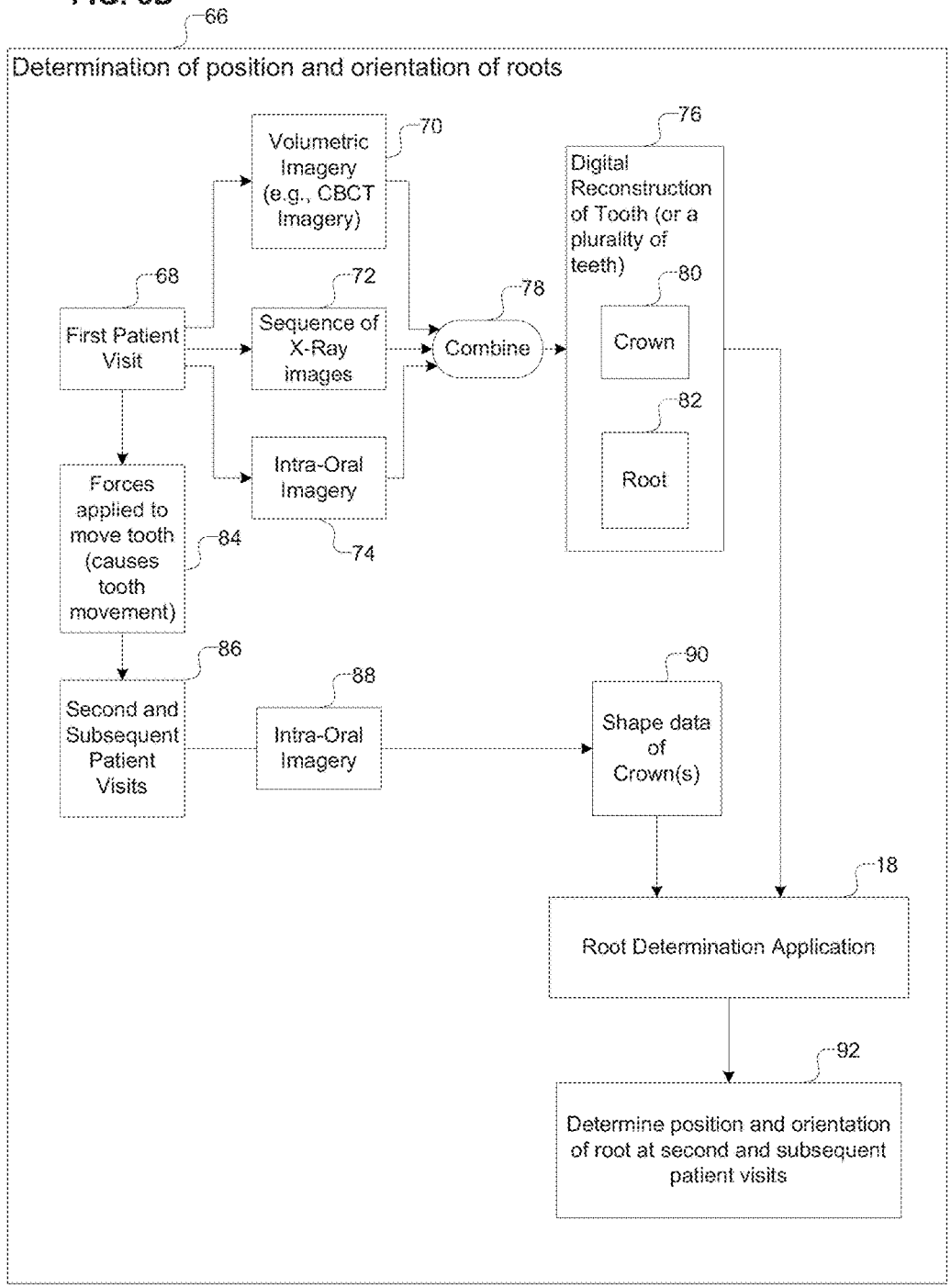

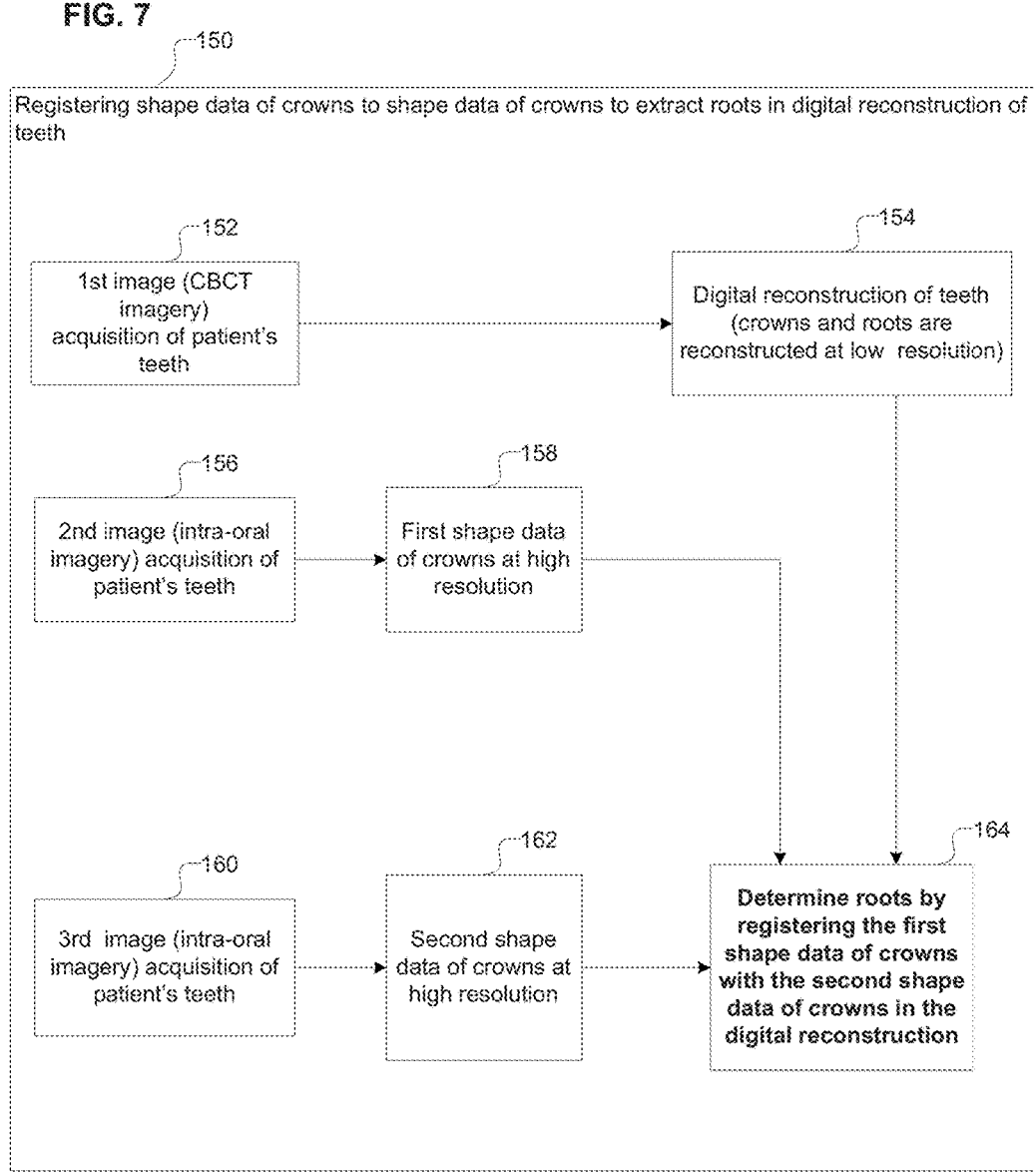

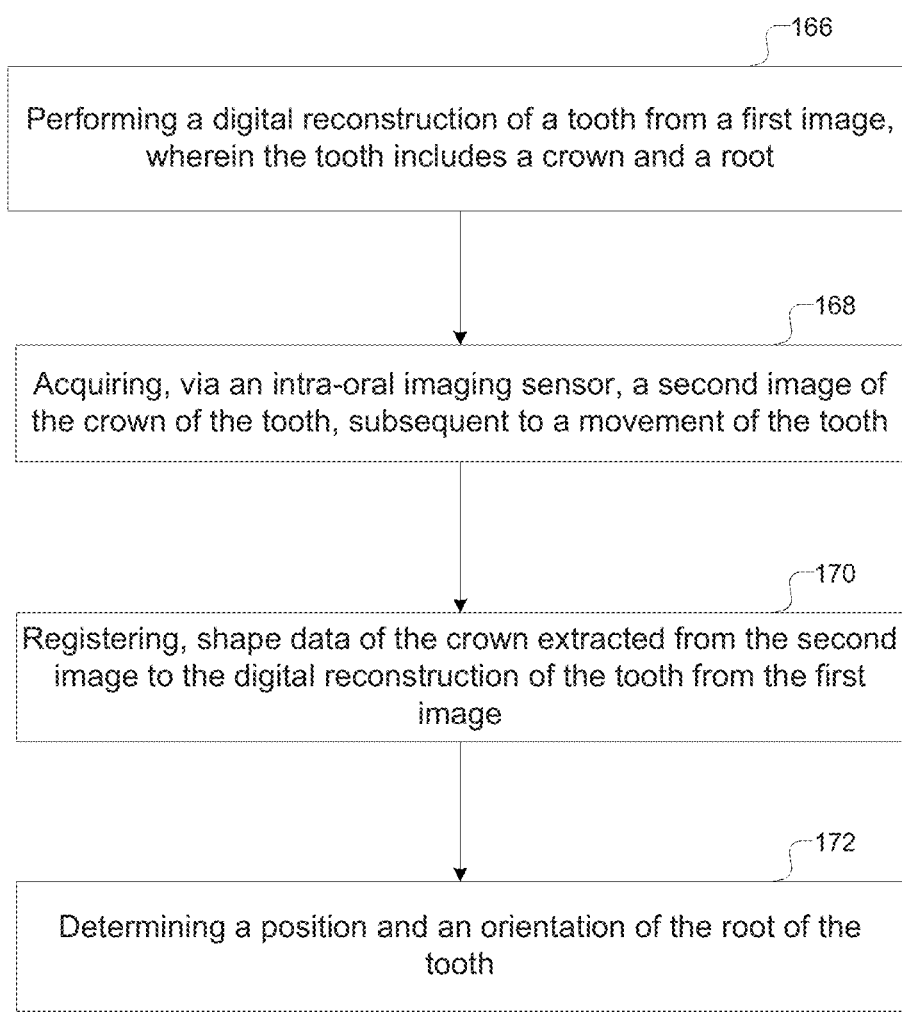

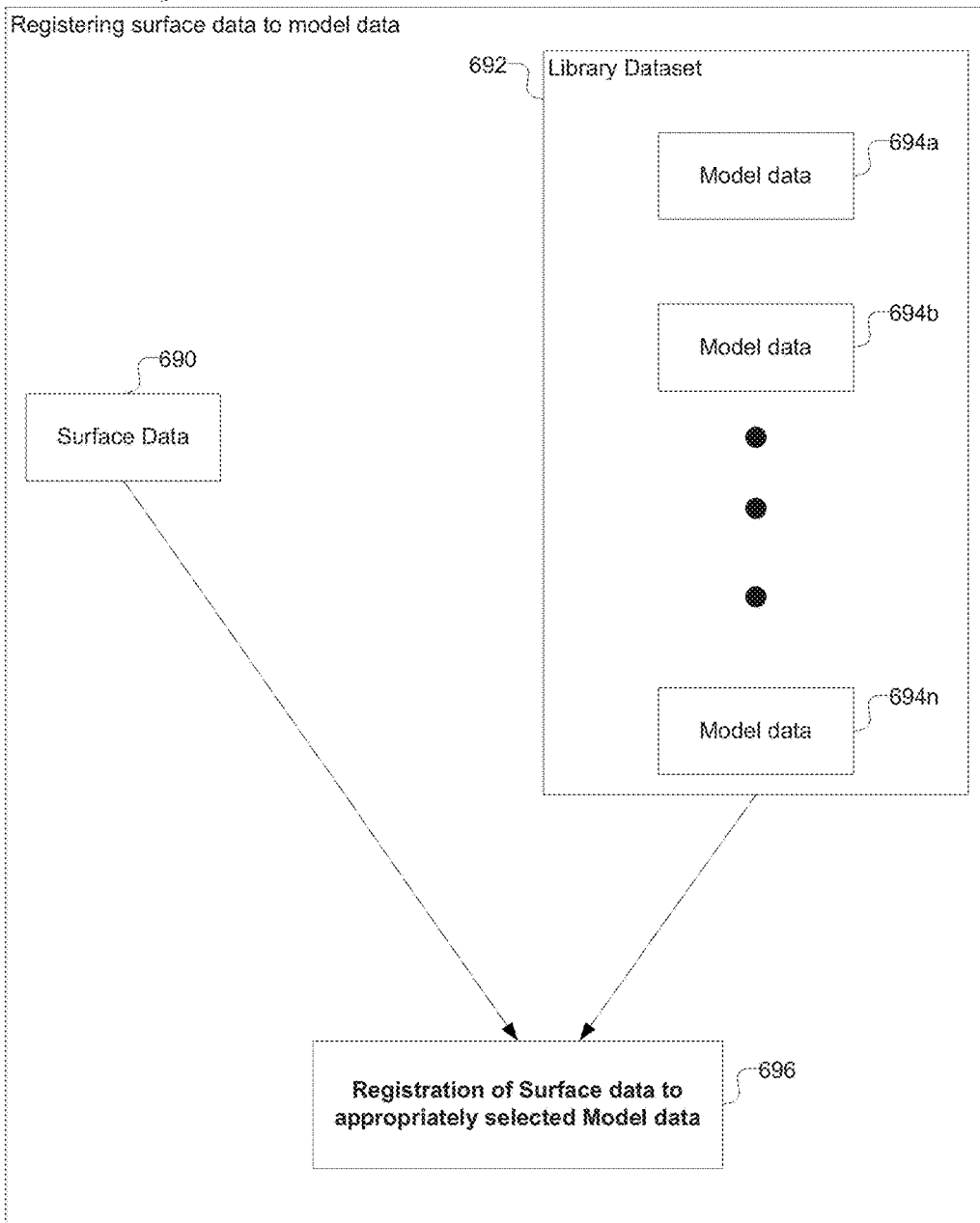

FIG. 23

700 — Flowchart for augmenting CBCT imagery with data from intra-oral imagery to determine boundary between roots and crowns

702 — Receiving, via a computational device, intra-oral imagery and cone beam computed tomography (CBCT) imagery

704 — Determining one or more crowns in the intra-oral imagery, wherein the one or more crowns are represented by limited length vectors or voxels, and the CBCT imagery is represented by voxels

706 — Integrating the one or more crowns determined in the intra-oral imagery into the CBCT imagery by registering the limited length vectors or voxels that represent the one or more crowns in the intra-oral imagery with the voxels of the CBCT imagery, to determine a boundary between at least one crown and at least one root in the CBCT imagery

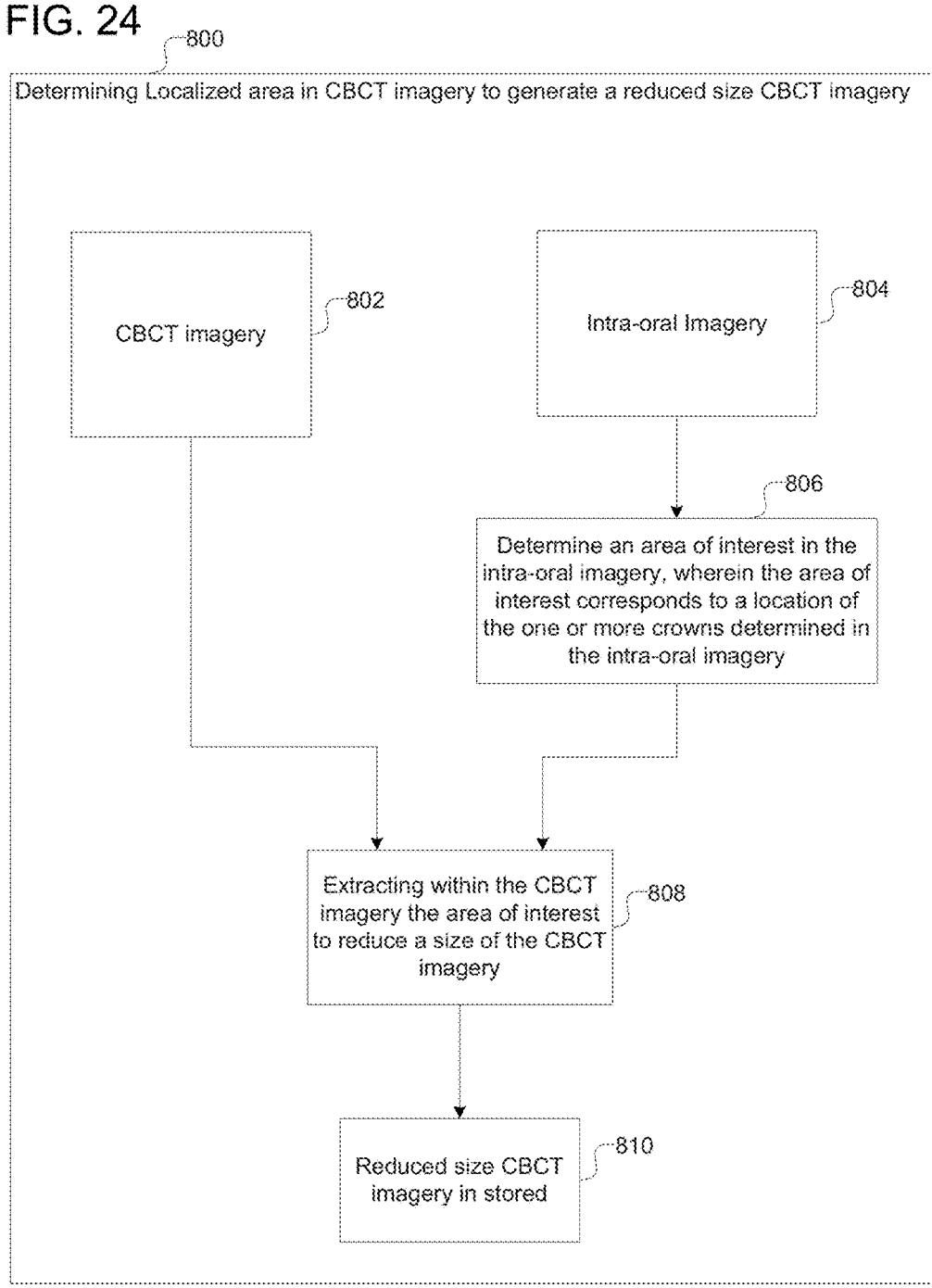

REGISTERING SHAPE DATA EXTRACTED FROM INTRA-ORAL IMAGERY TO DIGITAL RECONSTRUCTION OF TEETH FOR DETERMINING POSITION AND ORIENTATION OF ROOTS

CROSS-REFERENCE TO RELATED APPLICATION

This application claims the benefit of U.S. Provisional Application No. 61/784,377, filed Mar. 14, 2013, which is incorporated by reference in its entirety.

1. FIELD

The disclosure relates to a system, method, and computer readable storage medium for registering shape data extracted from intra-oral imagery to digital reconstruction of teeth for determining position and orientation of roots.

2. BACKGROUND

An intra-oral (I/O) imaging system is a diagnostic equipment that allows a dental practitioner to see the inside of a patient's mouth and display the topographical characteristics of teeth on a display monitor. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingivae. The 3D intra-oral imager may be fabricated in the form of a slender rod that is referred to as a wand or a handpiece. The wand may be approximately the size of a dental mirror with a handle that is used in dentistry. The wand may have a built-in light source and a video camera that may achieve an imaging magnification, ranging in scale from $\frac{1}{10}$ to 40 times or more. This allows the dental practitioner to discover certain types of details and defects of the teeth and gums. The images captured by the intra-oral camera may be displayed on a display monitor and may be transmitted to a computational device.

Cone beam computed tomography (CBCT) involves the use of a rotating CBCT scanner, combined with a digital computer, to obtain images of the teeth and surrounding bone structure, soft tissue, muscle, blood vessels, etc. CBCT may be used in a dental practitioner's office to generate cross-sectional images of teeth and the surrounding bone structure, soft tissue, muscle, blood vessels, etc. During a CBCT scan, the CBCT scanner rotates around the patient's head and may obtain hundreds of distinct projection images that may be referred to as CBCT imagery. The CBCT imagery may be transmitted to a computational device. The CBCT imagery may be analyzed to generate three-dimensional anatomical data. The three-dimensional anatomical data can then be manipulated and visualized with specialized software to allow for cephalometric analysis of the CBCT imagery.

Orthodontics is a specialty of dentistry that is concerned with improvement of the general appearance of a patient's teeth and also the correction of malocclusions, crookedness and other flaws of the teeth. Orthodontic braces are devices that are placed on a patient's teeth by a dental practitioner. Often, such orthodontic braces are periodically adjusted by the dental practitioner to help align and straighten the teeth. Treatment by the dental practitioner may help in repositioning the teeth to correct flaws and improve the general appearance of the patient. The dental practitioner may take impressions and/or capture X-ray images of the teeth and the surrounding skeletal structure. The dental practitioner may write a prescription based on an analysis of the impression of the teeth, the X-ray images, the CBCT images, etc. While performing the analysis the dental practitioner may use software for cephalometric analysis of CBCT images, panoramic X-rays, and cephalometric X-rays. The prescription written by the dental practitioner may be used to manufacture an orthodontic brace, in a traditional orthodontic brace, wires interact with brackets to move teeth to a desired position. Periodic adjustments are needed to the orthodontic brace for satisfactory completion of treatment.

SUMMARY OF THE PREFERRED EMBODIMENTS

Provided are a system, method, and computer readable storage medium for using a digital reconstruction of a tooth, wherein the digital reconstruction includes a crown and a root. An image of the crown of the tooth is acquired, subsequent to a movement of the tooth. The shape data of the crown is extracted from the image and registered to the digital reconstruction of the tooth.

In certain embodiments, the digital reconstruction is from volumetric imagery selected from a group consisting of tomographic imagery, ultrasonic imagery, cone beam computed tomography (CBCT) imagery and magnetic resonance imagery (MRI). The image of the crown of the tooth is acquired via an intra-oral imaging system.

In further embodiments, a position and an orientation of the root of the tooth is determined, subsequent to the registering.

In additional embodiments, subsequent to movements of teeth, a plurality of crowns extracted from the image are registered to the digital reconstruction that includes the plurality of crowns and a corresponding plurality of roots, wherein a spatial relationship of each crown to any adjacent crown of the plurality of crowns is maintained during registration. In yet additional embodiments, the image is a second image, wherein the digital reconstruction is performed from a first image, and wherein the first image and the second image are taken at different times.

In further embodiments, the tooth undergoes the movement while continuing to remain rigid, wherein the movement of the tooth is caused by applying forces to the tooth.

In yet further embodiments, acquisition of at least one image for the digital reconstruction includes exposing a patient to radiation, and acquisition of the image of the crown avoids exposing the patient to any radiation.

In additional embodiments, the performing of the digital reconstruction of the tooth further comprises: receiving first shape data of the crown and volumetric imagery of the tooth, wherein the first shape data is received prior to the shape data; determining elements that represent the crown in the first shape data; and registering the elements with corresponding voxels of the volumetric imagery by determining volumetric coordinates and radiodensities corresponding to the voxels.

In yet additional embodiments, the performing of the digital reconstruction of the tooth further comprises: determining orientation of the tooth from first shape data of the crown and volumetric imagery of the tooth, where the first shape data is received prior to the shape data; and registering the first shape data of the crown with model data, based on the determined orientation of the tooth.

In certain embodiments, shape data of crowns extracted from images acquired from a patient in a second patient visit is registered to shape data of crowns extracted from images acquired from a patient in a first patient visit, to determine position and orientation of corresponding roots.

Provided also is an imaging system for using a digital reconstruction of a tooth, where the digital reconstruction includes a crown and a root. The imaging system comprises an imaging sensor to acquire an image of the crown of the tooth, subsequent to a movement of the tooth, and a processor to register shape data of the crown extracted from the image to the digital reconstruction of the tooth.

BRIEF DESCRIPTION OF THE DRAWINGS

Referring now to the drawings in which like reference numbers represent corresponding parts throughout:

FIG. 1 illustrates a block diagram of a computing and imaging environment that includes a computational device in communication with an intra-oral imaging system and a CBCT imaging system, in accordance with certain embodiments;

FIG. 2 illustrates a diagram that shows digital reconstruction of tooth, followed by movement of tooth and extraction of shape data of crown, in accordance with certain embodiments;

FIG. 3 illustrates a diagram that shows exemplary fitting of digitally reconstructed tooth to crown, in accordance with certain embodiments;

FIG. 4 illustrates a diagram that shows determination of root position and orientation for a plurality of teeth, in accordance with certain embodiments;

FIG. 5A illustrates a block diagram that shows how position and orientation of roots are determined by acquiring CBCT and intra-oral imagery in a first patient visit, and intra-oral imagery in subsequent patient visits, in accordance with certain embodiments;

FIG. 5B illustrates a block diagram that shows how position and orientation of roots are determined by acquiring CBCT imagery in a first patient visit and intra-oral imagery in subsequent patient visits, in accordance with certain embodiments;

FIG. 5D illustrates a block diagram that shows how position and orientation of roots are determined in a plurality of patient visits, in accordance with certain embodiments;

FIG. 7 illustrates a diagram that shows how shape data of crowns taken at two different patient visits are registered to each other to extract roots in a digital reconstruction of teeth, in accordance with certain embodiments;

FIG. 8 illustrates a flowchart that shows how position and orientation of a root are determined, in accordance with certain embodiments;

FIG. 22 illustrates a diagram that shows how surface data extracted from intra-oral imagery is fitted to model data maintained as a library dataset;

FIG. 23 illustrates a flowchart for augmenting CBCT imagery with data from intra-oral imagery to determine boundary between roots and crowns, in accordance with certain embodiments;

FIG. 24 illustrates a flowchart for determining a localized area in CBCT imagery to generate a reduced size CBCT imagery, by augmenting CBCT imagery with data from intra-oral imagery, in accordance with certain embodiments;

DETAILED DESCRIPTION

Figure 5C:
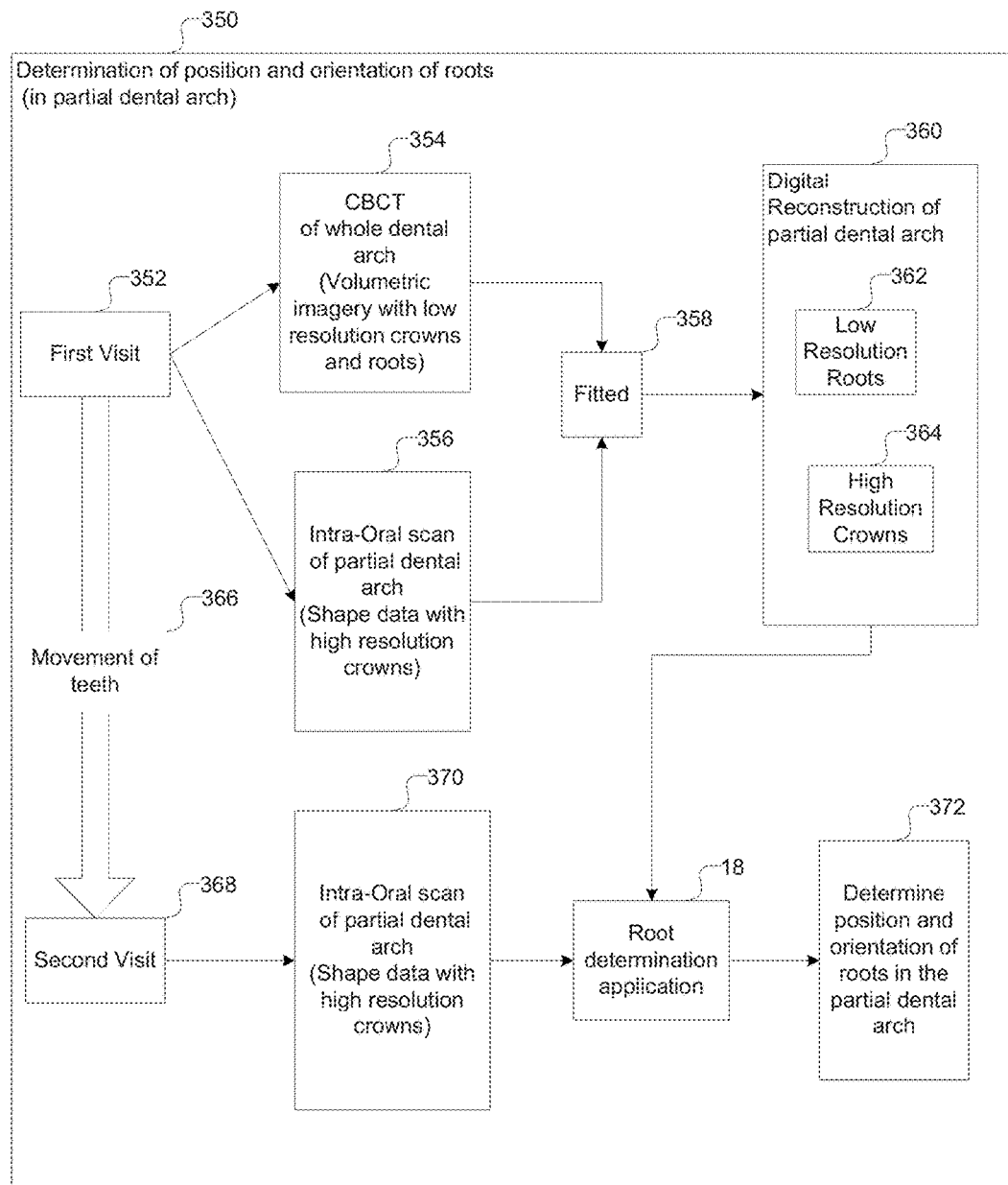
FIG. 5C illustrates a block diagram that shows how position and orientation of roots are determined in a partial dental arch, in accordance with certain embodiments.

In the following description, reference is made to the accompanying drawings which form a part hereof and which illustrate several embodiments. It is understood that other embodiments may be utilized and structural and operational changes may be made.

It may be desirable to reduce the exposure of a patient to potentially harmful radiation. Imaging via intra-oral imaging devices do not expose the patient to any harmful radiation, whereas repeated and frequent exposures to imaging via CBCT imaging systems, X-Ray imaging systems, etc., may expose the patient to radiation. As a result, it may be desirable to use intra-oral imaging devices in preference to CBCT imaging systems and X-Ray systems, whenever a substitution is feasible.

In orthodontic procedures, a patient may undergo imaging via. CBCT imaging devices in multiple visits, to determine how a plurality of teeth including the roots may have moved from visit to visit. The dental practitioner may be particularly interested in the position and orientation of the roots at each visit, since the position and orientation of the roots may dictate the forces that may have to be applied via braces or other mechanisms to make the teeth undergo movement.

Certain embodiments allow a dental practitioner to acquire a CBCT or other volumetric image of the patient's teeth in no more than one visit of the patient, and acquire intra-oral images in other visits of the patient. Intra-oral images may also be acquired during the visit in which the CBCT or other volumetric image is acquired. The shape data (i.e., the surface data) of a plurality of crowns acquired from intra-oral imagery is fitted to the digital reconstruction of a plurality of teeth to determine the position and orientation of a plurality of roots. As a result, the patient is exposed to a lesser amount of radiation, in comparison to the situation in which CBCT images are acquired at multiple patient visits.

In certain embodiments, the digital reconstruction of the plurality of teeth may be determined from volumetric imagery, or from a combination of volumetric imagery with intra-oral imagery, or from a combination of model data, volumetric imagery, and intra-oral imagery, or via other mechanisms.

Exemplary Embodiments

FIG. 1 illustrates a block diagram of a computing and imaging environment 2 that includes a computational device 4 in communication with an intra-oral imaging system 6 and a CBCT imaging system 8, in accordance with certain embodiments. The computational device 4 may include any suitable computational device such as a personal computer, a server computer, a mini computer, a mainframe computer, a blade computer, a tablet computer, a touch screen computing device, a telephony device, a cell phone, a mobile computational device, a dental equipment having a processor, etc., and in certain embodiments the computational device 4 may provide web services or cloud computing services. In certain alternative embodiments, more than one computational device may be used for storing data or performing the operations performed by the computational device 4.

The intra-oral imaging system 6 provides intra-oral imagery 10 of a patient's crown and the CBCT imaging system 8 provides volumetric imagery 12 of a patient's tooth, where the tooth may include both the crown and the root. The CBCT imagery 12 typically includes imagery of the entire maxillary and mandibular arches, whereas the intra-oral imagery 10 may be of entire dental arches or partial dental arches. In alternative embodiments, the shape (i.e., surface) data of the patient's crown may be provided by imagery that is different from intra-oral imagery, such as via, imagery captured from a physical impression of the patient's crown, and the volumetric imagery may be provided by other types of tomographic imagery, ultrasonic imagery, magnetic resonance imagery MRI), etc.

The computational device 4 may include a root determination application 18, implemented in certain embodiments in software, hardware, firmware or any combination thereof. Other applications that may potentially be integrated into the root determination application 18 may also be included in the computational device 4. The root determination application 18 integrates the intra-oral imagery 10 acquired by the intra-oral imaging system 6 and the CBCT imagery 12 acquired by the CBCT imaging system 8, to provide additional functionalities that are not found in either the intra-oral imagery 10 or the CBCT imagery 12 when they are not integrated. In particular, the root determination application 18 determines roots by fitting the shape data 14 of the crowns of intra-oral imagery 10 to a digital reconstruction of teeth 16 obtained at least from the CBCT imagery 12 or via other mechanisms. The digital reconstruction of teeth 16 may be represented via voxels or other three-dimensional reconstruction mechanisms, and the shape data 14 may be represented by limited length vectors, surfaces, wireframes, curves, patches, tessellations, voxels, etc.

The computational device 4 is coupled via one or more wired or wireless connections 20 to an intra-oral imaging system 6 and a CBCT imaging system 8, over a network 22. In certain embodiments, the network 22 may comprise a local area network, the Internet, and intranet, a storage area network, or any other suitable network.

The intra-oral imaging system 6 may include a wand 24 having an intra-oral imaging sensor 26, where in certain embodiments the intra-oral imaging sensor 26 is an intra-oral camera that generates intra-oral imagery of the oral cavity of a patient. The CBCT imaging system 8 may include a rotating X-ray equipment 28 that generates cross-sectional CBCT imagery of the soft tissue, hard tissue, teeth, etc. of a patient.

Therefore, FIG. 1 illustrates certain embodiments in which the root determination application 18 determines roots by fitting the shape data 14 of the crowns of intra-oral imagery 10 to a digital reconstruction of teeth 16 obtained at least from the CBCT imagery 12. In certain additional embodiments, the intra-oral imagery 10 and the CBCT imagery 12 may be stored in a storage medium (e.g., a disk drive, a floppy drive, a pen drive, a solid state device, an optical drive, etc.), and the storage medium may be coupled to the computational device 4 for reading and processing by the root determination application 18. In additional embodiments, certain operations performed by the computational device 4 may be performed by the intra-oral imaging system 6 or the CBCT imaging system 8. In particular, the root determination application 18 may be located in the intra-oral imaging system 6, the CBCT imaging system 8, and/or the computational device 4, and may determine roots by combining shape data 14 of crowns with digital reconstruction of teeth 16 in the computational device 4, the intra-oral imaging system 6 or the CBCT imaging system 8.

FIG. 2 illustrates a diagram 30 that shows digital reconstruction of tooth, followed by movement of tooth and extraction of shape data of crown, in accordance with certain embodiments. Certain of the operations shown in FIG. 2 may be performed by the computational device 4, the intra-oral imaging system 6 or by the CBCT imaging system 8.

A digitally reconstructed tooth 16 may be determined from CBCT or other volumetric imagery 12 of a tooth 32, where the tooth may have a crown 34 and a root 36. The crown 34 is the portion of the tooth 32 that is visible above the gum (i.e., gingiva) and the root 36 is the portion of the tooth that is located inside the gum.

After the CBCT imagery 12 has been acquired, the tooth 32 may undergo movement 38 and the moved tooth is shown via reference numeral 40. The intra-oral imaging system 6 may be used to image the moved tooth 40 without the use of any harmful radiation, to generate intra-oral imagery 10. Shape data 14 of the crown is determined from the intra oral imagery 10. It may be noted that the tooth 32 is a rigid object that retains its rigidity after undergoing movement 38.

FIG. 3 illustrates a diagram 42 that shows exemplary fitting of digitally reconstructed tooth to shape data of a crown, in accordance with certain embodiments. Certain of the operations shown in FIG. 3 may be performed by the computational device 4, the intra-oral imaging system 6 or by the CBCT imaging system 8.

Reference numerals 44, 46, 48, 50 show how the shape data of crown 14 obtained from the intra-oral imagery 10 is fitted to the digitally reconstructed tooth 16 to determine the root 52. The shape data 14 of the crown may be positioned and oriented to fit into the digital reconstruction 16 of the tooth and the portion of the digital reconstruction 16 that is not overlaid by the shape data 14 is the root 52 that is determined.

While FIG. 3 shows fitting shape data of a single crown to the digital reconstruction of a single tooth to determine a single root, in certain embodiments, a plurality of crowns (such as that for an entire dental arch) may have to be fitted to the digital reconstruction a plurality of teeth to determine a plurality of roots. The relative position of a plurality of crowns imaged by the intra-oral imaging system 6 may have to be maintained while fitting the shape data of the plurality of crowns to the digital reconstruction of the plurality of teeth. It should be noted, that if the fitting is performed, subsequent to teeth movements after the digital reconstruction, then each individual crown may have to be fitted to each individual tooth of the digital reconstruction. However, in certain embodiments, if intra-oral images and CBCT images are acquired during the same visit of a patient, then a plurality of crown surfaces of the intra-oral images may be collectively fitted to the digital reconstruction of the plurality of teeth obtained from the CBCT images.

FIG. 4 illustrates a diagram 54 that shows determination of root position and orientation when CBCT imagery and intra-oral imagery are both acquired during a first patient visit, in accordance with certain embodiments. Certain of the operations shown in FIG. 4 may be performed by the computational device 4, the intra-oral imaging system 6 or by the CBCT imaging system 8.

The digital reconstruction of a plurality of teeth as determined from CBCT imagery 12 is shown via reference numeral 56. The shape data of crowns as determined from intra-oral imagery 10 is shown via reference numeral 58. It should be noted that the CBCT imagery for the digital reconstruction 56 and the intra-oral imagery for the shape data 58 may both be acquired during a first patient visit, i.e., there are no tooth movements between the acquisition of the CBCT imagery and the intra-oral imagery. In certain embodiments, the shape data for the plurality of crowns 58 is fitted (as shown via reference numeral 60) with the digital reconstruction of the plurality of teeth 56 to determine (reference numeral 62) the roots (reference numeral 64) in the digital reconstruction of teeth. In other embodiments, the intra-oral images provide relatively high resolution crowns to replace the relatively low resolution crowns that are present in the digital reconstruction of teeth from CBCT imagery.

It may be noted that a tooth may have six degrees of freedom while moving. The six degrees of freedom include three rotational components and three translational components. Since a full or partial dental arch having a plurality of teeth may be imaged for treatment purposes, shape data of a plurality of crowns may have to be fitted with the digital reconstruction of a plurality of teeth for treatment purposes. While fitting the shape data of the plurality of crowns to the digital reconstruction of the plurality of teeth the relative position and orientation of the plurality of crowns have to be maintained. Therefore, not only is shape data of each individual crown fitted to the digital reconstruction of each individual tooth, but shape data of a plurality of crowns are also fitted to digital reconstructions of a plurality of teeth. A fitting mechanism to optimize some fitting criteria may be used to perform the fitting of rigid objects to one another. The cue on the position and orientation for fitting may be found from the position and orientation of neighboring teeth and crowns. It should be noted that if the fitting is performed after tooth movements, then each individual crown has to be fitted to the digital reconstruction of the corresponding tooth.

FIG. 5A illustrates a block diagram 250 that shows how position and orientation of roots are determined by acquiring CBCT and intra-oral imagery in a first patient visit, and intra-oral imagery in subsequent patient visits, in accordance with certain embodiments. Certain of the operations shown in FIG. 5A may be performed by the computational device 4, the intra-oral imaging system 6 or by the CBCT imaging system 8.

At a first patient visit 252, a dental practitioner may image a dental arch (e.g., the mandibular and/or the maxillary arch) of the patient's oral cavity, to secure both CBCT imagery 254 and intra-oral imagery 256 of the dental arch of the patient. The CBCT imagery 254 is volumetric imagery that includes low resolution crowns and low resolution roots, whereas the intra-oral imagery 256 may be used to generate shape data that includes high resolution crowns.

In certain embodiments, the shape data with high resolution crowns of the intra-oral imagery 256 is fitted (reference numeral 258) to volumetric representation of the CBCT imagery 254 that is comprised of low resolution crowns and low resolution roots, to generate a digital reconstruction 260 of the whole dental arch, where the digital reconstruction may include low resolution roots 262 and high resolution crowns 264. It may be noted that the digital reconstruction 260 of the whole dental arch, determined by fitting the shape data of the intra-oral scan to the CBCT imagery, is superior in quality to any digital reconstruction of the whole dental arch that may be determined from the CBCT imagery alone. The superior quality is achieved because the high resolution crowns of the intra-oral imagery replace the low resolution crowns of the CBCT imagery in the digital reconstruction 260 of the whole dental arch determined by fitting the shape data of the intra-oral imagery to the CBCT imagery.

The dental practitioner may place braces of other devices that apply forces on the teeth, and the forces cause movements of the teeth (reference numeral 266).

At second and subsequent patient visits (shown via reference numeral 268), intra-oral imagery 270 of the entire dental arch of the patient is acquired, and shape data of the crowns of the dental arch is determined from the intra-oral imagery 270. The root determination application 18 fits the shape data of the crowns of the dental arch (obtained from the intra-oral imagery 270) to the digital reconstruction of the dental arch 260 to determine the position and orientation of roots in the dental arch (shown via reference numeral 272).

It may be noted that once the digital reconstruction includes high resolution crown data, then subsequent crown data acquired by intraoral imaging may be fitted to the high resolution crown data of the digital reconstruction to determine the position and orientation of roots.

FIG. 5B illustrates a block diagram 274 that shows how position and orientation of roots are determined by acquiring CBCT imagery in a first patient visit and intra-oral imagery in subsequent patient visits, in accordance with certain embodiments. Certain of the operations shown in FIG. 5B may be performed by the computational device 4, the intra-oral imaging system 6 or by the CBCT imaging system 8.

At a first patient visit 276, a dental practitioner may image a dental arch (e.g., the mandibular and/or the maxillary arch) of the patient's oral cavity, to secure CBCT imagery 278. The CBCT imagery 278 is volumetric imagery that includes low resolution crowns 282 and low resolution roots 284. The digital reconstruction 280 of the whole dental arch constructed from the CBCT imagery 278 includes the low resolution crowns and the low resolution roots. In embodiments shown in FIG. 5B, the dental practitioner avoids acquiring intra-oral imagery in the first dental visit and saves time and resources. However, the quality of digital reconstruction 280 is inferior as the high resolution crowns of intra-oral imagery are not included in the digital reconstruction 280.

The dental practitioner may place braces of other devices that apply forces on the teeth, and the forces cause movements of the teeth (reference numeral 286).

At second and subsequent patient visits (shown via reference numeral 288), intra-oral imagery 290 of the entire dental arch of the patient is acquired, and shape data of the crowns of the dental arch is determined from the intra-oral imagery 290. The root determination application 18 fits the shape data of the crowns of the dental arch (obtained from the intra-oral imagery 290) to the digital reconstruction of the dental arch 280 to determine the position and orientation of roots in the dental arch (shown via reference numeral 292). The position and orientation of the roots 292 determined in the embodiments described in FIG. 5B may be less accurate that the position and orientation of the roots 272 determined in the embodiments described in FIG. 5A, as the quality of the digital reconstruction 280 is less accurate than the quality of the digital reconstruction 260. However, the dental practitioner saves time and resources by not acquiring intra-oral imagery in the first dental visit.

FIG. 5C illustrates a block diagram 350 that shows how position and orientation of roots are determined in a partial dental arch, in accordance with certain embodiments. Certain of the operations shown in FIG. 5C may be performed by the computational device 4, the intra-oral imaging system 6 or by the CBCT imaging system 8.

At a first patient visit 352, a dental practitioner may image the entirety of the dental arches (i.e., both the mandibular and the maxillary arch) of the patient's oral cavity, to secure the CBCT imagery 354.

In certain embodiments, the dental practitioner may determine that only a partial dental arch is of interest to the dental practitioner. In such embodiments, the dental practitioner may acquire intra-oral imagery 356 of the partial dental arch of the patient. Acquiring intra-oral imagery of the partial dental arch may be less time consuming and less resource intensive than acquiring intra-oral imagery of the whole dental arch.

The CBCT imagery 354 is volumetric imagery that includes low resolution crowns and low resolution roots of the entire dental arch. The intra-oral imagery 356 may be used to generate shape data that includes high resolution crowns of the partial dental arch.

In certain embodiments, the shape data with high resolution crowns of the partial dental arch of the intra-oral imagery 356 is fitted (reference numeral 358) to a volumetric representation of the CBCT imagery 354 that is comprised of low resolution crowns and low resolution roots of the whole dental arch, to generate a digital reconstruction 360 of the partial dental arch, where the digital reconstruction of the partial dental arch may include low resolution roots 362 and high resolution crowns 364.

The dental practitioner may place braces of other devices that apply forces on the teeth, and the forces cause movements of the teeth (reference numeral 366).

At second and subsequent patient visits (shown via reference numeral 368), intra-oral imagery 370 of the partial dental arch of the patient is acquired, and shape data of the crowns of the partial dental arch is determined from the intra-oral imagery 370. The root determination application 18 fits the shape data of the crowns of the partial dental arch (obtained from the intra-oral imagery 370) to the digital reconstruction of the partial dental arch 360 to determine the position and orientation of roots in the partial dental arch (shown via reference numeral 372).

FIG. 5D illustrates a block diagram 66 that shows how position and orientation of roots are determined in a plurality of patient visits, in accordance with certain embodiments. Certain of the operations shown in FIG. 5D may be performed by the computational device 4, the intra-oral imaging system 6 or by the CBCT imaging system 8.

At a first patient visit 68 a dental practitioner may determine image the patient's oral cavity to secure volumetric imagery 70, a sequence of X-Ray images 72, Intra-Oral imagery 74, etc. In some embodiments the digital reconstruction 76 of tooth or a plurality of teeth may be performed by combining (reference numeral 78) multiple types of imagery. In other embodiments, the volumetric imagery, such as the CBCT imagery 70, by itself is adequate for the digital reconstruction of teeth. The digital reconstruction of teeth 76 may include crowns 80 and roots 82.

The dental practitioner may place braces of other devices that apply forces on the teeth, and the forces cause movements of the teeth (reference numeral 84).

At second and subsequent patient visits (shown via reference numeral 86) intra-oral imagery 88 of the oral cavity of the patient is taken, and shape data of crowns 90 is determined from the intra-oral imagery. The root determination application 18 fits the shape data of the plurality of crowns 90 to the digital reconstruction of the plurality of teeth 76 to determine the position and orientation of a plurality of roots 92 at the second and subsequent patient visits, where at each subsequent patient visit there is a potential for movement of teeth.

Figure 6A:
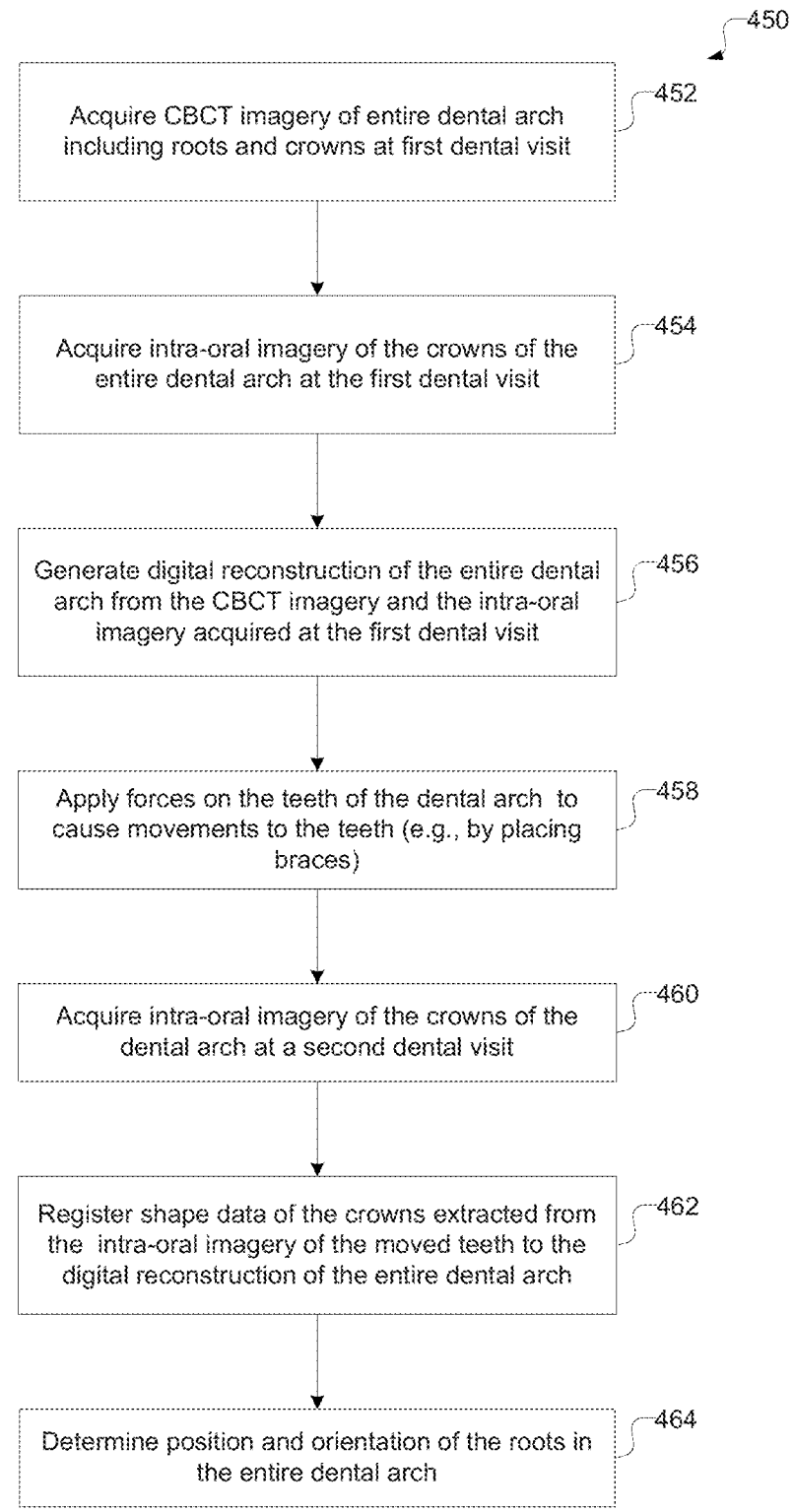
FIG. 6A illustrates a flowchart that shows how position and orientation of roots are determined by acquiring CBCT and intra-oral imagery in a first patient visit, and intra-oral imagery in subsequent patient visits, in accordance with certain embodiments.

FIG. 6A illustrates a flowchart 450 that shows how position and orientation of roots are determined by acquiring CBCT and intra-oral imagery in a first patient visit, and intra-oral imagery in subsequent patient visits, in accordance with certain embodiments. Certain of the operations shown in FIG. 6A may be performed by the computational device 4, the intra-oral imaging system 6, or by the CBCT imaging system 8.

Control starts at block 452, in which CBCT imagery of the entire dental arch is acquired at first dental visit, where the CBCT imagery includes both roots and crowns. Control proceeds to block 454 in which intra-oral imagery of the crowns of the entire dental arch are also acquired at the first dental visit. Therefore, both the CBCT imagery and the intra-oral imagery are determined with the same position and orientation of the teeth of the dental arch.

A digital reconstruction of the entire dental arch is constructed (at block 456) from the CBCT imagery and the intra-oral imagery acquired at the first dental visit. Forces are applied (at block 458) on the teeth of the dental arch to cause movements to the teeth (e.g., by placing braces). Control proceeds to block 460, in which intra-oral imagery of the crowns of the dental arch at acquired during a second dental visit. Shape data of the crowns extracted from the intra-oral imagery of the moved teeth is registered (at block 462) to the digital reconstruction of the entire dental arch, to determine (at block 464) the position and orientation of the roots in the entire dental arch.

Figure 6B:
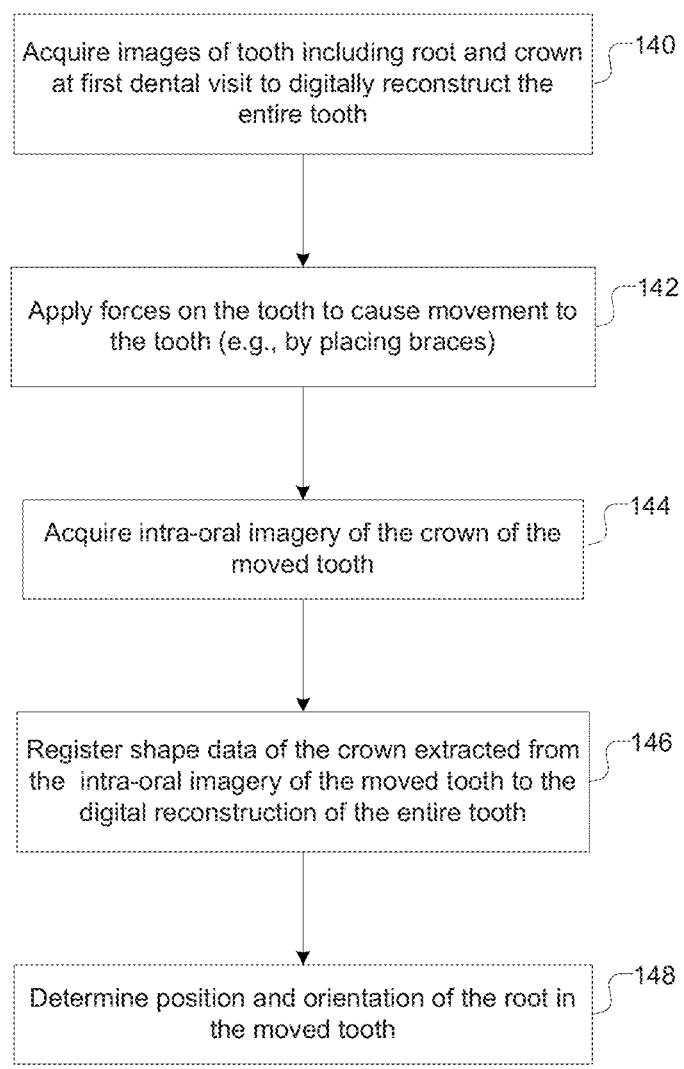
FIG. 6B illustrates a flowchart that shows how position and orientation of roots are determined by acquiring CBCT imagery in a first patient visit and intra-oral imagery in subsequent patient visits, in accordance with certain embodiments.

FIG. 6B illustrates a flowchart that shows how position and orientation of roots are determined by acquiring CBCT imagery in a first patient visit and intra-oral imagery in subsequent patient visits, in accordance with certain embodiments. Certain of the operations shown in FIG. 6B may be performed by the computational device 4, the intra-oral imaging system 6, or by the CBCT imaging system 8.

Control starts at block 140, in which a CBCT imaging system 8 acquires images of a tooth (including root and crown) at first dental visit to digitally reconstruct the entire tooth. Instead of a single tooth a plurality of teeth may be imaged to digitally reconstruct the plurality of teeth. Forces are applied (at block 142) on the tooth to cause movement to the tooth (e.g., by placing braces). Intra-oral imagery of the crown of the moved tooth is acquired (at block 144). Shape data of the crown extracted from the intra-oral imagery of the moved tooth is registered (at block 146) to the digital reconstruction of the entire tooth, and the position and orientation of the root in the moved tooth is determined (at block 148).

FIG. 7 illustrates a diagram 150 that shows how shape data of crowns acquired at two different visits are registered to each other to extract root in digital reconstruction of teeth, in accordance with certain embodiments. Certain of the operations shown in FIG. 7 may be performed by the computational device 4, the intra-oral imaging system 6, or by the CBCT imaging system 8.

A first image that may be a CBCT image is acquired by imaging a patient's teeth (at block 152) and digital reconstruction of teeth is performed (at block 154). The digital reconstruction has crowns and roots at relatively low resolution, because reconstruction from CBCT images is at a lower resolution than the resolution of shape data obtained from intra-oral images.

A second image that may be an intra-oral image is acquired by imaging a patient's teeth (at block 156) and first shape data 158 of crowns are determined at a resolution that is higher than the resolution of the digital reconstruction of teeth from CBCT images.

A third image that may be an intra-oral image is acquired by imaging a patient's teeth (at block 160) and second shape data 162 of crowns are determined at a resolution that is higher than the resolution of the digital reconstruction of teeth from CBCT images.

Roots are determined by registering the first shape data 158 of crowns with the second shape data 162 of crowns in the digital reconstruction 154. The registration of the second shape data 162 to the first shape data 158 may be performed with a greater degree of accuracy because of the higher resolution of the shape data in comparison with the digital reconstruction of teeth from CBCT imagery. As a result, the roots may be determined with greater accuracy (in block 154). An iterative mechanism for securing the best fit may be performed during registration. The fitting of shape data of a plurality of crowns acquired at different times to each other further improves the accuracy of the fitting, and provides better accuracy in root determination.

FIG. 8 illustrates a flowchart that shows how position and orientation of a root are determined, in accordance with certain embodiments. Certain of the operations shown in FIG. 8 may be performed by the computational device 4, the intra-oral imaging system 6, or by the CBCT imaging system 8.

Control starts at block 166, in which a digital reconstruction of a tooth from a first image is performed, wherein the tooth includes a crown and a root. An intra-oral imaging sensor 26 acquires (at block 168) a second image of the crown of the tooth, subsequent to a movement of the tooth.

The shape data of the crown extracted from the second image is registered (at block 170) to the digital reconstruction of the tooth from the first image, and a position and an orientation of the root of the tooth is determined (at block 172).

Figure 9:
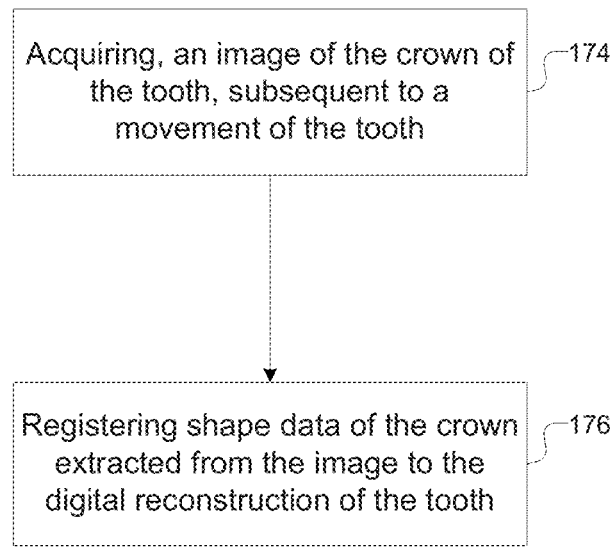
FIG. 9 illustrates a flowchart that shows how position and orientation of a root are determined, in accordance with certain embodiments.

FIG. 9 illustrates a flowchart that shows how position and orientation of a root are determined, in accordance with certain embodiments. Certain of the operations shown in FIG. 9 may be performed by the computational device 4, the intra-oral imaging system 6, or by the CBCT imaging system 8.

Control starts at block 174 in which an image of the crown of the tooth is acquired, subsequent to a movement of the tooth. Shape data of the crown extracted from the image is registered (at block 176) to the digital reconstruction of the tooth.

It may be noted that in FIG. 9 the acquiring of the image and the registering may be performed by the computational device 4. The image may be acquired over a network 22, via a storage medium read by the computational device 4, or via other mechanisms.

The acquiring of the image and the registering may also be performed in the intra-oral imaging system 6. In such embodiments, the intra-oral imaging system 6 receives the digital reconstruction of the teeth via the network 22, via a storage medium, or via other mechanisms.

The acquiring of the image and the registering may also be performed in the CBCT imaging system 8. In such embodiments, the CBCT imaging system 8 acquires the image by receiving the image of the crown via the network 22, via a storage medium, or via other mechanisms.

Figure 10:
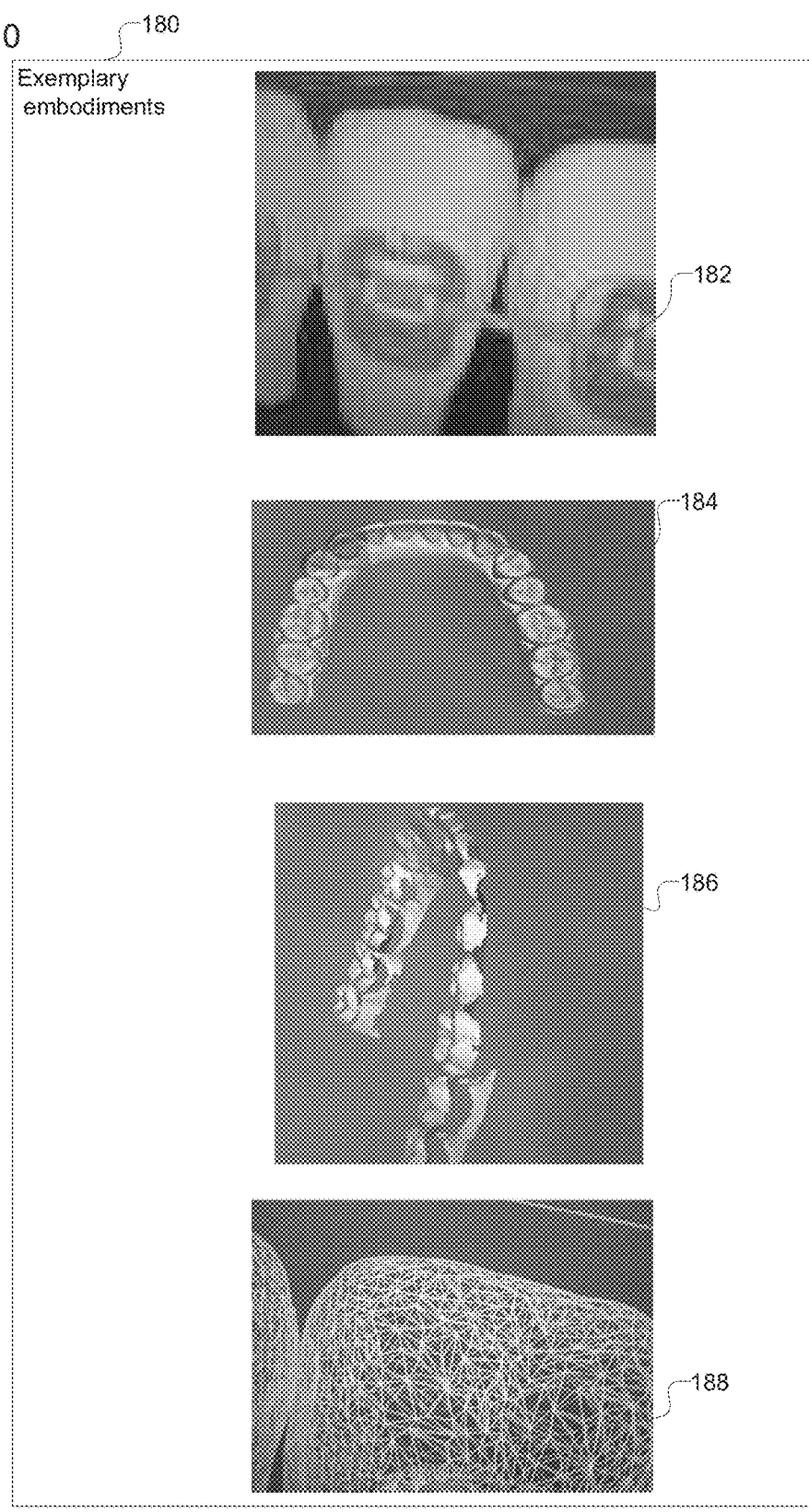
FIG. 10 illustrates braces on a teeth and determination of shape from intra-oral imagery, in accordance with certain embodiments.

FIG. 10 illustrates exemplary embodiments 180 of braces on a teeth and determination of shape from intra-oral imagery. Exemplary braces that apply forces on teeth for movement of teeth are shown via reference numeral 182. Shape data obtained from intra-oral imagery from various viewpoints is shown via reference numeral 184, 186. A tessellated representation of the shape data is shown via reference numeral 188. Other ways of applying forces to teeth or other ways of representing shape data may be implemented in alternative embodiments.

Figure 11:
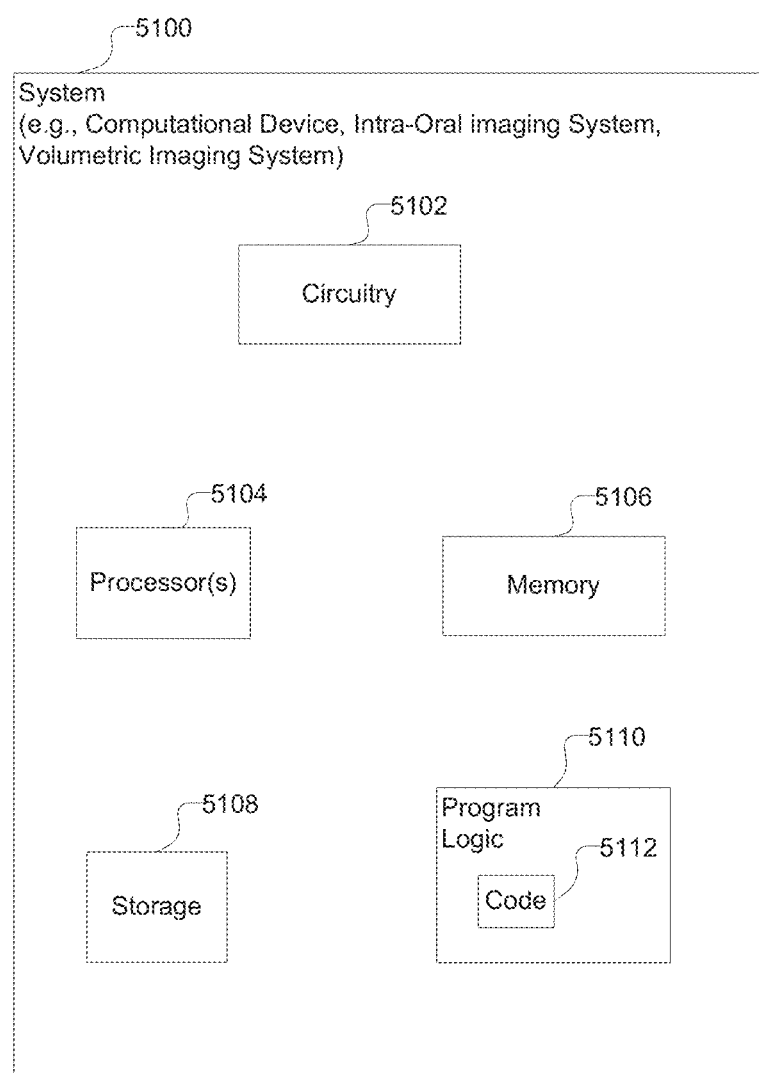
FIG. 11 illustrates a block diagram of a system that shows certain elements of the computational device, intra-oral imaging system, or the CBCT imaging system shown in FIG. 1, in accordance with certain embodiments.

FIG. 11 illustrates a block diagram that shows certain elements that may be included in a system 5100, where in the system may be the computational device 4, the intra-oral imaging system 6 or the CBCT imaging system 8, in accordance with certain embodiments. The system 5100 may include a circuitry 5102 that may in certain embodiments include at least a processor 5104. The processor 5104 may comprise any suitable processor known in the art, such as, an arithmetic logical unit, a central processing unit, a circuitry that perform operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 5104. The system 5100 may also include a memory 5106 (e.g., a volatile memory device), and storage 5108. The storage 5108 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 5108 may comprise an internal storage device, an attached storage device and/or a network accessible storage device. The system 5100 may include a program logic 5110 including code 5112 that may be loaded into the memory 5106 and executed by the processor 5104 or circuitry 5102. In certain embodiments, the program logic 5110 including code 5112 may be stored in the storage 5108. In certain other embodiments, the program logic 5110 may be implemented in the circuitry 5102. Therefore, while FIG. 51 shows the program logic 5110 separately from the other elements, the program logic 5110 may be implemented in the memory 5106 and/or the circuitry 5102.

Therefore, FIGS. 1-11 illustrate certain embodiments in which roots are determined by fitting shape data obtained from intra-oral imagery to digital reconstruction of teeth obtained at least from CBCT imagery. The usage of the intra-oral imagery reduces the amount of radiation on the patient when root determination is desired at multiple patient visits.

Intra-oral Imagery, CBCT Imagery, and Model Data

Generally intra-oral images are of a significantly higher precision in comparison to CBCT images. Furthermore, CBCT data can be noisy. Also, the use of CBCT results in ionizing radiation to the patient and it is best to use CBCT systems with as little radiation as possible.

In certain embodiments, a computational device receives shape data of a patient's crown and volumetric imagery of the patient's tooth. The shape data may be generated from intra-oral images and may correspond to the surface data of the patient's crown. The volumetric imagery may comprise CBCT imagery or other types of volumetric imagery. A determination is made of voxels that represent one or more crowns in the shape data. The voxels in the shape data are registered with corresponding voxels of the volumetric imagery.

In certain embodiments, segmented crowns determined from intra-oral imagery are registered to voxels CBCT images. This allows more accurate determination of the boundary between the crown and the root of a tooth in the CBCT data. It may be noted that without the use of the intra-oral imagery the boundary between the crown and the root of a tooth may be fuzzy (i.e., not clear or indistinct) in CBCT imagery.

In certain embodiments, the surface scan data of an intra-oral imaging system is registered to the volumetric data obtained from a CBCT system. The 3-D coordinates of the crown boundaries that are found in the intra-oral imagery are mapped to the voxels of the CBCT imagery to determine the boundary between roots and crowns at a sub-voxel levels of accuracy in the CBCT imagery. As a result, the roots can be extracted, even from noisy CBCT scan data. In additional embodiments, holes in intra-oral imagery may be filled in by integrating CBCT imagery with intra-oral imagery.

In certain embodiments, an orientation of a patient's tooth is determined from shape data of the patient's crown and volumetric imagery of the patient's tooth. A computational device is used to register the shape data of the patient's crown with model data, based on the determined orientation of the patient's tooth. In additional embodiments, the orientation of the patient's tooth corresponds to a longitudinal direction of the patient's tooth. The longitudinal direction of the patient's tooth is determined based on tooth shape determined by registering the shape data to the volumetric imagery. The model data is selected from a repository that stores a plurality of models corresponding to representative roots or representative teeth. The model data is rotated, translated, and morphed to conform to the determined orientation to register the shape data of the patient's crown with the model data to generate an esthetically appealing tooth.

Integration of Surface Data and Volumetric Data

Figure 12:
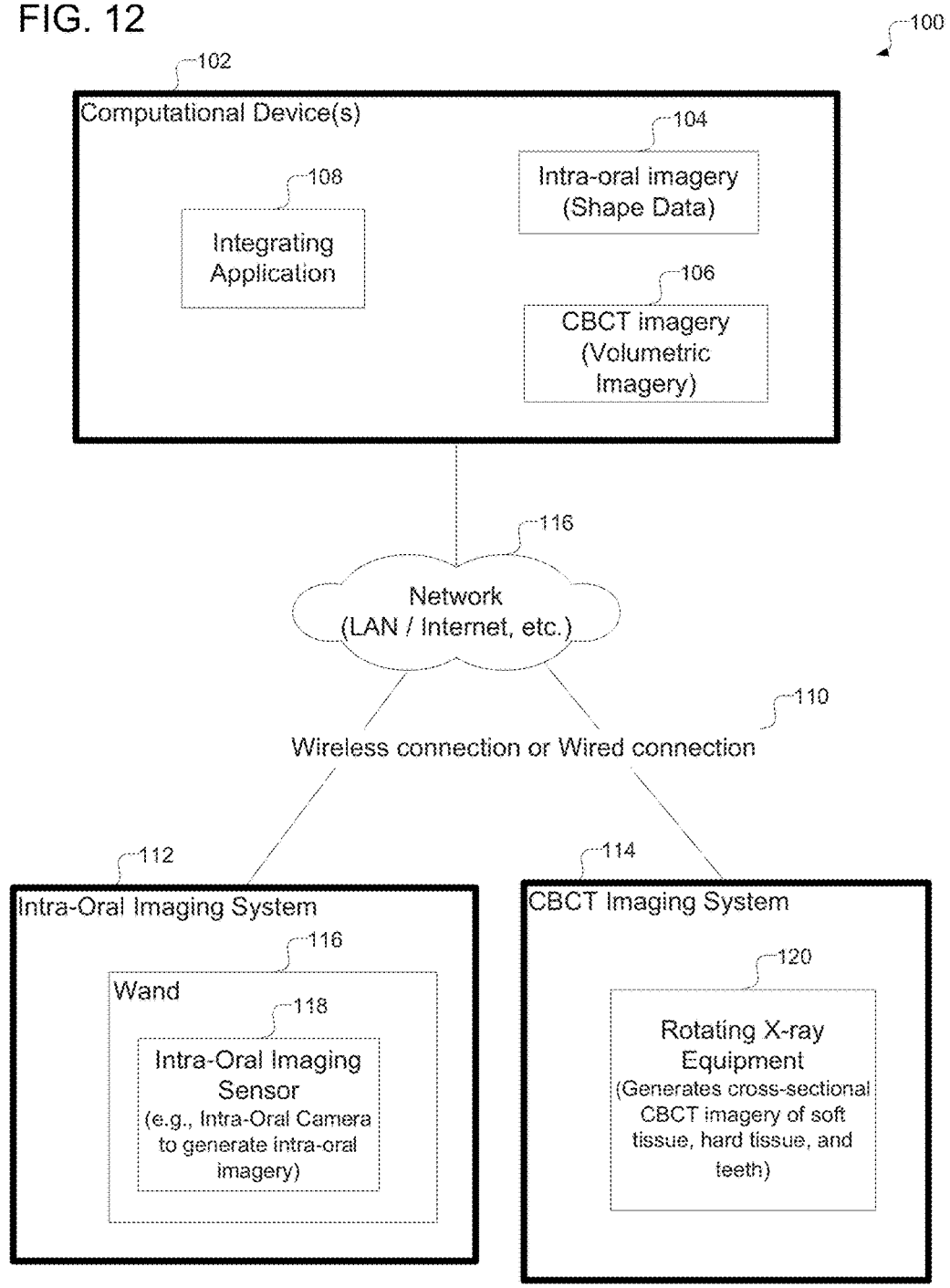
FIG. 12 illustrates a block diagram of a computing and imaging environment that includes a computational device that integrates intra-oral imagery and volumetric imagery, such as CBCT imagery, in accordance with certain embodiments.

FIG. 12 illustrates a block diagram of a computing and imaging environment 100 that includes a computational device 102 that integrates intra-oral imagery 104 and CBCT imagery 106, in accordance with certain embodiments. The computational device 102 may include any suitable computational device such as a personal computer, a server computer, a mini computer, a mainframe computer, a blade computer, a tablet computer, a touch screen computing device, a telephony device, a cell phone, a mobile computational device, a dental equipment having a processor, etc., and in certain embodiments the computational device 102 may provide web services or cloud computing services. In certain alternative embodiments, more than one computational device may be used for storing data or performing the operations performed by the computational device 102.

The intra-oral imagery 104 provides surface data of a patient's crown and the CBCT imagery 106 provides volumetric imagery of a patient's tooth, where the tooth may include both the crown and the root. In alternative embodiments, the surface data of the patient's crown may be provided by imagery that is different from intra-oral imagery, and the volumetric imagery may be provided by other types of tomographic imagery, ultrasonic imagery, magnetic resonance imagery (MRI), etc. The volumetric imagery comprises three dimensional imagery and may be represented via voxels.

The computational device 102 may include an integrating application 108, implemented in certain embodiments in software, hardware, firmware or any combination thereof. The integrating application 108 integrates the intra-oral imagery 104 and the CBCT imagery 106 to provide additional functionalities that are not found in either the intra-oral imagery 104 or the CBCT imagery 106 when they are not integrated.

The computational device 102 is coupled via one or more wired or wireless connections 110 to an intra-oral imaging system 112 and a CBCT imaging system 114, over a network 116. In certain embodiments, the network 116 may comprise a local area network, the Internet, and intranet, a storage area network, or any other suitable network.

The intra-oral imaging system 112 may include a wand 116 having an intra-oral imaging sensor 118, where in certain embodiments the intra-oral imaging sensor 118 is an intra-oral camera that generates intra-oral imagery of the oral cavity of a patient. The CBCT imaging system 114 may include a rotating X-ray equipment 120 that generates cross-sectional CBCT imagery of the soft tissue, hard tissue, teeth, etc. of a patient.

Therefore, FIG. 12 illustrates certain embodiments in which an integrating application 108 that executes in the computational device 102 integrates intra-oral imagery 104 generated by an intra-oral imaging system 112 with CBCT imagery 106 generated by a CBCT imaging system 114. In certain additional embodiments, the intra-oral imagery 104 and the CBCT imagery 106 may be stored in a storage medium (e.g., a disk drive, a floppy drive, a pen drive, a solid state device, an optical drive, etc.), and the storage medium may be coupled to the computational device 102 for reading and processing by the integrating application 108.

Figure 13:
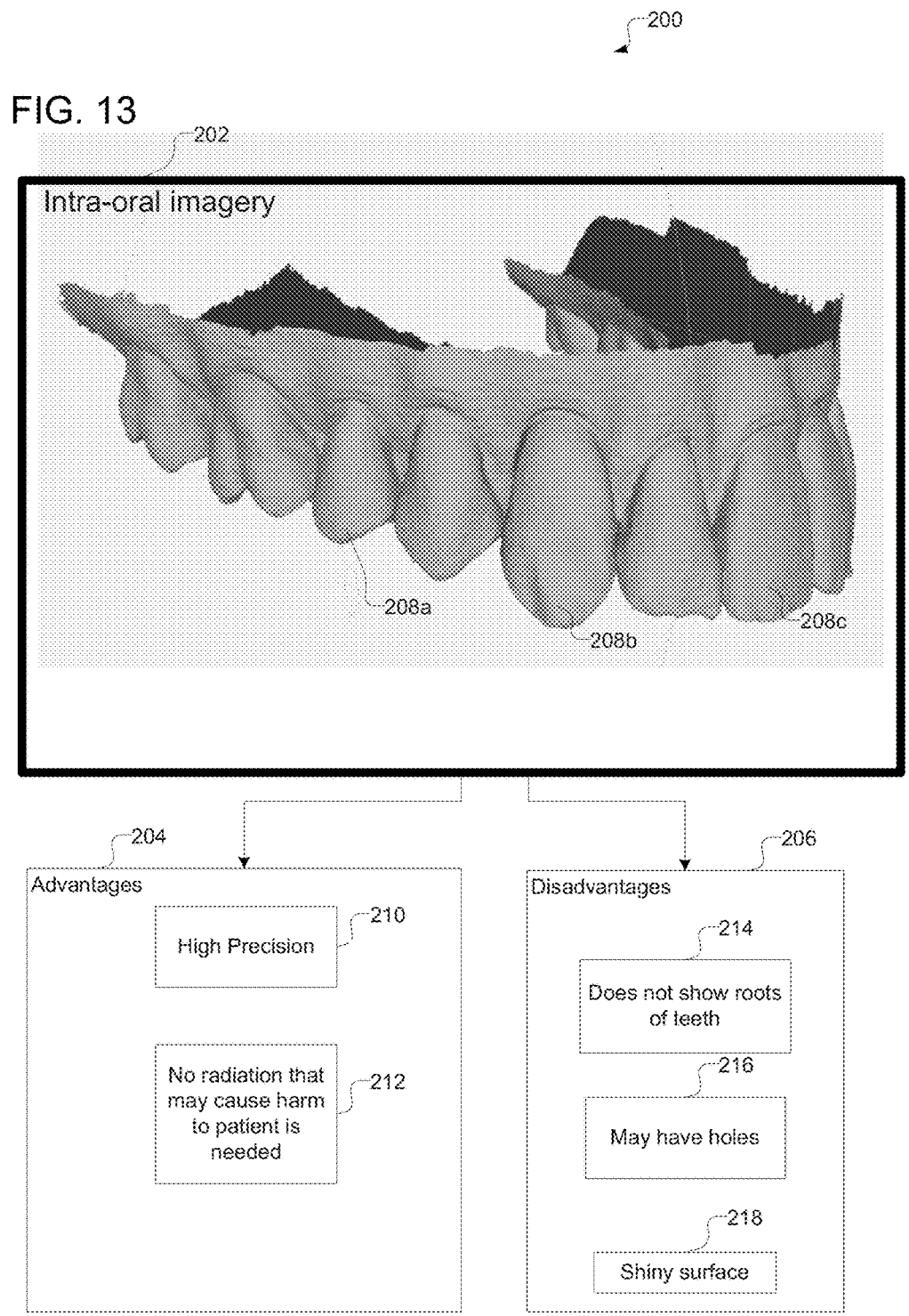
FIG. 13 illustrates a diagram in which an exemplary intra-oral imagery and advantages and disadvantages of intra-oral imagery are shown, in accordance with certain embodiments.

FIG. 13 illustrates a diagram 200 in which an exemplary intra-oral imagery 202 is shown, in accordance with certain embodiments. Certain exemplary advantages 204 and certain exemplary disadvantages 206 of the intra-oral imagery 202 are also shown, in accordance with certain embodiments.

The intra-oral imagery 206 shows exemplary crowns (e.g., crowns 208a, 208b, 208c) in the upper arch of the oral cavity of a patient, where the intra-oral imagery 206 may have been acquired via the intra-oral imaging system 112. The crown is the portion of the tooth that may be visually seen, and the root is the portion of the tooth that is hidden under the gum.

FIG. 13 shows that the intra-oral imagery is typically of a high precision 210 in comparison with CBCT imagery. Additionally, no radiation that may cause harm to the patient (shown via reference numeral 212) is needed in acquiring the intra-oral imagery 202. However, the intra-oral imagery 202 does not show the roots of teeth (reference numeral 214) and may have holes 216, where a hole is a portion of the tooth that is not visible in intra-oral imagery. Holes may arise because of malocclusions or for other reasons. While, small and medium sized holes may be filled (i.e. the hole is substituted via a simulated surface generated programmatically via the computational device 102) by analyzing the intra-oral imagery 202, larger holes (i.e. holes that exceed certain dimensions) may not be filled by just using data found in intra-oral imagery. Additionally, shiny surfaces f crowns may generate poor quality intra-oral imagery (reference numeral 218).

Therefore, FIG. 13 illustrates certain embodiments in which intra-oral imagery may have holes and do not show the entirety of the roots of teeth.

Figure 14:
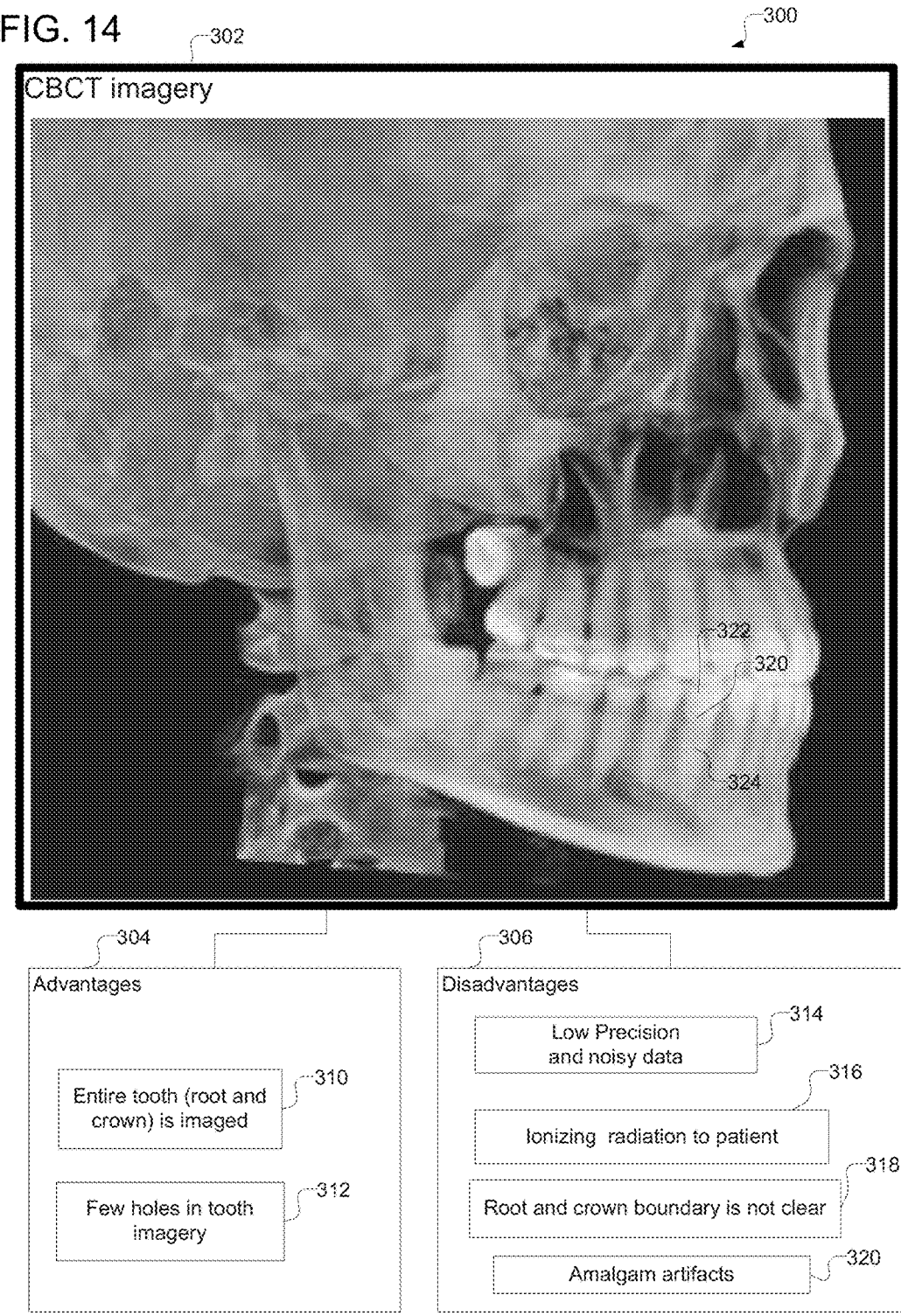
FIG. 14 illustrates a diagram in which an exemplary CBCT imagery and advantages and disadvantages of CBCT are shown, in accordance with certain embodiments.

FIG. 14 illustrates a diagram 300 in which an exemplary CBCT imagery 302, and certain advantages 304 and certain disadvantages 306 of CBCT imagery are shown, in accordance with certain embodiments.

In the CBCT imagery the entire tooth (i.e., the root and the crown) is imaged (reference number 310) and there are few holes (reference number 312). The few holes that exist may be caused by artifacts as a result of amalgam fillings on tooth (reference numeral 320). However, the CBCT images may be of a lower precision and may be more noisy in comparison to intra-oral imagery (reference numeral 314). There is a potential for ionizing radiation to the patient in the acquisition of CBCT imagery (reference numeral 316) unlike in intra-oral imagery in which there is no ionizing radiation in the acquisition process. Furthermore, while the complete tooth is imaged in CBCT imagery, the boundary between the root and the crown may not be clear (reference numeral 318) as may be seen (reference numeral 320) in the exemplary CBCT imagery 302. The fuzzy and indistinct boundary 320 between the crown 322 and the root 324 may be caused by varying radiodensities during the process of acquiring CBCT images. In certain embodiments, motion of the patient may generate inferior quality CBCT imagery.

Therefore, FIG. 14 illustrates certain embodiments in which CBCT images may have low precision and have noisy data with the boundary between the root and crown not being clearly demarcated.

Figure 15:
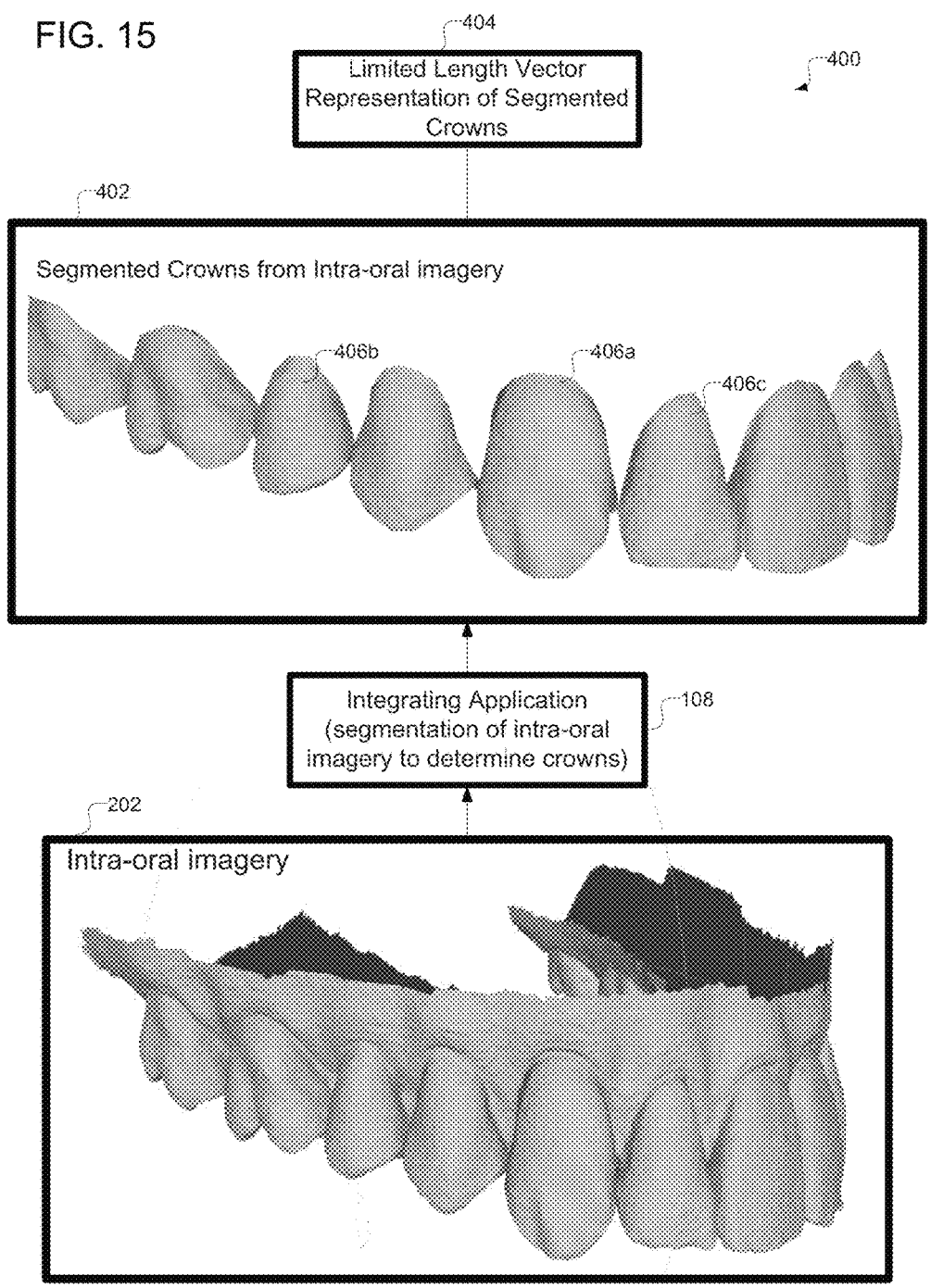
FIG. 15 illustrates a diagram that shows how an intra-oral imagery is segmented to determine crowns represented via limited length vectors, in accordance with certain embodiments.

FIG. 15 illustrates a diagram 400 that shows how an intra-oral imagery 202 is segmented to determine crowns 402 represented via limited length vectors 404, in accordance with certain embodiments. The segmentation of the intra-oral imagery 202 to determine crowns 402 may be performed via the integrating application 108 that executes in the computational device 102. Exemplary segmented crowns are shown via reference numerals 406a, 406b, 406c. The segmented crowns are of a high resolution and show clearly defined edges and are represented via limited length vectors 404. A vector has a direction and magnitude in three-dimensional space. A limited length vector is a vector whose length is limited. In other embodiments, the segmented crowns may be represented via data structures or mathematical representations that are different from limited length vectors 404.

Therefore, FIG. 15 illustrates certain embodiments in which intra-oral imagery is segmented to determine crowns represented via, limited length vectors.

Figure 16:
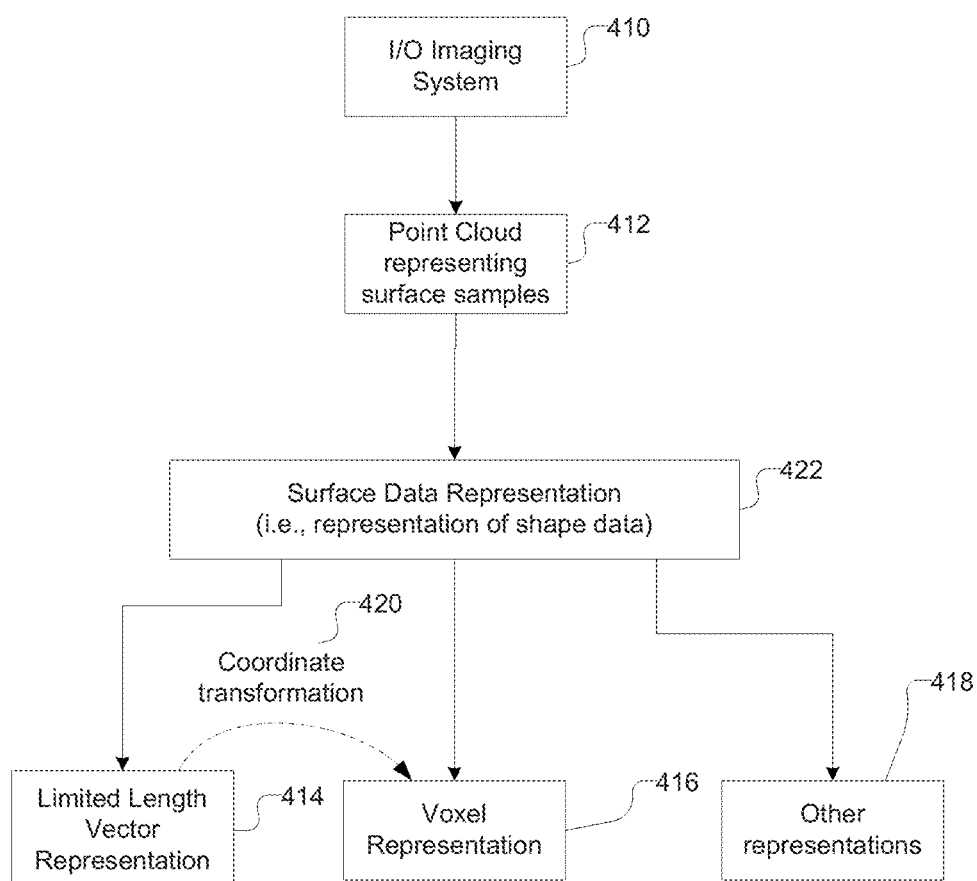
FIG. 16 illustrates a diagram that shows how the surface data obtained via intra-oral imagery may be represented via limited length vectors or voxels, in accordance with certain embodiments.

FIG. 16 illustrates a diagram that shows how an intra-oral imaging system 410 scans the inside of a patient's mouth and generates surface samples of the crowns of a patient's teeth, where the aggregated surface samples may be referred to as a point cloud 412.

The point cloud 412 may processed by the integrating application 108 executing the computational device 102 to represent the surface of the crowns. The crown of the tooth is a solid object, and the surfaces of the crown correspond to the boundaries of the solid object. The crown surface may be represented by a surface mesh of node points connected by triangles, quadrilaterals or via different types of polygon meshes. In alternative embodiments, a solid mesh may also be used to represent the crown surface. The process of creating the mesh is referred to as tessellation.

In certain embodiments, the surface corresponding to the crown is represented in three dimensional space via limited length vectors 414 or via voxels 416 or via other data structures 418. The voxels 416 correspond to three-dimensional points on the surface of a crown. In certain embodiments, the limited length vectors 414 may be converted to voxel representation via appropriate three dimensional coordinate transformations 420. The limited length vectors 414 may correspond to the sides of the different types of polygon meshes (e.g., triangles, quadrilaterals, etc.) in the surface representation of the crown.

Therefore, FIG. 16 illustrates certain embodiments in which intra-oral imagery is processed to determine crowns represented via limited length vectors or via voxels. The limited length vectors or voxels correspond to a surface data representation 422 of the crown. Surface data may also be referred to as shape data.

Figure 17:
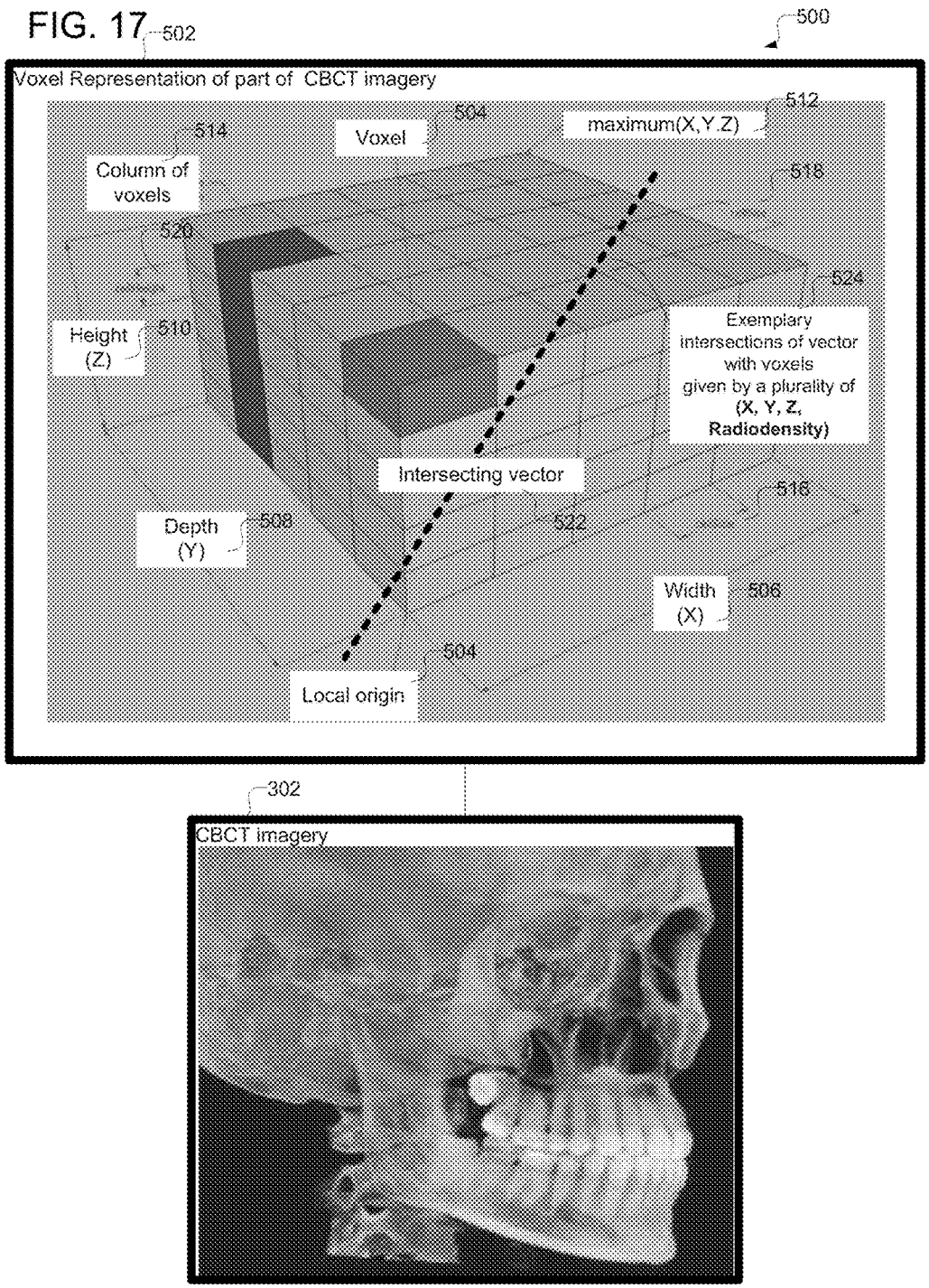
FIG. 17 illustrates a diagram that shows how voxels represent CBCT imagery, in accordance with certain embodiments.

FIG. 17 illustrates a diagram 500 that shows how voxels 502 represent CBCT imagery 302, in accordance with certain embodiments. A voxel (e.g., voxel 504) is a volumetric pixel that is a digital representation of radiodensity in a volumetric framework corresponding to the CBCT imagery 302. The radiodensity may be measured in the Hounsfield scale. In FIG. 17 an exemplary voxel representation 502 of part of the CBCT imagery 302 is shown, The voxel representation 502 has a local origin 504, with X, Y, Z coordinates representing width, depth, and height respectively (shown via reference numerals 506, 508, 510). The coordinate of the voxel where the X, Y, Z values are maximum are shown via the reference numeral 512. An exemplary voxel 504 and an illustrative column of voxels 514 are also shown. Each voxel has a volume defined by the dimensions shown via reference numerals 516, 518, 520.

In certain embodiments, limited length vectors of intra-oral imagery are registered to the voxel representation of the CBCT imagery, to determine where the limited length vectors intersect the voxels of the CBCT imagery. In an exemplary embodiments, an intersecting limited length vector 522 is shown to intersect the voxels of the CBCT imagery at various voxels, wherein at least one voxel 524 at which the intersection takes place has a volumetric coordinate of (X,Y,Z) with an associated radiodensity.

Therefore, FIG. 17 illustrates certain embodiments in which CBCT imagery is represented via voxels. The limited length vectors of the intra-oral imagery intersects the voxels of the CBCT imagery when both are placed in the same coordinate system, wherein each intersection has a X,Y,Z, coordinate and a radiodensity. In certain embodiments, the limited length vectors may be one or more of the sides of triangulated tessellations used to represent shape data. The limited length vectors may be chained in shape representations.

Figure 18:
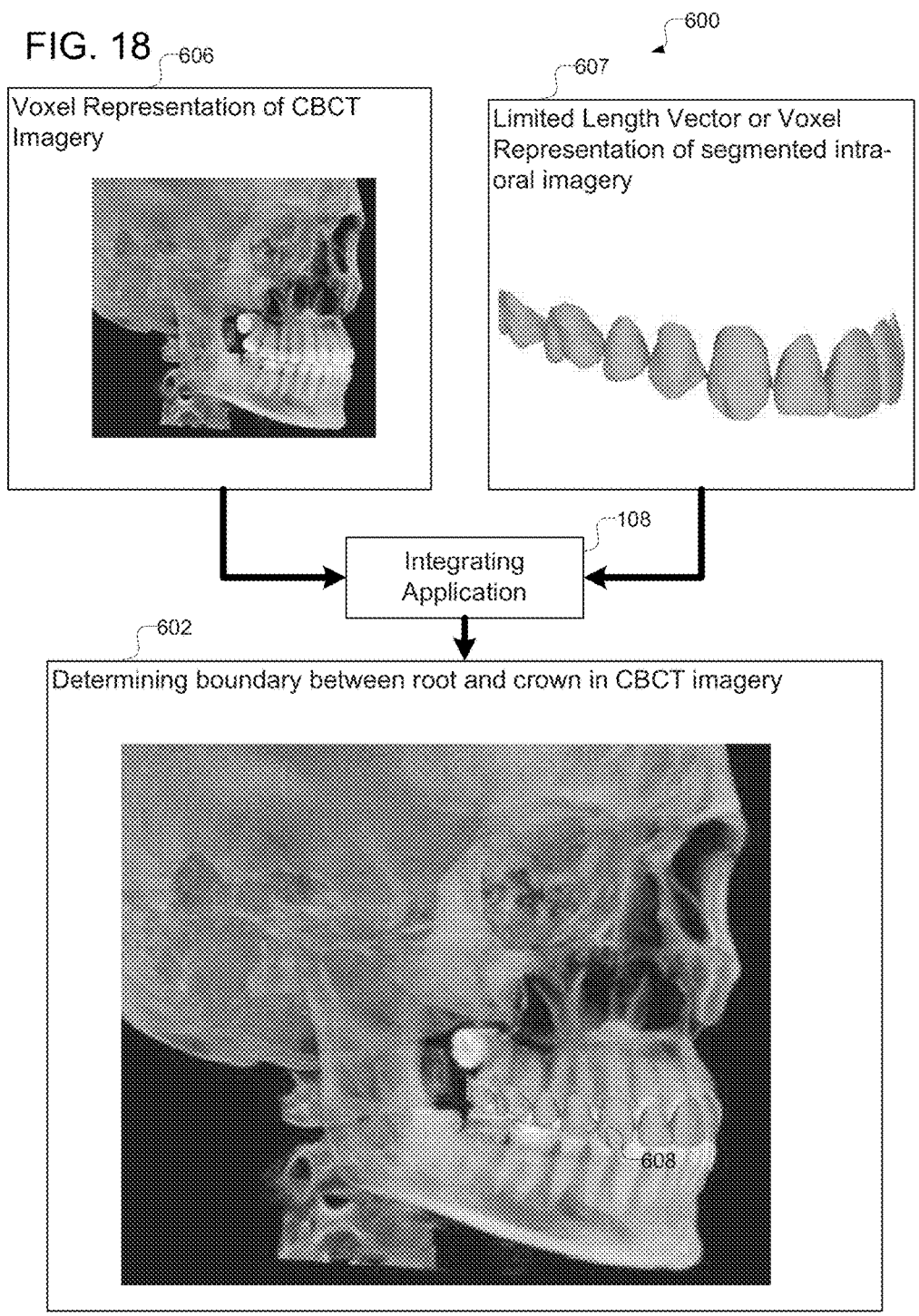
FIG. 18 illustrates a diagram that shows how the boundary between root and crown is determined in CBCT imagery by integrating intra-oral imagery with CBCT imagery, in accordance with certain embodiments.

FIG. 18 illustrates a diagram 600 that shows how the boundary between root and crown is determined in CBCT imagery by integrating intra-oral imagery with CBCT imagery, in accordance with certain embodiments. In certain embodiments, the voxel representation 606 of CBCT imagery is integrated (via the integrating application 108) with the limited length vector representation or voxel representation 607 of the intra-oral imagery to overlay the high resolution clearly segmented crowns of the intra-oral imagery on the low resolution fuzzy crowns of the CBCT imagery (as shown via reference numeral 608), to clearly demarcate the boundary between roots and crowns in the CBCT imagery 602. In certain embodiments the integration CBCT imagery and intra-oral imagery results in a type of filtration operation that sharpens the CBCT imagery to determine the boundary between roots and crowns.

Therefore, FIG. 18 illustrates certain embodiments in which CBCT imagery is augmented with data from intra-oral imagery to determine the boundary between roots and crowns with a greater degree of accuracy in comparison to using the CBCT imagery alone. As a result of the augmentation, high precision crowns and low precision roots are obtained.

Figure 19:
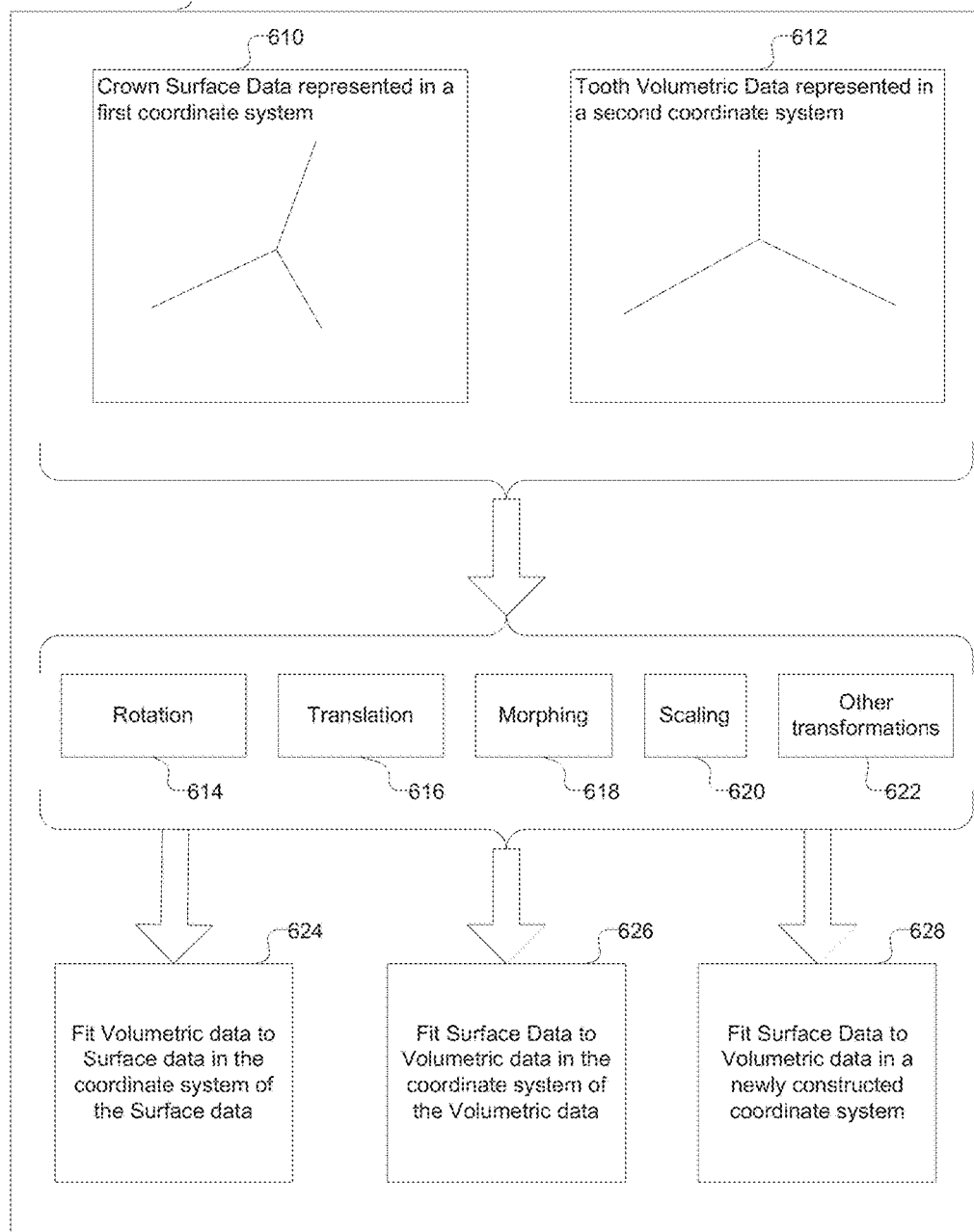
FIG. 19 illustrates a diagram that shows how surface data and volumetric data are fitted to each other, in accordance with certain embodiments.

FIG. 19 illustrates a diagram 609 that shows how surface data and volumetric data are fitted to each other, in accordance with certain embodiments. In certain embodiments, the surface data (i.e., the crown surface data) may be represented with reference to a first coordinate system (shown via reference numeral 610) The volumetric data that represents the tooth may be represented in a second coordinate system (shown via reference numeral 612).

In certain embodiments one or both of the crown surface data and the tooth volumetric data may have to be rotated 614, translated 616, morphed 618, scaled 620, or made to undergo other transformations 622 to appropriately overlap the crown surface data and the tooth volumetric data in a single unified coordinate system. For example, in certain embodiments the tooth volumetric data is fitted to the crown surface data in the coordinate system of the tooth surface data by appropriate rotations, translations, morphing, scaling, etc., of the tooth volumetric data (as shown via reference numeral 624). In other embodiments, crown surface data is fitted to the tooth volumetric data in the coordinate system of the tooth volumetric data by appropriate rotations, translations, morphing, scaling, etc., of the crown surface data (as shown via, reference numeral 626). In other embodiments, both the crown surface data and the tooth volumetric data may undergo rotations, translations, morphing, scaling, etc. to fit the crown surface data and tooth volumetric data in a new coordinate system (as shown via reference numeral 628).

Figure 20:
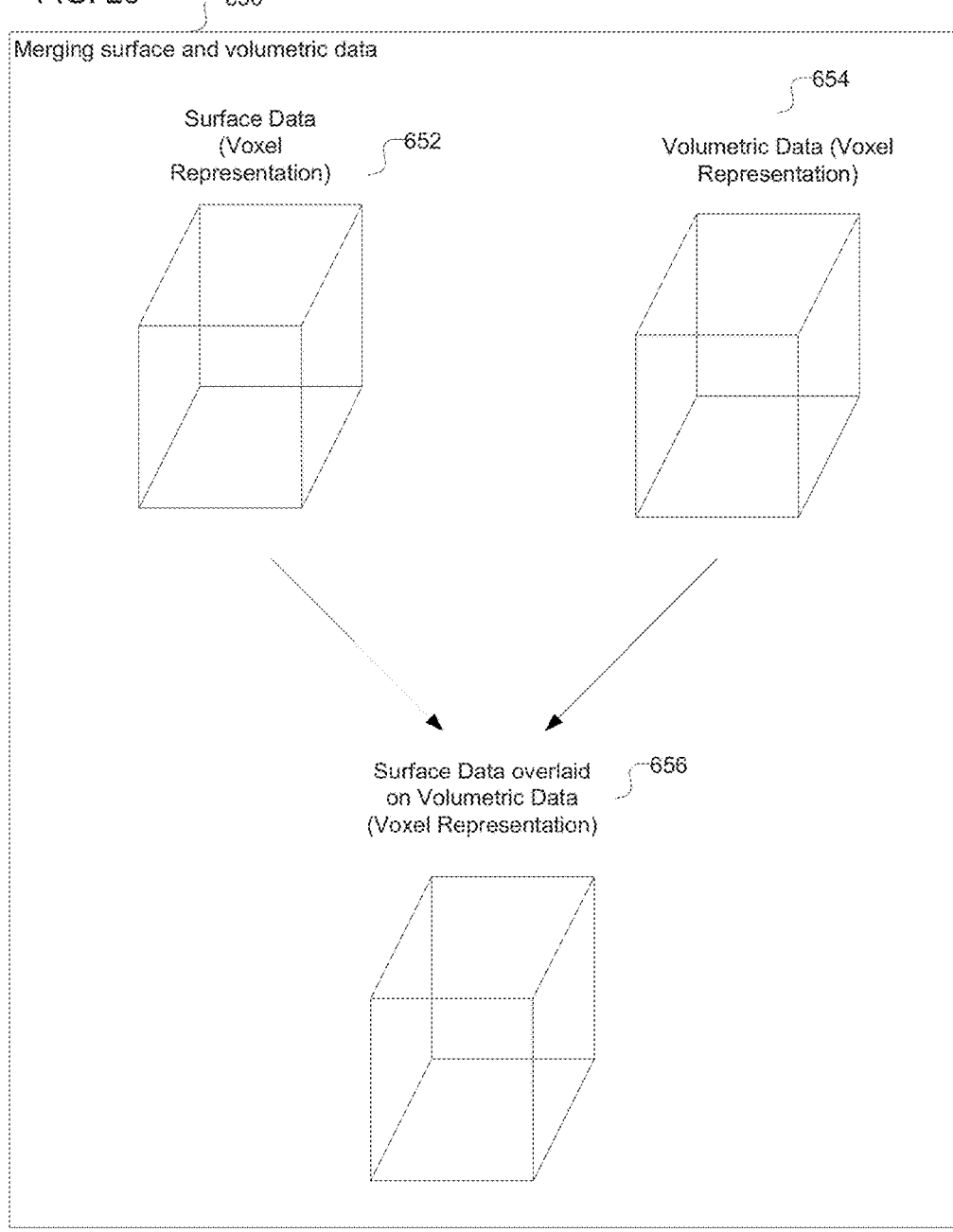
FIG. 20 illustrates a diagram that shows how surface data of the crown is merged to volumetric data of the tooth, in accordance with certain embodiments.

FIG. 20 illustrates a diagram 650 that shows how surface data of the crown is merged to volumetric data of the tooth, in accordance with certain embodiments. An empty cube of voxels in the three dimensional space is populated with the shape data of a crown. As a result, the surface data of the crown is represented via voxels of a three dimensional space 652.

The three dimensional space 652 with surface data is overlaid on the three dimensional space 654 that has the volumetric representation of the tooth, to generate the overlay of the surface data on the volumetric data shown in the three dimensional space 656. The fitting of the surface data to the volumetric data may be performed via an iterative closest point (ICP) registration. ICP may fit points in surface data to the points in volumetric data. In certain embodiment, the fitting may minimize the sum of square errors with the closest volumetric data points and surface data points. In certain embodiments, the limited length vectors of the surface data are represented as voxels prior to performing the ICP registration.

The anatomy of brackets, wires, filling or other features on the tooth may often assist in properly registering the surface data to the volumetric data. The registration may in various embodiments be performed via optimization techniques, such as simulated annealing, correlation techniques, dynamic programming, linear programming etc.

In certain embodiments a multiplicity of representations of the same object obtained by CBCT, magnetic resonance imagery (MRI), ultrasound imagery, intra-oral imagery based surface data, etc., may be registered to generate a better representation of a crown in comparison to embodiments that do not use data from the multiplicity of representations.

Figure 21:
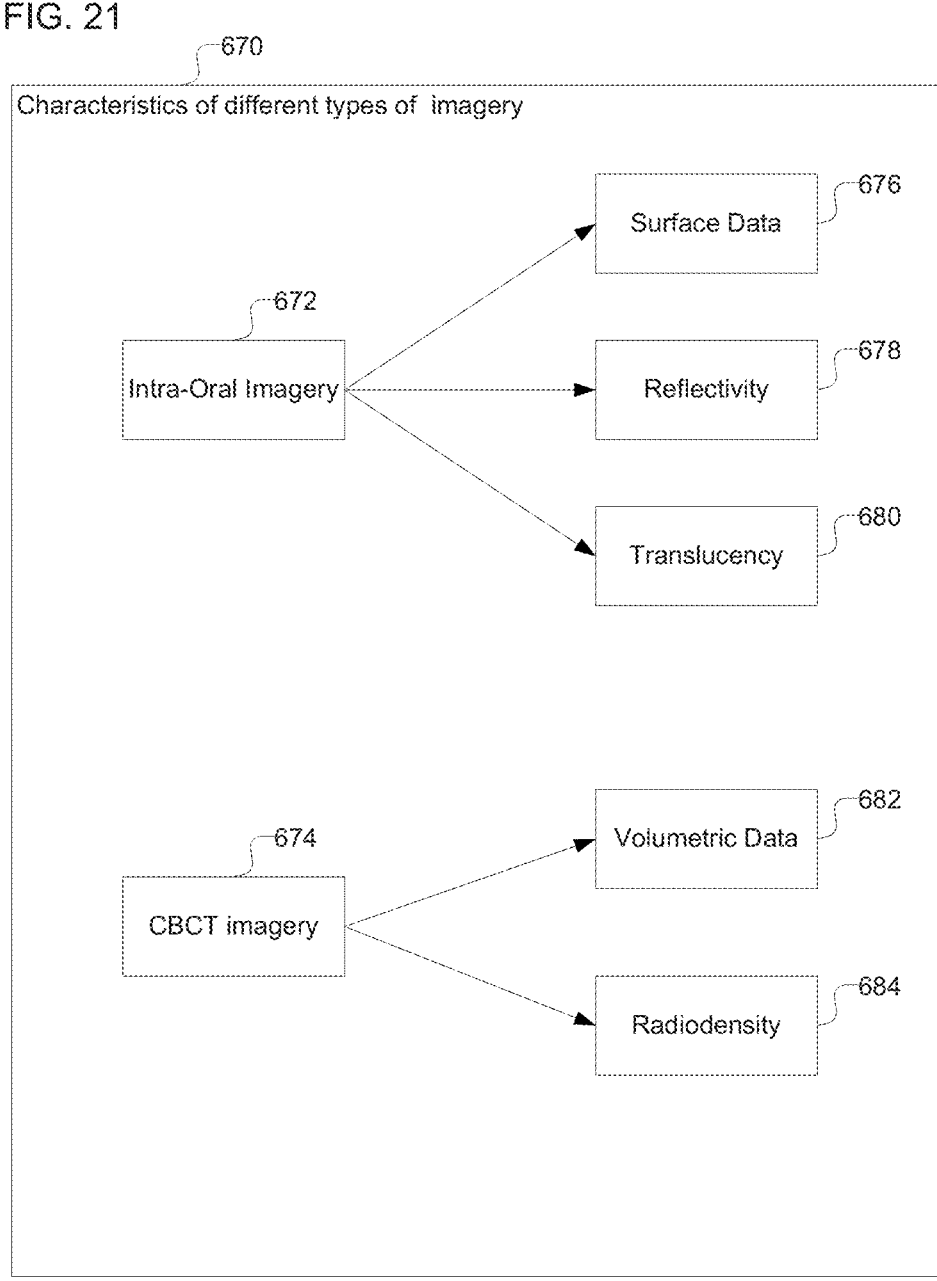
FIG. 21 illustrates a diagram that shows characteristics of different types of imagery, in accordance with certain embodiments.

FIG. 21 illustrates a diagram 670 that shows characteristics of different types of imagery, in accordance with certain embodiments. The intra-oral imagery 672 may provide not only the surface data 676 but may also be processed to provide information on reflectivity 678 and translucency 680 of the surface of the objects that are imaged. For example, the reflectivity and the translucency of the crown may be different from that the gingiva, and the intra-oral imagery 672 may be processed to distinguish the crown from the gingiva based on the reflectivity and the translucency differences and the segmentation of the crown may be improved by incorporating such additional information. In certain embodiments where interferometry fringe patterns are used for capturing the intra-oral imagery the reflectivity and translucency information may be generated with greater precision in comparison to embodiments where such fringe patterns are nor used.

In certain embodiments, the volumetric data 682 and the radiodensity information 684 corresponding to the CBCT imagery 674 may be used in association with the surface data 676, reflectivity information 678 and translucency information 680 of the intra-oral imagery 672 to provide additional cues for performing the registration of the surface data 676 and the volumetric data 682. Ray tracing mechanisms may also be used for simulating a wide variety of optical effects, such as reflection and refraction, scattering, and dispersion phenomena (such as chromatic aberration) for improving the quality of the different types of images and for registration.

FIG. 22 illustrates a diagram 688 that shows how surface data 690 extracted from intra-oral imagery is fitted to one or more of model data 694a, 694b, . . . 694n maintained as a library dataset 692. The library dataset 692 may include model data for various types of teeth (e.g., incisors, canines, molars, etc.) and also model data for various patient parameters, such as those based on age, gender, ethnicity, etc. In certain embodiments where the CBCT imagery is unavailable, the surface data 690 may be registered (reference numeral 696) to an appropriately selected model data 694a. . . 694n to provide better quality information to a dental practitioner. When the roots of a tooth are well formed and the crowns are relatively regular, then such fusion with model data is often adequate for treatment purposes. However, with as little as two to three degrees of error in alignment, such embodiments may have to be substituted with embodiments in which surface data from intra-oral imagery is registered with CBCT imagery to provide better quality information to the dental practitioner. In certain additional embodiments, the surface data is registered with the CBCT imagery with additional cues obtained from the model data.

FIG. 23 illustrates a flowchart 700 for augmenting CBCT imagery with data from intra-oral imagery to determine the boundary between roots and crowns, in accordance with certain embodiments. The operations shown in flowchart 700 may be performed via the integrating application 108 that executes in the computational device 102.

Control starts at block 702 in which the computational device 102 receives intra-oral imagery 104 and CBCT imagery 106. The integrating application 108 determines (at block 704) one or more crowns in the intra-oral imagery, wherein the one or more crowns of the intra-oral imagery are represented by limited length vectors or voxels, and the CBCT imagery is represented by voxels. Control proceeds to block 706, in which the integrating application 108 integrates the one or more crowns determined in the intra-oral imagery into the CBCT imagery by registering the limited length vectors or voxels that represent the one or more crowns in the intra-oral imagery with the voxels of the CBCT imagery, to determine a boundary between at least one crown and at least one root in the CBCT imagery.

FIG. 24 illustrates a flowchart 800 for determining a localized area in CBCT imagery to generate a reduced size CBCT imagery, by augmenting CBCT imagery with data from intra-oral imagery, in accordance with certain embodiments. The operations shown in flowchart 800 may be performed via the integrating application 108 that executes in the computational device 102.

Control starts at blocks 802 and 804 in which CBCT imagery and intra-oral imagery are provided to the integrating application 108. The integrating application 108 determines (at block 806) an area of interest in the intra-oral imagery, wherein the area of interest corresponds to a location of the one or more crowns determined in the intra-oral imagery via segmentation.

Control proceeds to block 808 in which the integrating application 108 extracts from the CBCT imagery the area of interest to reduce the size of the CBCT imagery, and the reduced size CBCT imagery is stored (at block 810) in the computational device 102.

Therefore FIG. 24 illustrates certain embodiments in which the size of CBCT imagery is reduced by incorporating an area of interest determined from intra-oral imagery.

Figure 25:
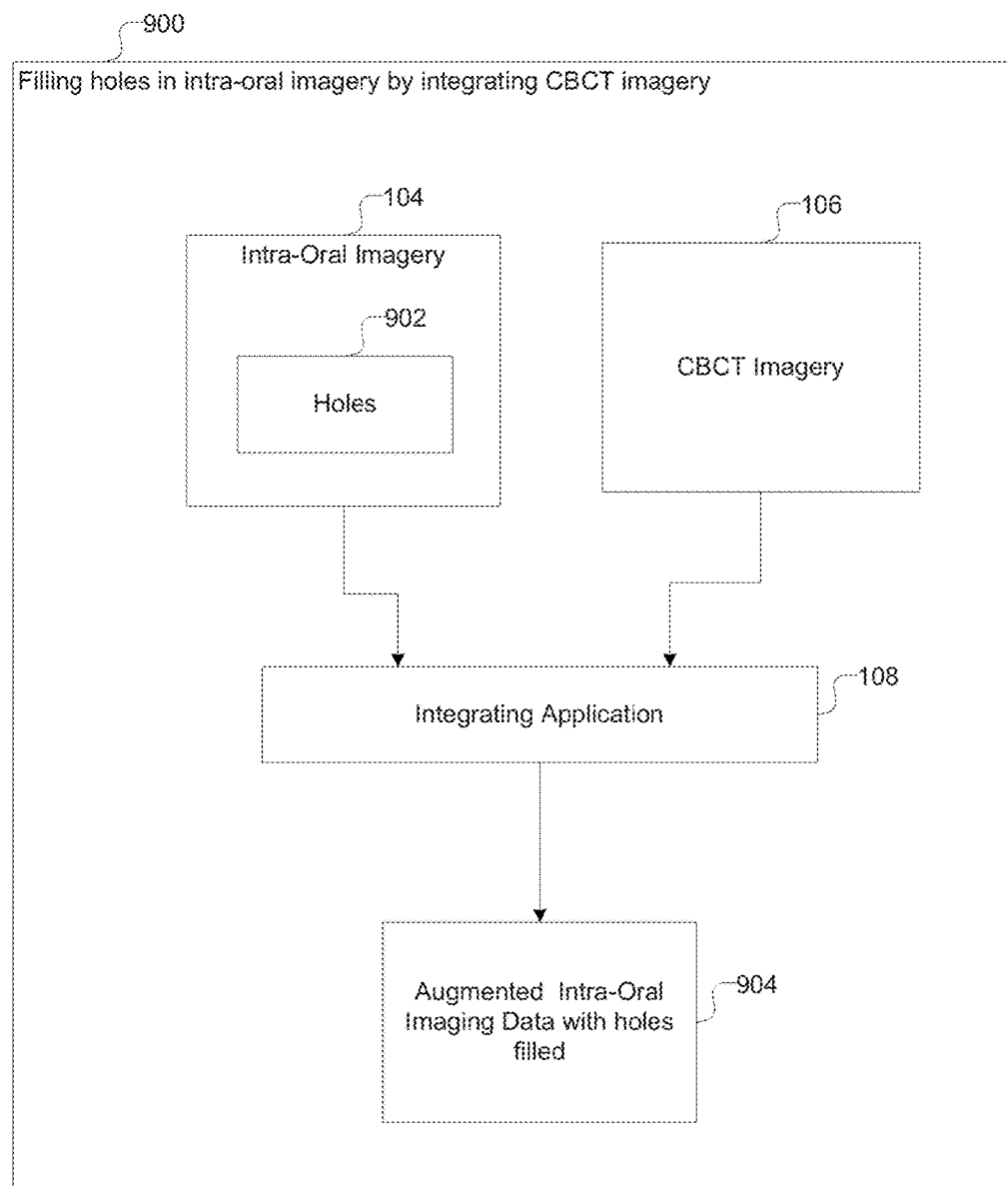
FIG. 25 illustrates a diagram that shows how holes are filled in intra-oral imagery by integrating CBCT imagery with intra-oral imagery, in accordance with certain embodiments.

FIG. 25 illustrates a diagram 900 that shows how holes are filled in intra-oral imagery by integrating CBCT imagery with intra-oral imagery, accordance with certain embodiments.

In FIG. 25 an exemplary intra-oral imagery 104 has holes 902 (i.e., areas of the crown of teeth that are not imaged by the intra-oral imaging system 112). The integrating application 108 uses the CBCT imagery 106 to fill the holes via the low precision crowns without holes that are found in the CBCT imagery 106, to generate augmented intra-oral imaging data 904 in which all holes are filled. In certain embodiments, a range of radiodensities are determined in voxels of a determined boundary between roots and crowns, and based on the range of radiodensities and the determined boundary, the holes in the intra-oral imagery are filled from selected voxels of the CBCT imagery.

Figure 26:
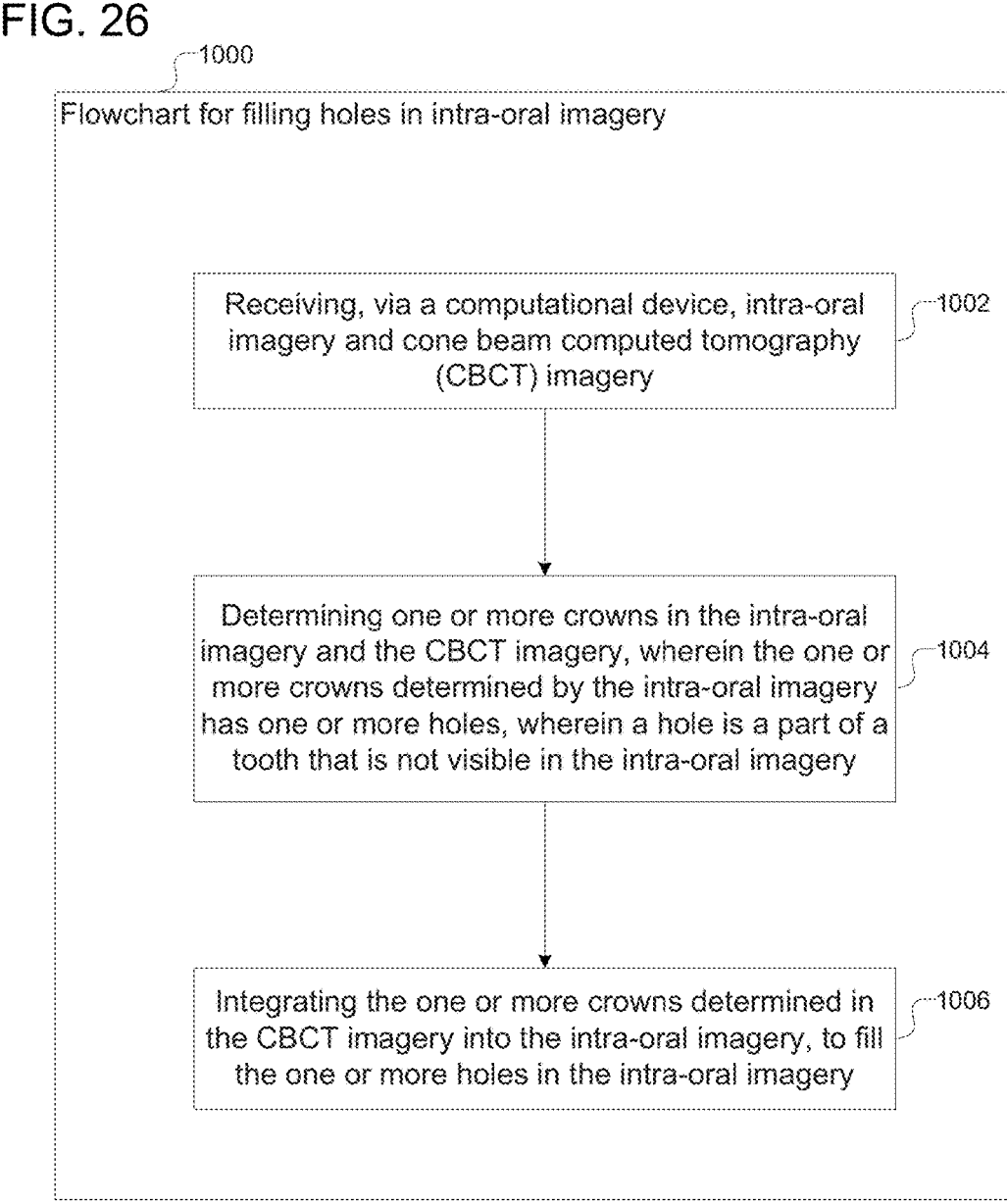
FIG. 26 illustrates a flowchart that shows how holes are filled in intra-oral imagery by integrating CBCT imagery with intra-oral imagery, in accordance with certain embodiments.

FIG. 26 illustrates a flowchart 1000 that shows how holes are filled in intra-oral imagery by integrating CBCT imagery with intra-oral imagery, accordance with certain embodiments. The operations shown in flowchart 1000 may be performed via, the integrating application 108 that executes in the computational device 102.

Control starts at block 1002 in which the computational device 102 receives intra-oral imagery 104 and volumetric imagery, such as, cone beam computed tomography (CBCT) imagery 106. Control proceeds to block 1004, in which the integrating application 108 determines one or more crowns in the intra-oral imagery 104 and the CBCT imagery 106, where the one or more crowns determined by the intra-oral imagery 104 has one or more holes, and where a hole is a part of a tooth that is not visible in the intra-oral imagery. The one or more crowns determined in the CBCT imagery are integrated (at block 1006) into the intra-oral imagery 104, to fill the one or more holes in the intra-oral imagery.

Therefore FIGS. 25 and 26 illustrate how holes are filled in intra-oral imagery by integrating information from CBCT imagery. Conversely, if missing or degraded data is found in volumetric imagery, such missing or degraded data may be filled from surface data found in the intra-oral imagery.

Figure 27:
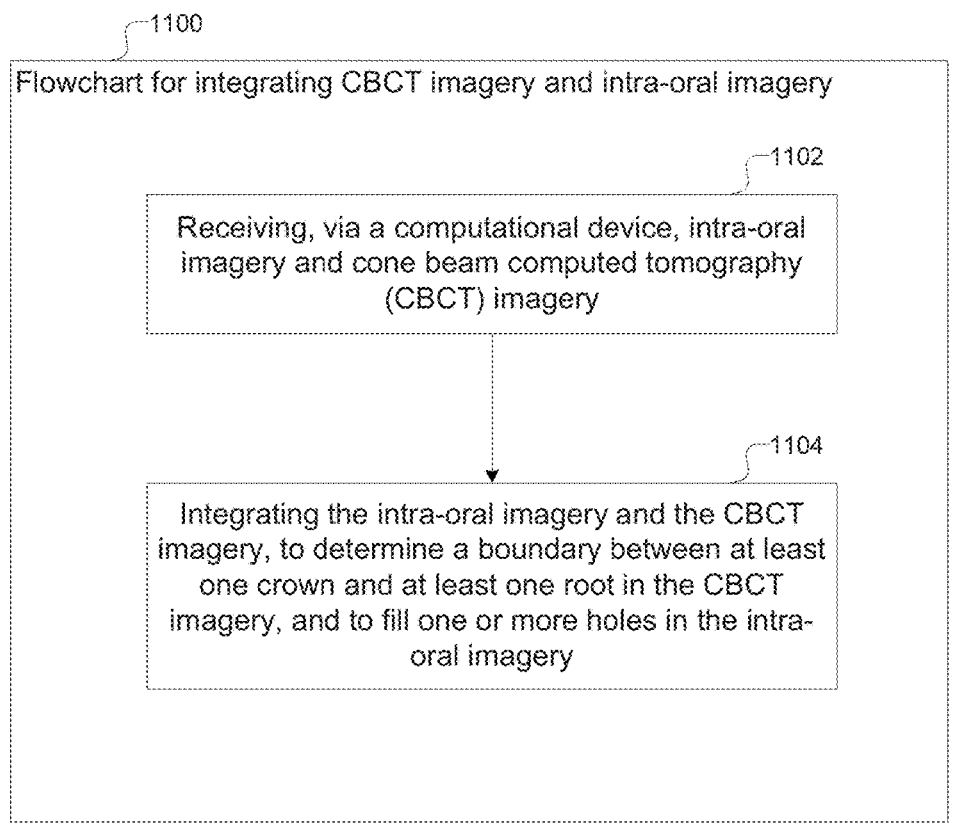
FIG. 27 illustrates a flowchart that shows how CBCT imagery is integrated with intra-oral imagery, in accordance with certain embodiments.

FIG. 27 illustrates a flowchart 1100 that shows how CBCT imagery 106 is integrated with intra-oral imagery 104, in accordance with certain embodiments. The operations shown in flowchart 1100 may be performed via the integrating application 108 that executes in the computational device 102.

Control starts at block 1102 in which a computational device 102 receives intra-oral imagery 104 and CBCT imagery 106. The intra-oral imagery 104 and the CBCT imagery 106 are integrated (at block 1104), to determine a boundary between at least one crown and at least one root in the CBCT imagery 106, and to fill one or more holes in the intra-oral imagery 104.

Figure 28:
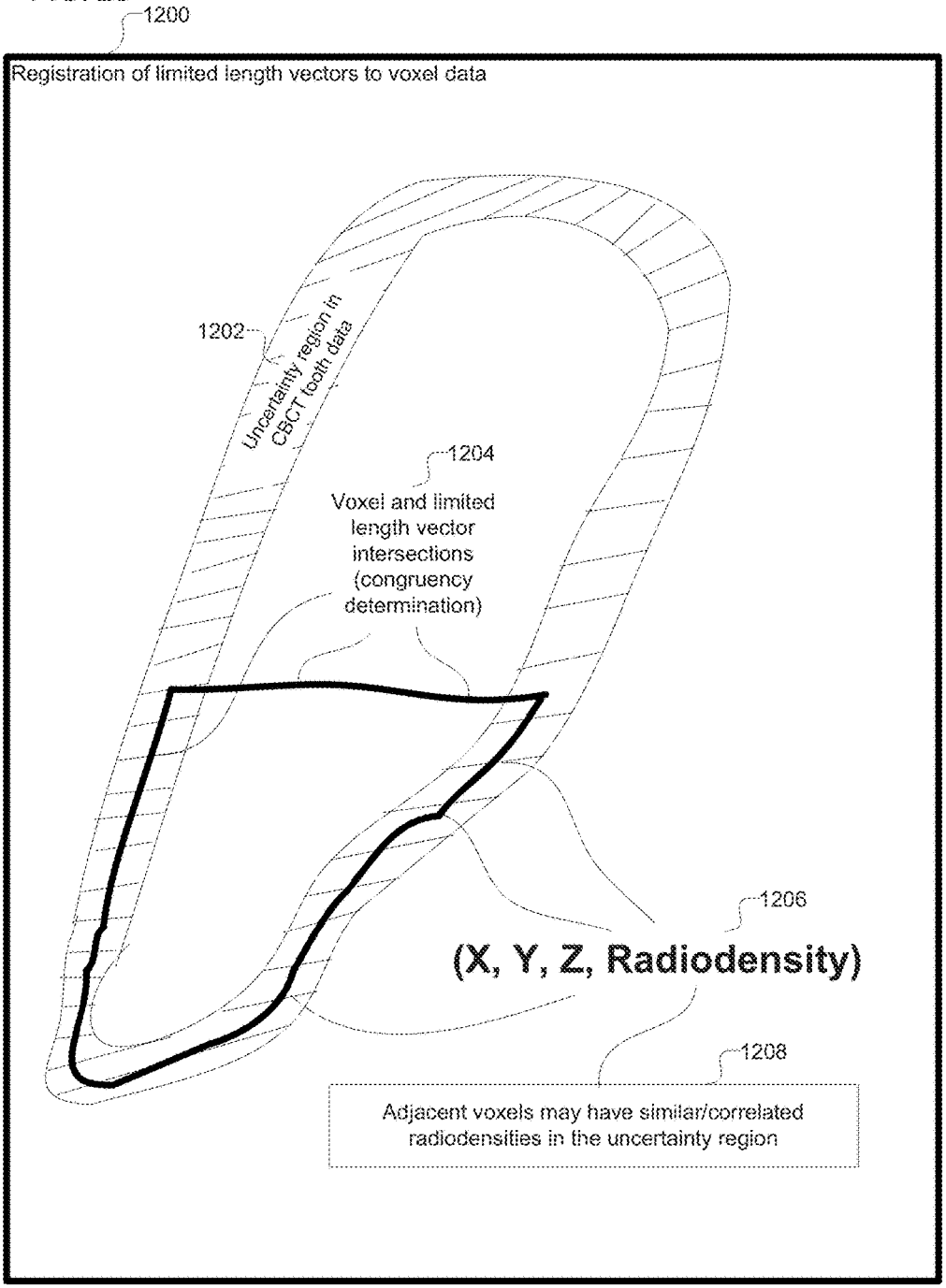
FIG. 28 illustrates a block diagram that shows how limited length vectors of intra-oral imagery are registered to voxel data of CBCT imagery, in accordance with certain embodiments.

FIG. 28 illustrates a block diagram 1200 that shows how limited length vectors of intra-oral imagery are registered to voxel data of CBCT or other volumetric imagery, in accordance with certain embodiments.

In FIG. 28 the hatched area indicated via reference numeral 1202 indicates an uncertainty region of the CBCT imagery in which the actual tooth boundary of the patient is likely to found. The limited length vectors (or voxels) of the intra-oral imagery are registered to the voxels of the CBCT imagery to determine the intersections 1204. At each of the intersections 1204 there is an X,Y,Z coordinate and an associated radiodensity (shown via reference numeral 1206), where adjacent voxels may have similar radiodensities or correlated radiodensities in the uncertainty region 1202 (as shown via reference numeral 1208).

Figure 29:
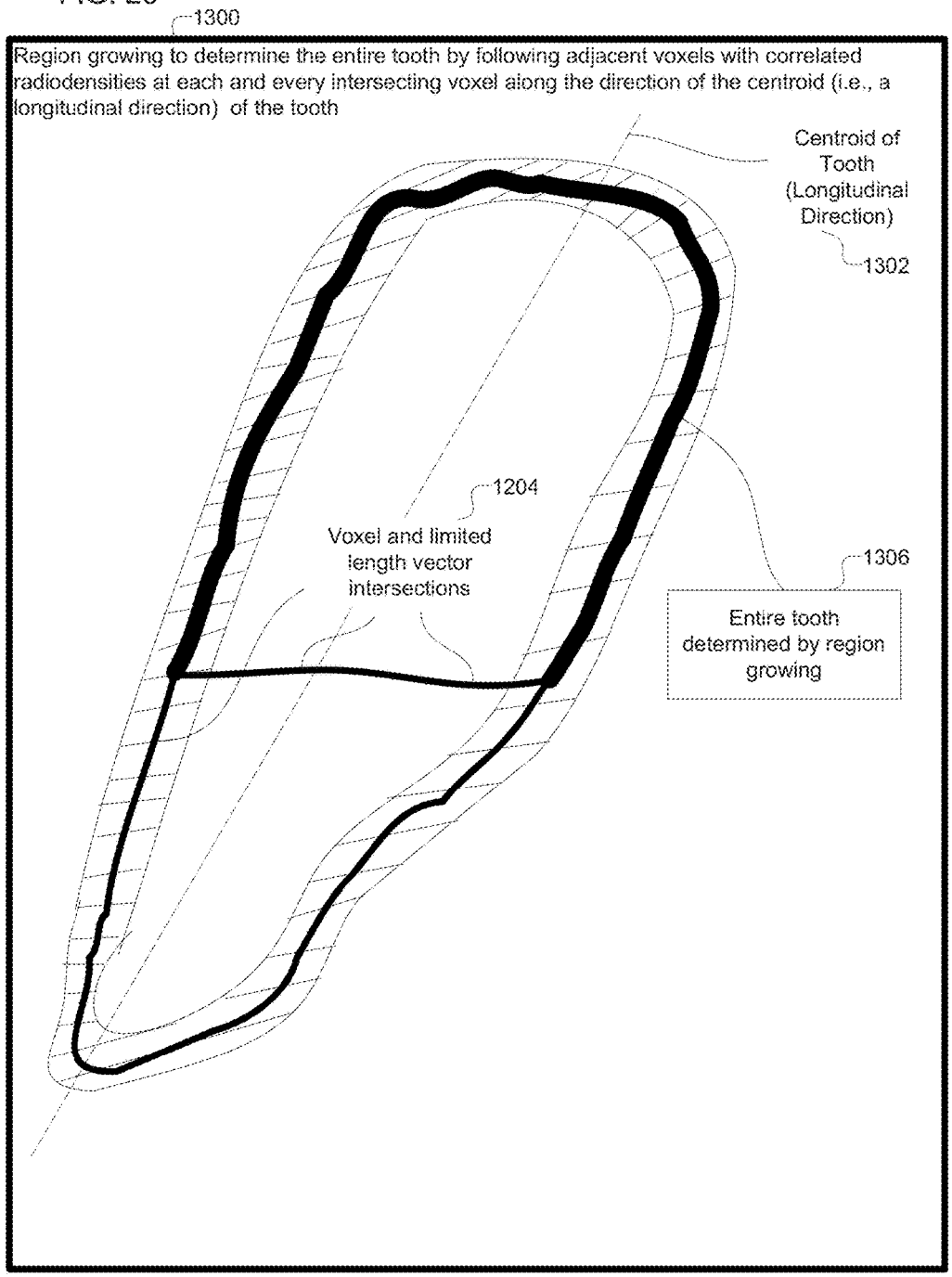
FIG. 29 illustrates a block diagram that shows how region growing is performed to determine the entire tooth by following adjacent voxels with correlated radiodensities at each and every intersecting voxel along the direction of the centroid or any other longitudinal direction of a tooth, in accordance with certain embodiments.

FIG. 29 illustrates a block diagram 1300 that shows how region growing is performed to determine the entire tooth by following adjacent voxels with correlated radiodensities at each and every intersecting voxel along the direction of the centroid 1302 of a tooth, in accordance with certain embodiments. The centroid is located along a longitudinal direction of the tooth. The correlated radiodensities may be determined via correlation windows of different sizes. For example, a cube of voxels with length, breadth, and height of three voxels each may be used as a correlation window to determine which adjacent voxel is most correlated to a previously determined voxel in terms of radiodensities.

Reference numeral 1306 shows the entire tooth outlined via region growing with seed values starting from the voxels and limited length vector (or surface voxel) intersections 1204 and the associated radiodensities. Other mechanisms may also be adopted for region growing to determine the entire tooth.

Figure 30:
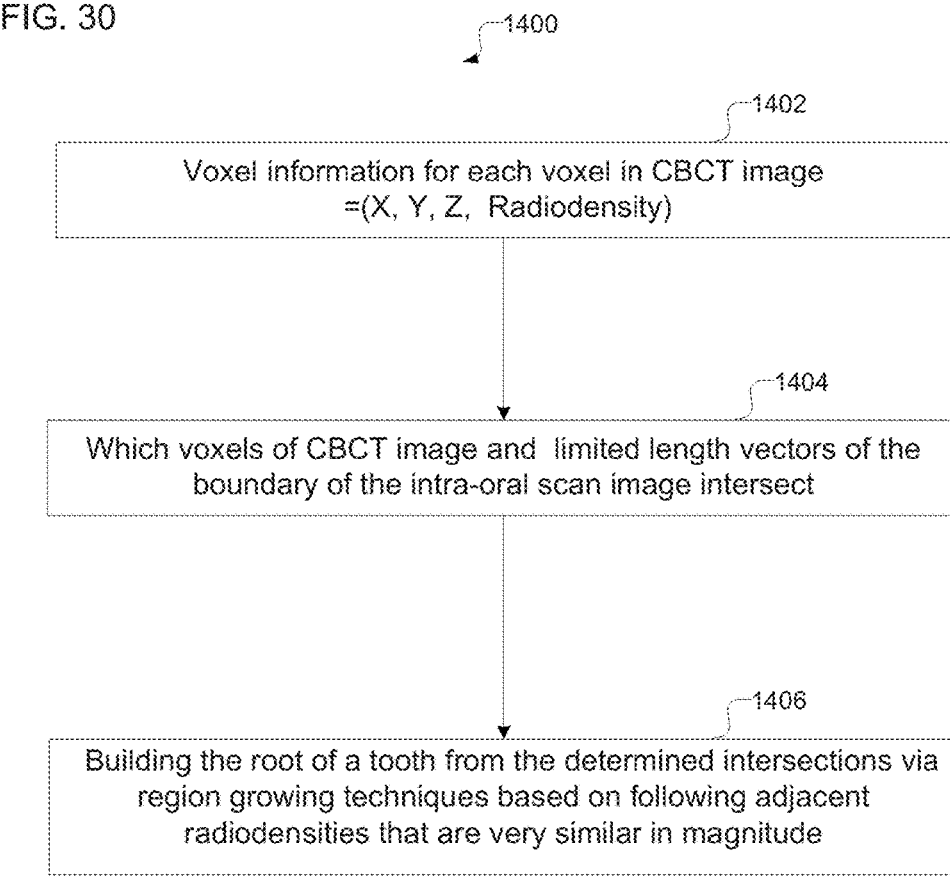
FIG. 30 illustrates a flowchart that shows how the root of a tooth is built from intersections of limited length vectors and voxels and region growing, in accordance with certain embodiments.

FIG. 30 illustrates a flowchart 1400 that shows how the root of a tooth is built from intersections of limited length vectors (or surface voxel) and voxels and region growing, in accordance with certain embodiments. Control starts at block 1402 where the voxel information at each voxel of a CBCT image is given by a volumetric coordinate X,Y,Z and the radiodensity. Control proceeds to block 1404 in which a determination is made as to which voxels of CBCT image and limited length vectors (or voxel) of the boundary of the crown of intra-oral image intersect. The root of the tooth is built (at block 1406) from the determined intersections via region growing techniques based on following adjacent radiodensities that are correlated (i.e., similar in magnitude) to each other.

Figure 31:
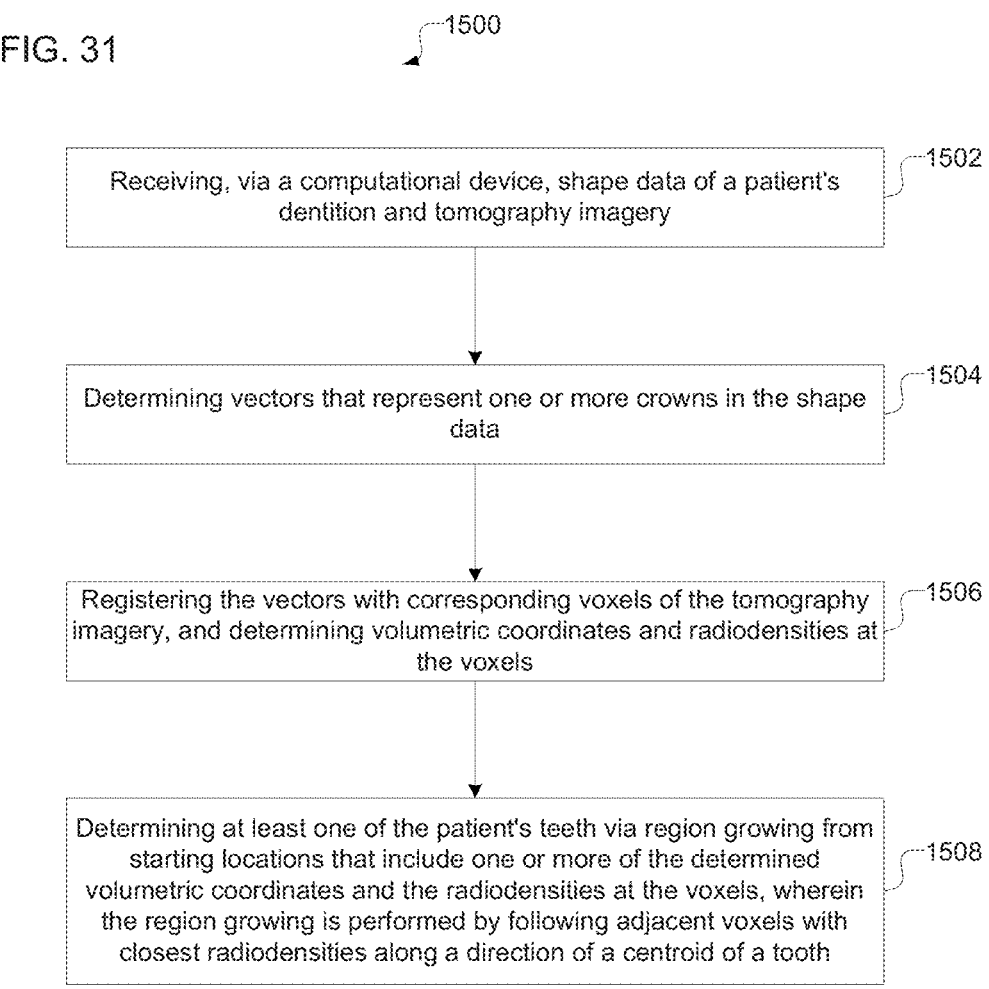
FIG. 31 illustrates a flowchart that shows how voxels of tomography imagery and limited length vectors of shape data are integrated, in accordance with certain embodiments.

FIG. 31 illustrates a flowchart 1500 that shows how voxels of tomography (i.e., volumetric) imagery and limited length vectors of shape data are integrated, in accordance with certain embodiments. A computational device receives (at block 1502) shape data of a patient's dentition and tomography imagery. Vectors that represent one or more crowns in the shape data are determined (at block 1504). The vectors are registered with corresponding voxels of the tomography imagery, and volumetric coordinates and radiodensities at the voxels are determined (at block 1506). At least one of the patient's teeth is determined via region growing from starting locations that include one or more of the determined volumetric coordinates and the radiodensities at the voxels, and the region growing is performed by following adjacent voxels with closest radiodensities along a direction of a centroid of a tooth (at block 1508). In alternative embodiments voxels (referred to as surface voxel) corresponding to the limited length vectors of the surface data may be used instead of the limited length vectors for registration.

Figure 32:
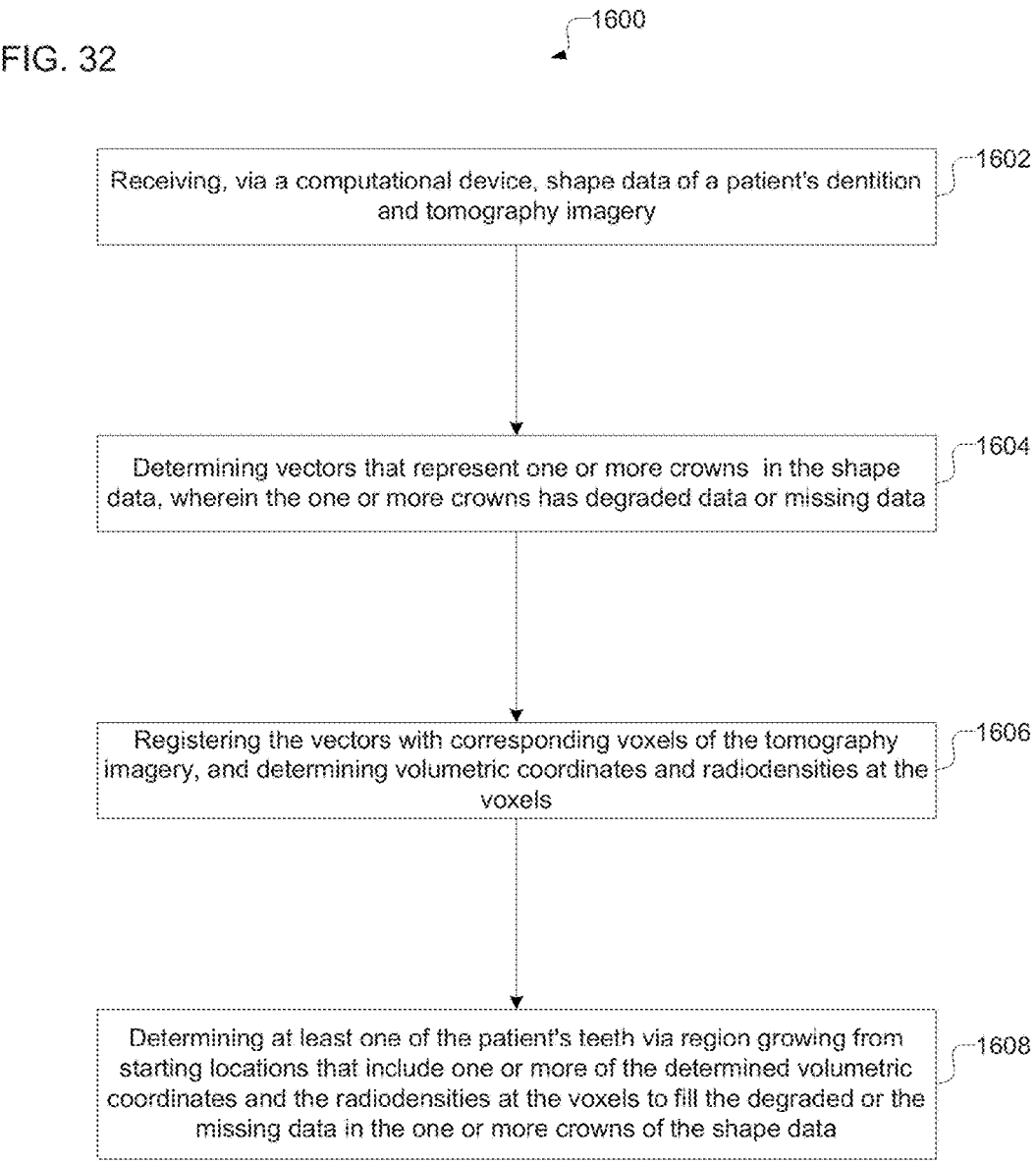
FIG. 32 illustrates a flowchart that shows how missing or degraded data in shape data is filled by integrating voxels of tomography imagery and limited length vectors of shape data, in accordance with certain embodiments.

FIG. 32 illustrates a flowchart 1600 that shows how missing or degraded data in shape data is filled by integrating voxels of tomography imagery and limited length vectors of shape data, in accordance with certain embodiments. A computational device receives (at block 1602) shape data of a patient's dentition and tomography imagery. Vectors that represent one or more crowns in the shape data are determined, wherein the one or more crowns has degraded data or missing data (at block 1604). The vectors are registered with corresponding voxels of the tomography imagery, and volumetric coordinates and radiodensities at the voxels are determined (at block 1606). At least one of the patient's teeth is determined via region growing from starting locations that include one or more of the determined volumetric coordinates and the radiodensities at the voxels to fill the degraded or the missing data in the one or more crowns of the shape data (at block 1606).

In certain alternative embodiments vectors are registered with corresponding voxels of the tomography imagery to determine volumetric coordinates and radiodensities at the voxels, to determine a tooth with greater precision and to fill missing or degraded data in the shape data. In certain embodiments, by determining the tooth with greater precision the received tomography imagery is obtained with usage of lesser radiation.

Figure 33:
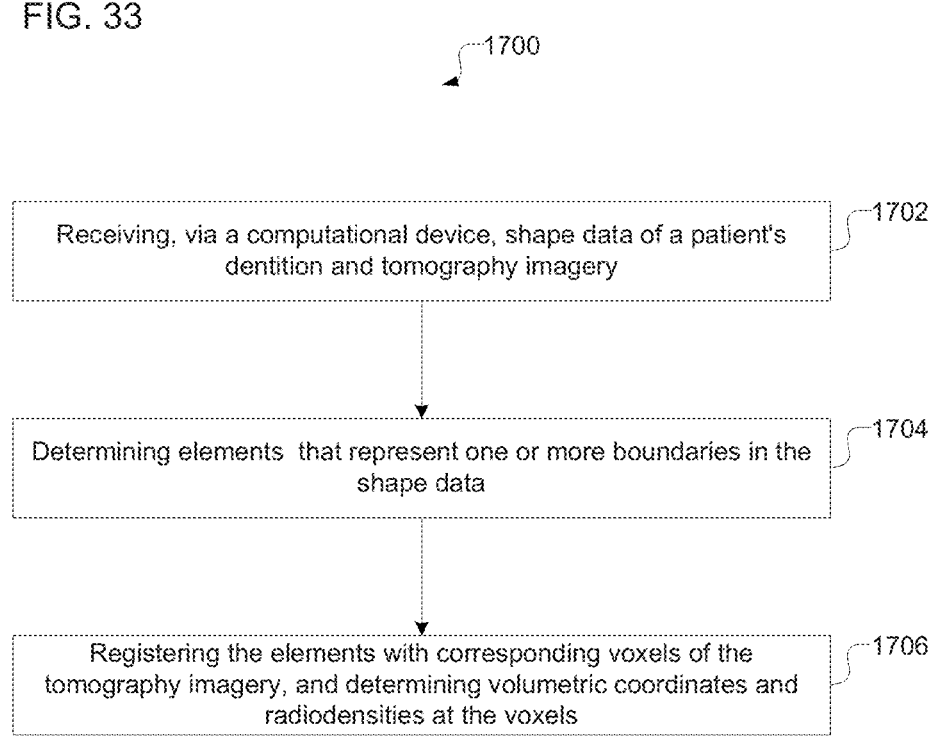
FIG. 33 illustrates a flowchart that shows registration of elements in shape data with corresponding voxels in tomographic imagery to determine volumetric coordinates and radiodensities at the voxels, in accordance with certain embodiments.

FIG. 33 illustrates a flowchart 1700 that shows registration of elements (e.g., vectors) in shape data with corresponding voxels in tomographic imagery to determine volumetric coordinates and radiodensities at the voxels, in accordance with certain embodiments. A computational device receives (at block 1702) shape data of a patient's dentition and tomography imagery. Elements (e.g. vectors or voxels) that represent one or more boundaries in the shape data are determined (at block 1704). The elements are registered with corresponding voxels of the tomography imagery, and volumetric coordinates and radiodensities at the voxels are determined (at block 1706). In certain embodiments, the boundaries in the shape data delineate one or more crowns of teeth.

Figure 34:
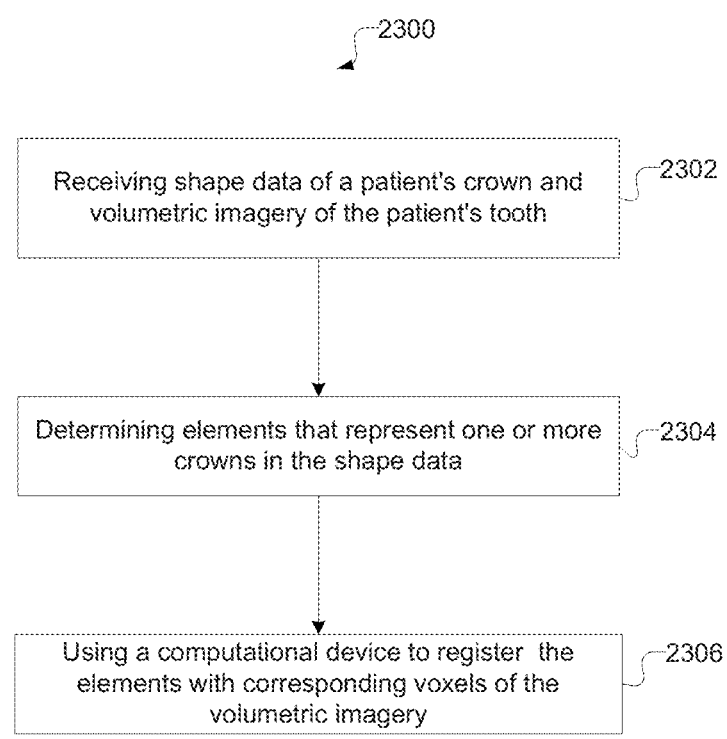
FIG. 34 illustrates a flowchart that shows registration of elements in shape data of a patient's crown with corresponding voxels in volumetric imagery, in accordance with certain embodiments.

FIG. 34 illustrates a flowchart 2300 that shows registration of elements in shape data of a patient's crown with corresponding voxels in volumetric imagery, in accordance with certain embodiments.

Control starts at block 2302 in which shape data of a patients crown and volumetric imagery of the patient's tooth is received. A determination is made (at block 2304) of elements that represent one or more crowns in the shape data. A computational device is used to register (at block 2306) the elements with corresponding voxels of the volumetric imagery.

Figure 35:
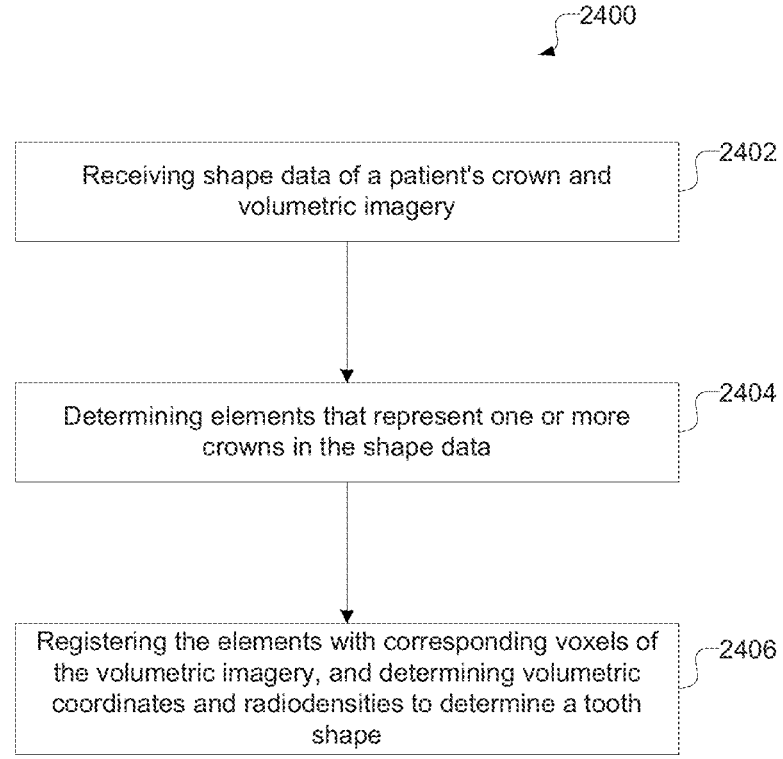
FIG. 35 illustrates a flowchart that shows registration of elements in shape data of a patient's crown with corresponding voxels in volumetric imagery to determine tooth shape, in accordance with certain embodiments.

FIG. 35 illustrates a flowchart 2400 that shows registration of elements in shape data of a patient's crown with corresponding voxels in volumetric imagery to determine tooth shape, in accordance with certain embodiments.

Control starts at block 2402 in which shape data of a patient's crown and volumetric imagery are received. A determination is made (at block 2404) of elements that represent one or more crowns in the shape data. The elements are registered (at block 2406) with corresponding voxels of the volumetric imagery by using a computational device, and volumetric coordinates and radiodensities are determined to determine a tooth shape.

Therefore, FIGS. 12-35 illustrate certain embodiments in which the tooth of a patient is determined more accurately by integrating information extracted from intra-oral imagery and CBCT imagery. Also, degraded or missing data in the crowns of intra-oral imagery are filled by integrating information extracted from CBCT imagery. By integrating intra-oral imagery with CBCT imagery, both intra-oral imagery and CBCT imagery are enhanced to have greater functionalities and CBCT imagery may be obtained with usage of a lower amount of radiation.

FIGS. 12-35 illustrate embodiments in which shape data of a patients crown and volumetric imagery of the patient's tooth are received. A determination is made of elements that represent one or more crowns in the shape data. A computational device is used to register the elements with corresponding voxels of the volumetric imagery. In additional embodiments, a determination is made of volumetric coordinates and radiodensities corresponding to the voxels. In further embodiments, at least one of the patient's root is determined via region growing from starting locations that include one or more of the determined volumetric coordinates and radiodensities at the voxels. In further embodiments, the region growing is performed by identifying adjacent voxels that possess correlated radiodensities along a longitudinal direction of the patient's tooth.

In further embodiments, the elements are vectors, and boundaries in the shape data correspond to the one or more crowns. The one or more crowns are represented by a plurality of limited length vectors and the volumetric imagery is represented by a plurality of voxels. Intersections of the plurality of limited length vectors and the plurality of voxels are determined subsequent to the registering.

In further embodiments, the volumetric imagery is represented by a first plurality of voxels, and the one or more crowns are represented by a second plurality of voxels. The first plurality of voxels and the second plurality of voxels are registered.

In further embodiments, one or more crowns are determined in the shape data via segmentation of the shape data.

In certain embodiments a computational device receives shape data of a patient's crown and volumetric imagery. A determination is made of elements that represent one or more crowns in the shape data. The elements are registered with corresponding voxels of the volumetric imagery. Volumetric coordinates and radiodensities are determined to determine a tooth shape. In additional embodiments, determining the tooth shape comprises filling missing or degraded data in the shape data. In yet additional embodiments, determining the tooth shape comprises filling missing or degraded data in the volumetric imagery.

In further embodiments, the tooth shape is determined with greater precision in comparison to the received volumetric imagery, and the tooth shape is determined with greater precision with usage of lesser radiation. At least one of the patient's root is determined via region growing from starting locations that include one or more of determined volumetric coordinates and radiodensities at the voxels.

In yet further embodiments, the volumetric imagery is represented by a first plurality of voxels. The one or more crowns are represented by vectors or a second plurality of voxels. The first plurality of voxels are registered to the vectors or the second plurality of voxels.

Further Details of Embodiments in a volumetric data representation there may be areas of high contrast and low contrast. When segmenting via thresholding (e.g., by thresholding radiodensities) it may be easier to threshold crowns than roots. This is because crowns appear with high density against soft tissue. It may be noted that roots appear with low contrast against the bone. High contrast junctions may be easier to segment in this manner. In certain embodiments, the crowns may be thresholded and the borders may be used to seed the segmentation to isolate the roots. Thus the volumetric data set may be used to segment itself. This may automatically register the crown root object. This may even be used to register the crown surface data.

In certain embodiments, instead of segmenting roots, certain embodiments may extract only the centroid of the root.

Certain embodiments may link the shape and tomography imagery data together in a file system. For example, information may be added to the headers of the image files of both the CBCT and intra-oral scan data to enable viewing software to easily reference one from the other. Alternatively, the viewing software may keep track of which intra-oral scan image and CBCT image files have been registered with one another and store the information in a separate file. In certain embodiments correlation or optimization techniques may be used to find the intersection points in the image data.

In certain embodiments, the output of the processes is a data structure that is an advanced representation of the surface or a volumetric data enhanced by the fusion process of registration of multiple sources of imagery. Multidimensional data representation and visualization techniques may be used to display such enhanced surfaces or volumes. In certain embodiments, the collected image data may after processing and registration be rendered and displayed as three dimensional objects via volumetric rendering and segmentation.

Integration of Model Data, Surface Data and Volumetric Data

Figure 36:
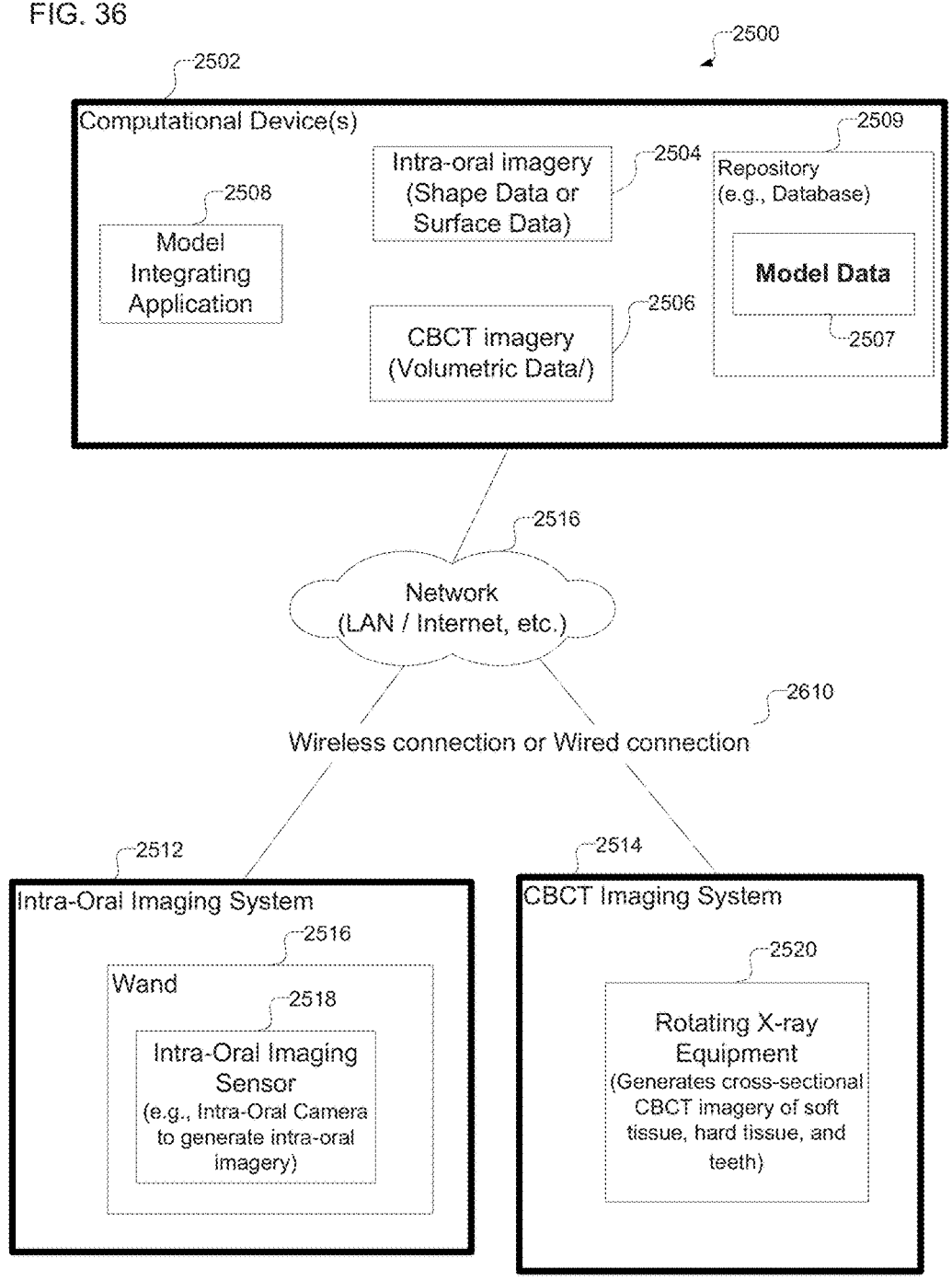
FIG. 36 illustrates a block diagram of a computing and imaging environment that includes a computational device that integrates surface data provided by intra-oral imagery and volumetric imagery, such as CBCT imagery, with model data, in accordance with certain embodiments.

FIG. 36 illustrates a block diagram of a computing and imaging environment 2500 that includes a computational device 2502 that integrates surface data (i.e., shape data) provided by intra-oral imagery 2504 and volumetric data provided by volumetric imagery 2506, such as CBCT imagery, with model data 2507, in accordance with certain embodiments. The computational device 2502 may include any suitable computational device such as a personal computer, a server computer, a mini computer, a mainframe computer, a blade computer, a tablet computer, a touch screen computing device, a telephony device, a cell phone, a mobile computational device, a dental equipment having a processor, etc., and in certain embodiments the computational device 2502 may provide web services or cloud computing services. In certain alternative embodiments, more than one computational device may be used for storing data or performing the operations performed by the computational device 2502.

The intra-oral imagery 2504 provides surface data of a patient's crown and the CBCT imagery 2506 provides volumetric imagery of a patient's tooth, where the tooth may include both the crown and the root. In alternative embodiments, the surface data of the patient's crown may be provided by imagery that is different from intra-oral imagery, and the volumetric imagery may be provided by other types of tomographic imagery, ultrasonic imagery, magnetic resonance imagery (MRI), etc. The volumetric imagery comprises three dimensional imagery and may be represented via voxels. The model data 2507 may be stored in a repository 2509, where the repository 2509 may comprise a database or any other data repository. The model data 2507 may include three-dimensional models of tooth or roots. Different models may exist for different teeth. For example, there may be different models for incisors, canines, first molars, second molars, etc. The models may be different for teeth in maxillary and mandibular arches. The models may also differ based on patient parameters, such as age, gender, ethnicity, etc.

In certain embodiments, the model data 2507 may model the entirety of teeth, whereas in other embodiments the model data 2507 may model only the roots.

The computational device 2502 may include a model integrating application 2508, implemented in certain embodiments in software, hardware, firmware or any combination thereof. The model integrating application 2508 integrates the intra-oral imagery 2504, the CBCT imagery 2506, and the model data 2507, to provide additional functionalities that are not found in either the intra-oral imagery 2504 or the CBCT imagery 2506, or the model data 2507 when they are not integrated.

The computational device 2502 is coupled via one or more wired or wireless connections 2510 to an intra-oral imaging system 2512 and a CBCT imaging system 2514, over a network 2516. In certain embodiments, the network 2516 may comprise a local area network, the Internet, and intranet, a storage area network, or any other suitable network.

The intra-oral imaging system 2512 may include a wand 2516 having an intra-oral imaging sensor 2518, where in certain embodiments the intra-oral imaging sensor 2518 is an intra-oral camera that generates intra-oral imagery of the oral cavity of a patient. The CBCT imaging system 2514 may include a rotating X-ray equipment 2520 that generates cross-sectional CBCT imagery of the soft tissue, hard tissue, teeth, etc. of a patient.

Therefore, FIG. 36 illustrates certain embodiments in which a model integrating application 2508 that executes in the computational device 2502 integrates surface data (from an intra-oral imaging system 2512), volumetric data (from a CBCT imaging system 2514), and model data 2507 (stored in a repository 2509).

Figure 37:
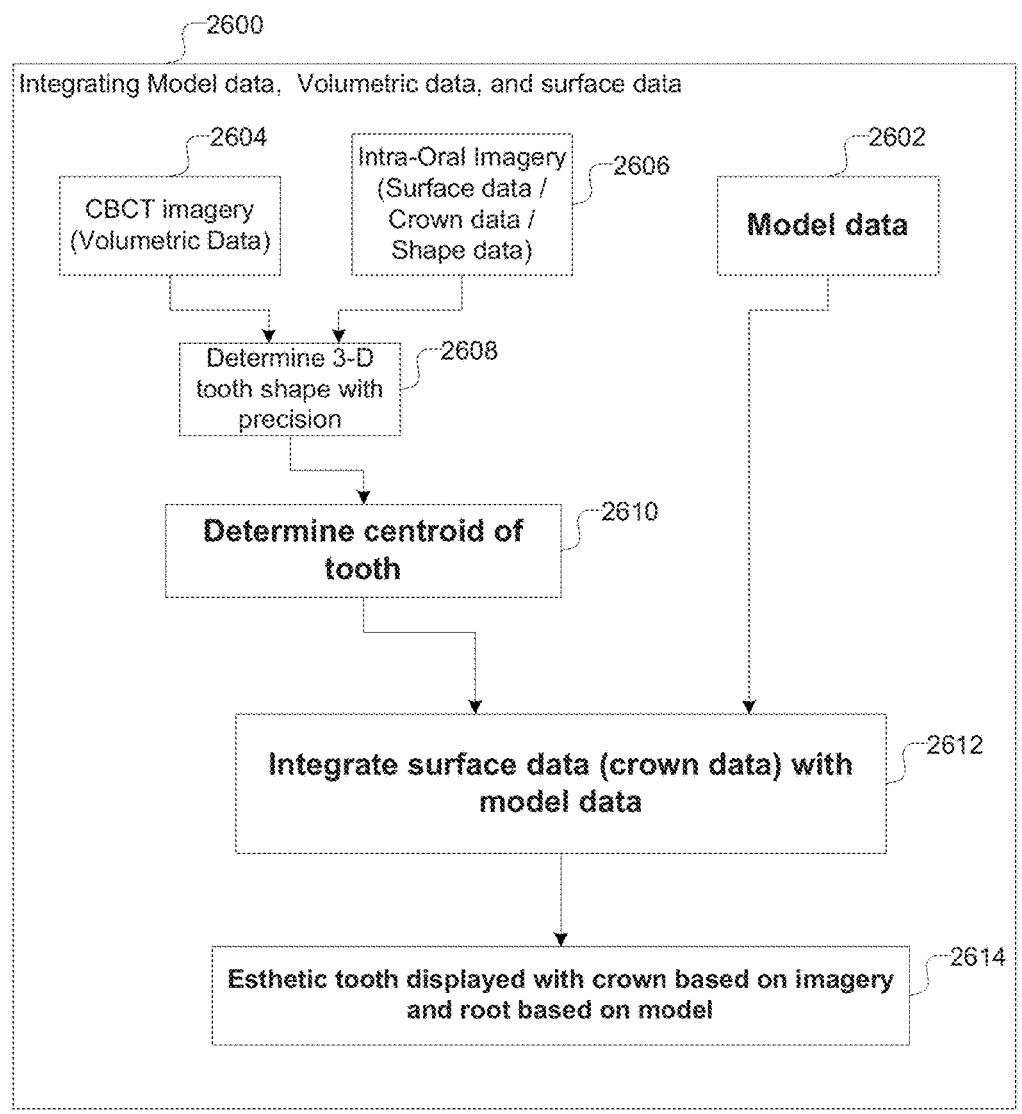
FIG. 37 illustrates a block diagram that shows how model data, volumetric imagery and surface data are integrated, in accordance with certain embodiments.

FIG. 37 illustrates a block diagram 2600 that shows how exemplary model data 2602, exemplary volumetric data 2604 and exemplary surface data 2606 are integrated, in accordance with certain embodiments.

In certain embodiments, the model integrating application 2508 integrates the volumetric data 2604 and the surface (i.e., shape) data 2606 to determine the tooth shape and the centroid of a patient's tooth. The embodiments for determining (reference numeral 2608) the tooth shape of the patient's tooth with precision is similar to the embodiments described in FIGS. 12-36. In certain embodiments, the centroid may be determined after the tooth shape has been determined. The centroid of a tooth corresponds to an orientation of the tooth, and the centroid may lie in a longitudinal direction of the tooth. Once a three-dimensional tooth shape is determined, the centroid of the tooth may be determined from the three dimensional tooth shape (reference numeral 2610).

Once the centroid of the tooth is determined, the model integrating application 2508 integrates the surface data (i.e., the crown data generated by the intra-oral imagery) with the model data 2602 (at reference numeral 2612), to generate and display an esthetic tooth whose crown corresponds to the patient's crown and whose root corresponds to the model root (reference numeral 2614). The centroid provides the appropriate orientation to align the model data to the surface data. It may be noted that images of the root obtained via CBCT are not very esthetic, and for presenting an esthetic appearance of a tooth, a model of a root may be fitted to the surface data corresponding to a patient's crown for various types of display.

Figure 38:
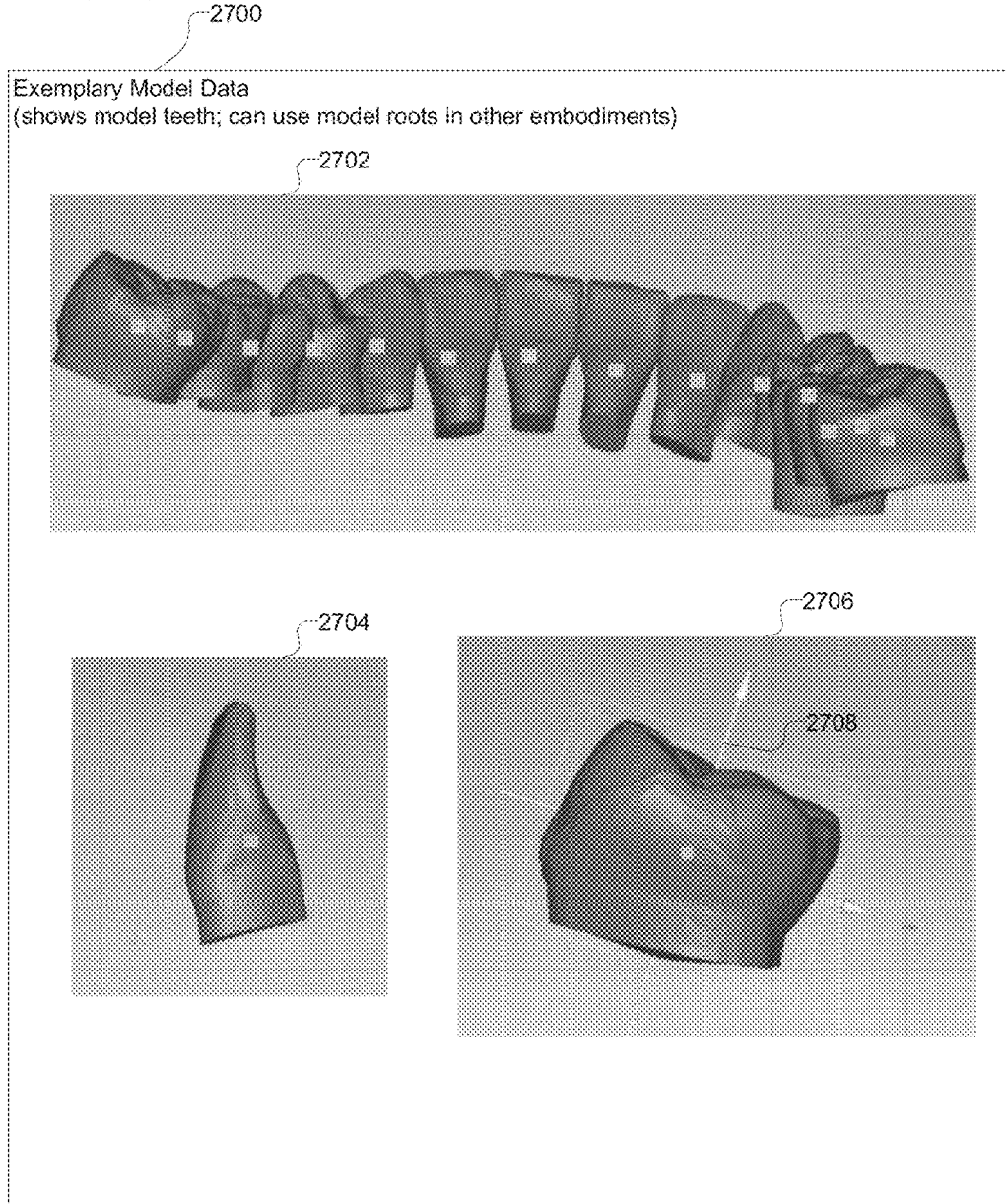
FIG. 38 illustrates a block diagram that shows exemplary model data, in accordance with certain embodiments.

FIG. 38 illustrates a block diagram 2700 that shows exemplary model data stored in the repository 2509, in accordance with certain embodiments. The exemplary model data shown in FIG. 38 may represent models of representative teeth of various types of patient and may be generated synthetically via a three-dimensional graphics modeling program. A set of model teeth 2702, a first representative tooth 2704, and a second representative tooth 2706 are shown in FIG. 38. In FIG. 38 a longitudinal axis 2708 of the tooth 2706 is also shown.

While FIG. 38 shows the models 2702, 2704, 2706 as models of tooth, in alternative embodiments, the models may represent roots rather than the entirety of the tooth. In any event, the roots that are seen in the model data 2700 are esthetically more pleasing to a human observer than actual roots generated from volumetric imagery.

Figure 39:
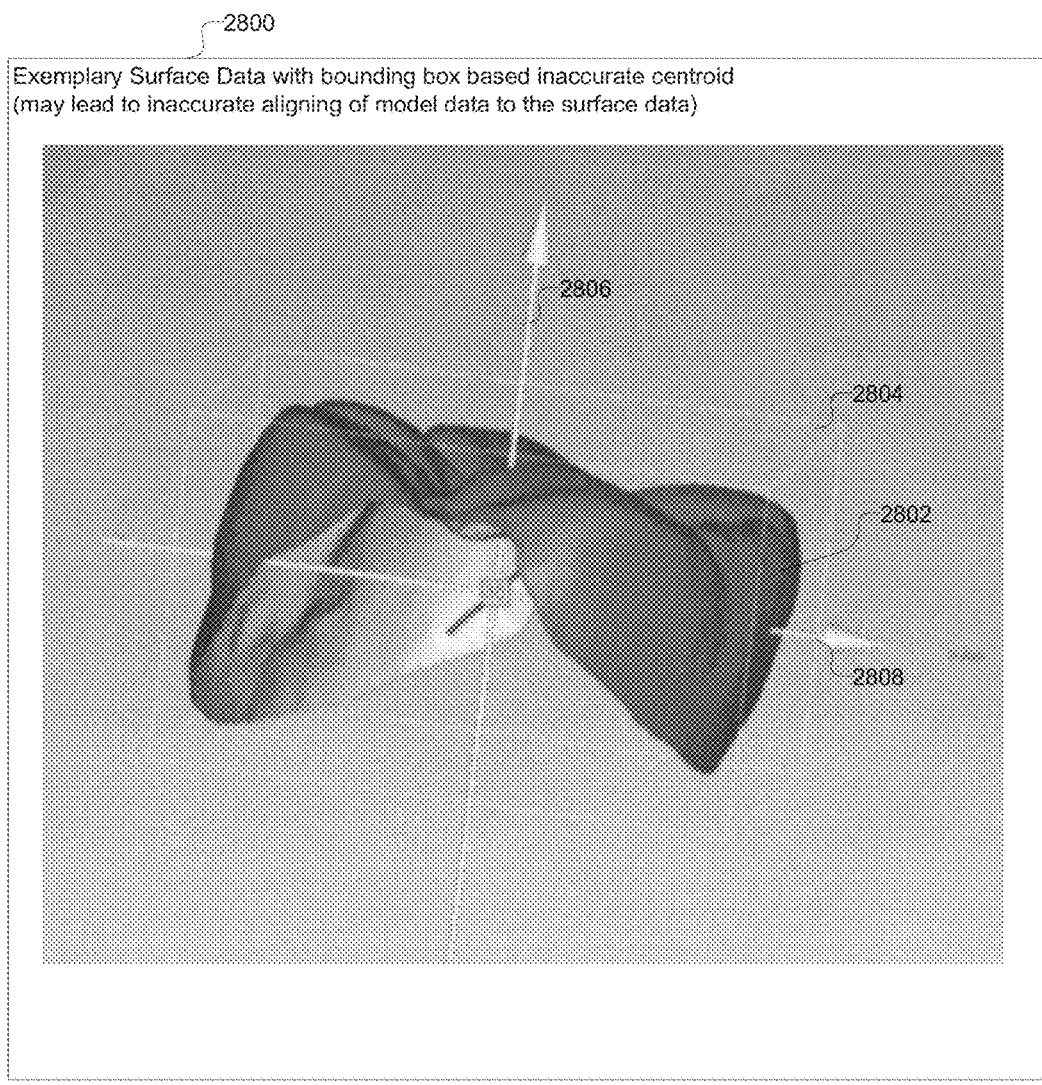
FIG. 39 illustrates a block diagram that shows relatively inaccurate determination of the centroid of a tooth from exemplary surface data alone, in accordance with certain embodiments.

FIG. 39 illustrates a block diagram 2800 that shows relatively inaccurate determination of the centroid of a tooth from exemplary surface data alone, in accordance with certain embodiments. In certain embodiments, the surface data 2802 that represents a crown may be determined from intra-oral imagery. A bounding box 2804 in three-dimension may be drawn enveloping the surface data, and a longitudinal line 2806 and a lateral line 2808 may be determined, where the longitudinal line 2806 may correspond to a rough centroid of the tooth. However, without determination of the entirety of the tooth the centroid 2806 is very inaccurate and fitting the surface data to model data may be difficult in such situations, and may lead to large errors.

Figure 40:
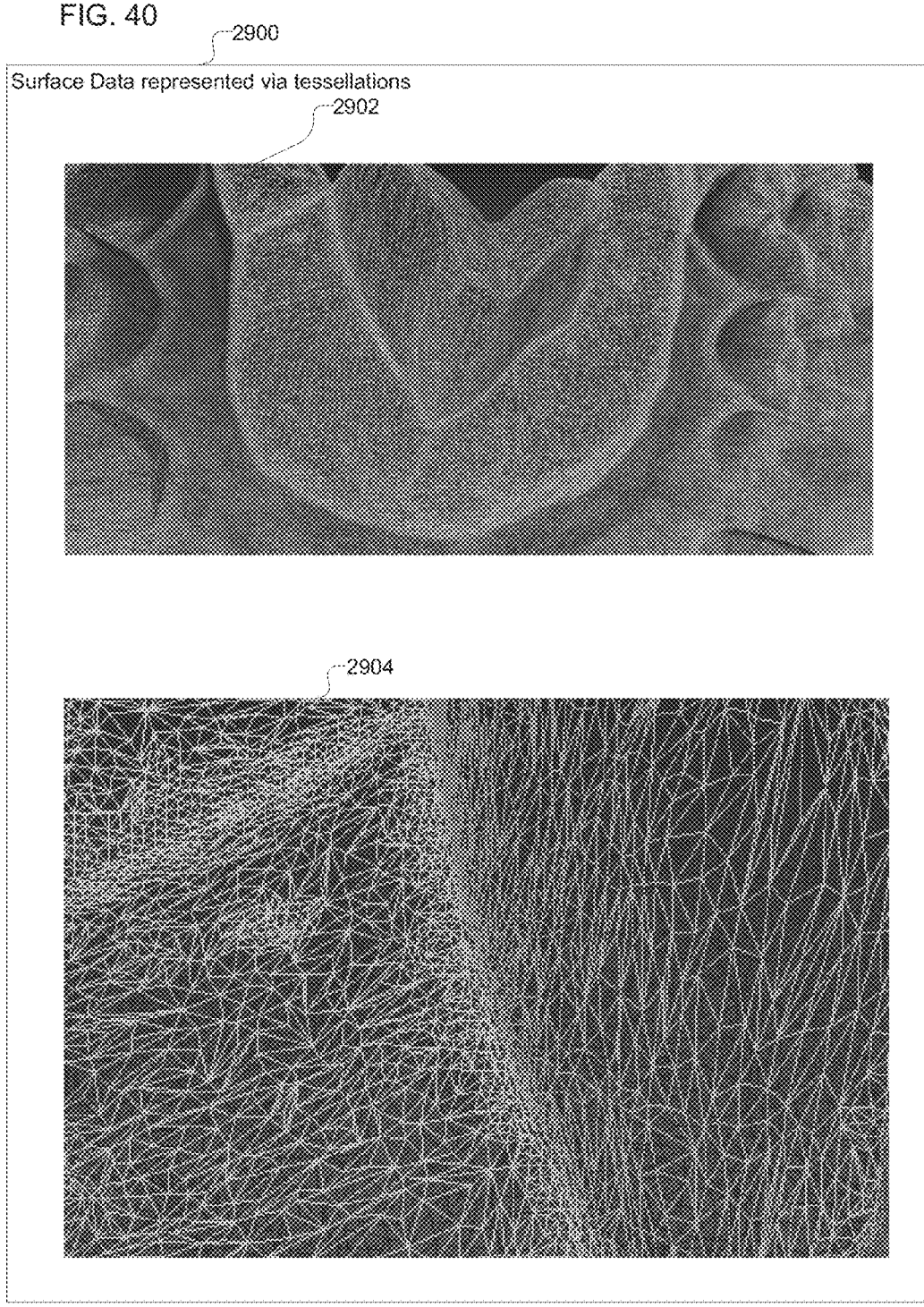
FIG. 40 illustrates a block diagram that shows tessellations that represent exemplary surface data, in accordance with certain embodiments.

FIG. 40 illustrates a block diagram 2900 that shows tessellations that represent exemplary surface data, in accordance with certain embodiments. The element shown via reference numeral 2904 is a magnified portion of the surface data shown via reference numeral 2902. In certain exemplary embodiments, the tessellations of the surface are triangular in shape and the triangular shapes may be seen in element 2904. The sides of the triangles may form limited length vectors. Other surface representations may of course be used in alternative embodiments.

Figure 41:
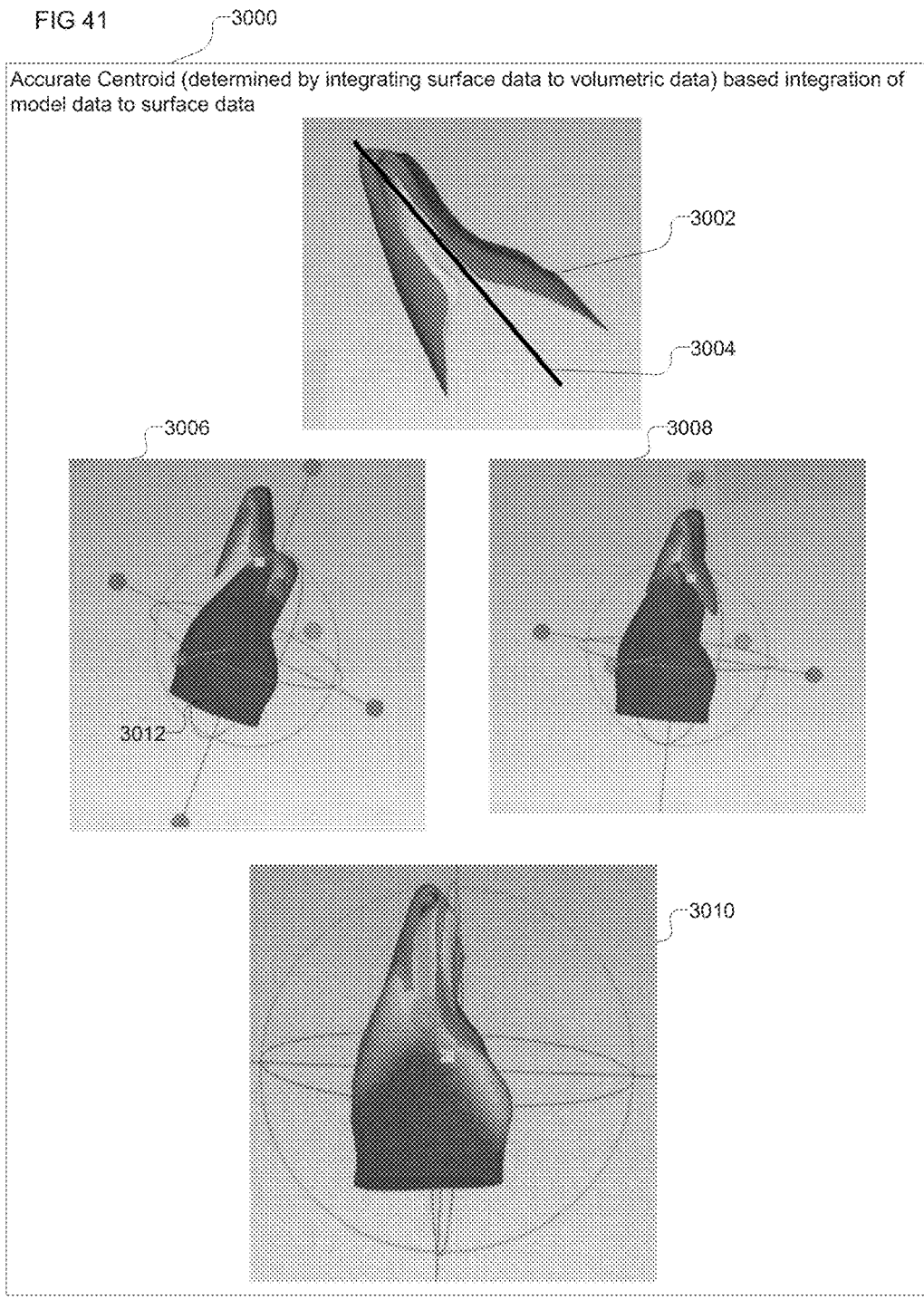
FIG. 41 illustrates a block diagram that shows how the model data is rotated, translated, and morphed to conform to a determined centroid to register the shape data of the patient's crown with the model data, in accordance with certain embodiments.

FIG. 41 illustrates a block diagram 3000 that shows, in accordance with certain embodiments, how the model data is rotated, translated, and morphed to conform to a determined centroid to register the shape data of the patient's crown with the model data.

In FIG. 41 an exemplary surface data 3002 is shown, where the surface data 3002 may be determined from intra-oral imagery, or by enhancing the intra oral imagery via volumetric data. A precise centroid 3004 is determined from the tooth shape determined by integrating the surface data 3002 with the corresponding volumetric data obtained from a CBCT image or other volumetric imagery. Once the centroid (i.e., an orientation) of the surface data (i.e., the crown) is determined, the model data 3012 is fitted to the surface data 3002 via appropriate translations, rotations, morphing etc. of the model data as shown via reference numerals 3006,3008, 3010.

Figure 42:
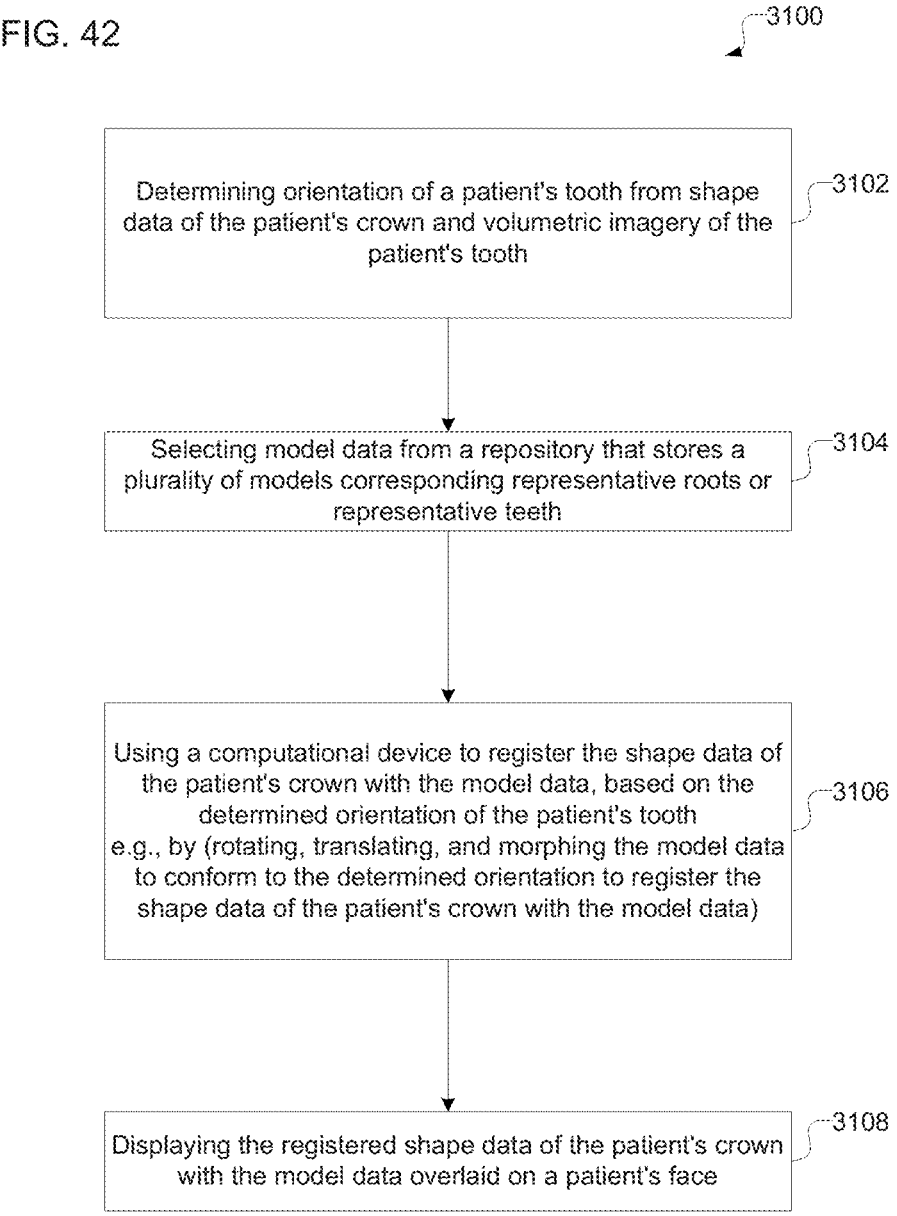
FIG. 42 illustrates a flowchart that shows integration of model data, surface data, and volumetric data, in accordance with certain embodiments.

FIG. 42 illustrates a flowchart 3100 that shows integration of model data 2507, surface data 2504, and volumetric data 2506, in accordance with certain embodiments. The operations shown in FIG. 42 may be performed by the model integrating application 2508 that executes in the computational device 2502.

Control starts at block 3102 in which the model integrating application 2508 determines an orientation of a patient's tooth from shape data (i.e., surface data 2504) of the patient's crown and volumetric imagery 2506 of the patient's tooth. In certain embodiments, the orientation may correspond to the centroid of the patient's tooth.

Control proceeds to block 3104 in which the model integrating application 2508 selects model data from a repository 2509 that stores a plurality of models corresponding to representative roots or representative teeth. A computational device 2502 is used to register (at block 3106) the shape data 2504 of the patient's crown with the model data 2507, based on the determined orientation of the patient's tooth. The registering may be performed by rotating, translating, and morphing the model data to conform the model data to the determined orientation of the shape data of the patient's crown. The registered shape data of the patient's crown is displayed (at block 3108) with the model data overlaid on a patient's face.

Therefore, FIGS. 12-42 illustrate certain embodiments in which shape data, volumetric imagery, and model data and integrated to provide a display of an esthetically pleasing tooth in which the crown corresponds to the imaged crown of the patient, whereas the root corresponds to a model root which is esthetically more pleasing in comparison to an imaged root of the patient.

Therefore, FIGS. 1-42 describe certain embodiments for using a digital reconstruction of a tooth, wherein the digital reconstruction includes a crown and a root. An image of the crown of the tooth is acquired, subsequent to a movement of the tooth. The shape data of the crown is extracted from the image and registered to the digital reconstruction of the tooth. In certain embodiments shown in FIGS. 1-42, the shape data is second shape data, wherein the performing of the digital reconstruction of the tooth comprises: receiving first shape data of the crown and volumetric imagery of the tooth, determining elements that represent the crown in the first shape data, and registering the elements with corresponding voxels of the volumetric imagery by determining volumetric coordinates and radiodensities corresponding to the voxels (it should be noted that the first shape data is acquired prior to the second shape data). In other embodiments, described in FIGS. 1-42, the shape data is second shape data, wherein the performing of the digital reconstruction of the tooth comprises: determining orientation of the tooth from first shape data of the crown and volumetric imagery of the tooth, and registering the first shape data of the crown with model data, based on the determined orientation of the tooth (it should be noted that the first shape data is acquired prior to the second shape data).

Additional Details of Embodiments

The operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal with computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 43:
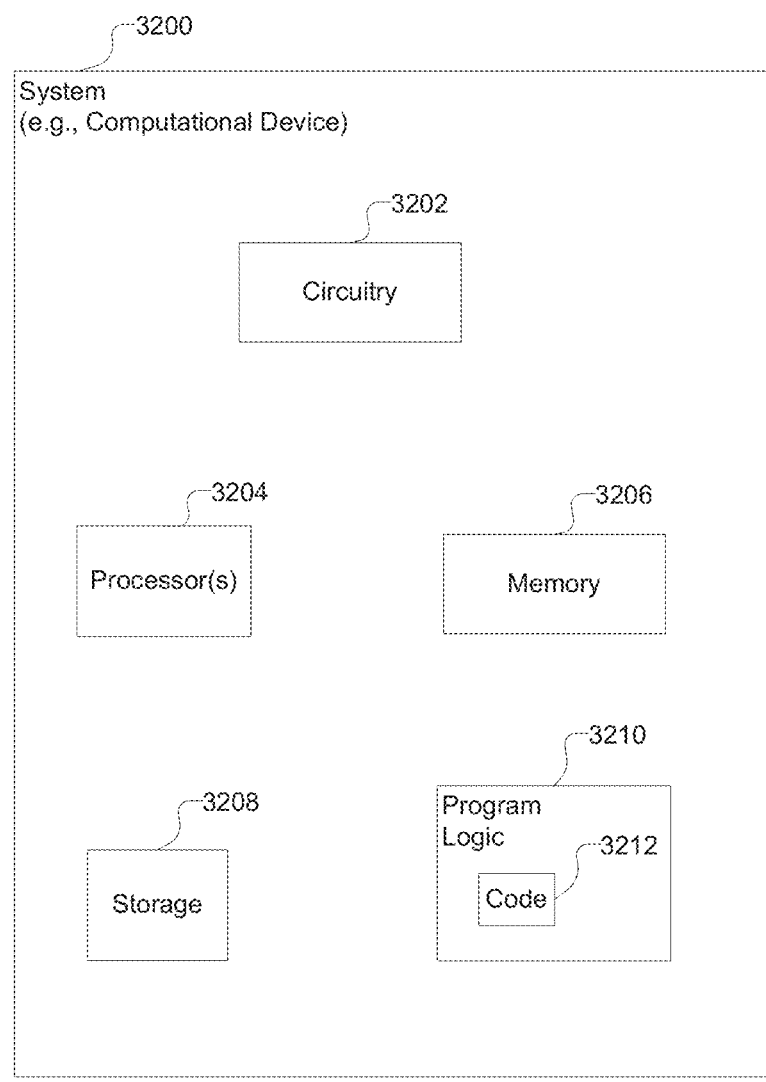
FIG. 43 illustrates a block diagram of a computational device, in accordance with certain embodiments.

FIG. 43 illustrates a block diagram that shows certain elements that may be included in the computational device 102, 2502, in accordance with certain embodiments. The system 3200 may comprise the computational device 102, 2502 and may include a circuitry 3202 that may in certain embodiments include at least a processor 3204. The processor 3204 may comprise any suitable processor known in the art, such as, an arithmetic logical unit, a central processing unit, a circuitry that perform operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 3204. The system 3200 may also include a memory 3206 (e.g., a volatile memory device), and storage 3208. The storage 3208 may include anon-volatile memory device (e.g., EEPROM, ROM, PROM, RAM, DRAM, SRAM, flash, firmware, programmable logic, etc.), magnetic disk drive, optical disk drive, tape drive, etc. The storage 3208 may comprise an internal storage device, an attached storage device and/or a network accessible storage device. The system 3200 may include a program logic 3210 including code 3212 that may be loaded into the memory 3206 and executed by the processor 3204 or circuitry 3202. In certain embodiments, the program logic 3210 including code 3212 may be stored in the storage 3208. In certain other embodiments, the program logic 3210 may be implemented in the circuitry 3202. Therefore, while FIG. 43 shows the program logic 3210 separately from the other elements, the program logic 3210 may be implemented in the memory 3206 and/or the circuitry 3202.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of digital reconstruction of a tooth, wherein the digital reconstruction includes a crown and a root, the method comprising:

receiving shape data of a crown of the tooth and volumetric imagery of the crown and a root of the tooth, the shape data and the volumetric imagery being of the tooth at a first position;

determining elements that represent one or more boundaries of the crown in the shape data;

registering the determined elements in the shape data with the volumetric imagery to identify a corresponding region of the tooth in the shape data and a corresponding region of the tooth in the volumetric imagery;

selecting data of the volumetric imagery in the corresponding region of the volumetric imagery;

building the root of the digital reconstruction using the selected data;

determining a position and an orientation of the root of the tooth subsequent to registering the determined elements;

acquiring an image of the crown of the tooth at a second position different from the first position subsequent to a movement of the tooth; and combining shape data of a corresponding region of the crown extracted from the image to the corresponding region of the crown of the digital reconstruction.

2. The method of claim 1, wherein receiving volumetric imagery includes receiving volumetric imagery selected from a group consisting of tomographic imagery, ultrasonic imagery, cone beam computed tomography (CBCT) imagery, and magnetic resonance imagery (MRI); and acquiring the image of the crown of the tooth includes acquiring the image via an intra-oral imaging system.

3. The method of claim 1, wherein after acquiring the image at the second position, the method further comprises:

combining shape data of a corresponding region of each of a plurality of crowns extracted from the image to the corresponding region of the corresponding crown of a digital reconstruction of the corresponding tooth, and wherein a spatial relationship of each crown to any adjacent crown in the acquired image is maintained during combining.

4. The method of claim 1, wherein the tooth moves from the first position to the second position while continuing to remain rigid, and wherein the movement of the tooth is caused by applying forces to the tooth.

5. The method of claim 1, wherein acquisition of at least one image for the digital reconstruction includes exposing a patient to x-ray radiation; and acquisition of the image of the crown avoids exposing the patient to any x-ray radiation.

6. The method of claim 1, wherein registering the determined elements includes determining volumetric coordinates and radiodensities of voxels in the corresponding region of the tooth in the volumetric imagery.

7. The method of claim 1, wherein building the root includes determining an orientation of the tooth and combining the corresponding region of the tooth in the shape data with model data based on the determined orientation of the tooth.

* * * * *